US008129185B2

(12) United States Patent
Blazar et al.

(10) Patent No.: US 8,129,185 B2
(45) Date of Patent: Mar. 6, 2012

(54) REGULATORY T CELLS AND THEIR USE IN IMMUNOTHERAPY AND SUPPRESSION OF AUTOIMMUNE RESPONSES

(75) Inventors: Bruce Blazar, Golden Valley, MN (US); Carl June, Merion Station, PA (US); Wayne R. Godfrey, Los Altos, CA (US); Richard G. Carroll, Lansdowne, PA (US); Bruce Levine, Cherry Hill, NJ (US); James L. Riley, Downingtown, PA (US); Patricia Taylor, St. Paul, MN (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 17 days.

(21) Appl. No.: 12/649,101

(22) Filed: Dec. 29, 2009

(65) Prior Publication Data

US 2010/0291678 A1 Nov. 18, 2010

Related U.S. Application Data

(62) Division of application No. 10/827,023, filed on Apr. 19, 2004, now Pat. No. 7,651,855.

(60) Provisional application No. 60/463,591, filed on Apr. 17, 2003, provisional application No. 60/550,481, filed on Mar. 5, 2004.

(51) Int. Cl.
*C12N 5/071* (2010.01)
*C12N 5/00* (2006.01)
*A01N 63/00* (2006.01)

(52) U.S. Cl. .............. 435/372.3; 435/325; 435/363; 435/366; 424/93.1; 424/93.2

(58) Field of Classification Search .................. None
See application file for complete search history.

(56) References Cited

U.S. PATENT DOCUMENTS

2004/0173778 A1 9/2004 Roncarolo et al.
2005/0101012 A1 5/2005 Schuler et al.

FOREIGN PATENT DOCUMENTS

WO WO02/072799 9/2002
WO WO02/097070 12/2002

OTHER PUBLICATIONS

Anasetti et al., "Prophylaxis of graft-versus-host disease by administration of the murine anti-IL-2 receptor antibody 2A3," *Bone Marrow Transplant* 7:375-381 (1991).
Apostolou, et al., "Origin of regulatory T cells with known specificity for antigen," *Nat Immunol* 3(8):756-763 (2002).
Asano et al., "Autoimmune disease as a consequence of developmental abnormality of a T cell subpopulation," *J. Exp. Med.* 184:387-396 (1996).
Asseman, et al., "An essential role for interleukin 10 in the function of regulatory T cells that inhibit intestinal inflammation," *J Exp Med* 190(7):995-1004 (1999).
Baecher-Allan et al., "CD4+CD25 high regulatory cells in human peripheral blood," *J. Immunol.* 167:1245-1253 (2001).
Banchereau et al., "Immunobiology of dendritic cells," *Annu Rev Immunol* 18:767-811 (2000).
Belkaid, et al., "CD4+CD25+ regulatory T Cells control *Leishmania major* persistence and immunity," *Nature* 420(6915):502-507 (2002).
Blaise et al., "Prevention of acute GVHD by in vivo use of anti-interleukin-2 receptor monoclonal antibody (33B3.1): a feasibility trial in 15 patients," *Bone Marrow Transplant* 8:105-111 (1991).
Bonomo et al., "Pathogenesis of post-thymectomy autoimmunity. Role of syngeneic MLR-reactive T cells," *J. Immunol.* 154:6602-6611(1995).
Cahn et al., "Treatment of acute graft-versus-host disease with methylprednisolone and cyclosporine with or without an anti-interleukin-2 receptor monoclonal antibody. A multicenter phase III study," *Transplantation* 60:939-942 (1995).
Carpenter et al., "Non-Fc receptor-binding humanized anti-CD3 antibodies induce apoptosis of activated human T cells," *J. Immunol.* 165:6205-6213 (2000).
CD25 MicroBeads human, Miltenyi Biotec, pp. 1-3.
CD8 Microbeads, Miltenyi Biotec online product literature, pp. 1-2, printed Apr. 2, 2007.
Cella et al., "Maturation, activation, and protection of dendritic cells induced by double-stranded RNA," *J Exp Med* 189(5):821-829 (1999).
Chai et al.,"CD4+CD25+ T Cells as immunoregulatory T cells in vitro," *Eur J Immunol* 32(8):2365-2375 (2002).
Chatenoud et al., "Suppressor T cells—they're back and critical for regulation of autoimmunity!" *Immunol. Rev.* 182:149-163 (2001).
Chen, "TGF-beta: the missing link in CD4+CD25+ regulatory T cell-mediated immunosuppression." 2003, Cytokine Growth Factor Rev 14:85-89. Chen et al., "Engagement of cytotoxic T lymphocyte-associated antigen 4 (CTLA-4) induces transforming growth factor beta (TGF-beta) production by murine CD4(+) T cells," *J. Exp. Med.* 188:1849-1857 (1998).
Cohen et al., "CD4(+)CD25(+) immunoregulatory T cells: new therapeutics for graft-versus-host disease," *J Exp Med* 196(3):401-406 (2002).
Dieckmann et al., "Ex vivo isolation and characterization of CD4(+)CD25(+) T cells with regulatory properties from human blood,"*J. Exp. Med.* 193:1303-1310 (2001).

(Continued)

*Primary Examiner* — Q. Janice Li
(74) *Attorney, Agent, or Firm* — Riverside Law LLP

(57) ABSTRACT

Based upon a strong correlation between regulator T cells (Treg cells) and suppressing or preventing a cytotoxic T cell response, provided are methods for the production of ex vivo activated and culture-expanded isolated CD4+CD25+ suppressor Treg cells for the prevention or suppression of immune reactions in a host, particularly in a human host, and including autoimmune responses. The resulting ex vivo culture-expanded Treg cells provide a sufficient amount of otherwise low numbers of such cells, having long term suppressor capability to permit therapeutic uses, including the preventing, suppressing, blocking or inhibiting the rejection of transplanted tissue in a human or other animal host, or protecting against graft vs host disease. Also provided are therapeutic and immunosuppressive methods utilizing the ex vivo culture-expanded Treg cells for human treatment, and high efficiency methods for research use.

2 Claims, 40 Drawing Sheets

OTHER PUBLICATIONS

Diehn et al., "Genomic expression programs and the integration of the CD28 costimulatory signal in T cell activation." 2002, PNAS 99(18):11796-11801.
Dye et al., "T cell-mediated immunosuppression as an obstacle to adoptive immunotherapy of the P815 mastocytoma and its metastases," J. Exp. Med. 154:1033-1042 (1981).
Dynabeads CD3/CD28 T Cell expander, manufacture datasheet, 2007.
Earle et al.,"In vitro expanded human CD4+CD25+ regulatory T cells suppress effector T cell proliferation." 2005, Clin Immunol. 115(1):3-9.
Edinger et al., "CD4+CD25+ regulatory T cells preserve graft-versus-tumor activity while inhibiting graft-versus-host disease after bone marrow transplantation," 9(9):1144-1150 (2003).
Elkord Biocompare Review, 1996.
Fukaura et al., "Induction of circulating myelin basic protein and proteolipid protein-specific transforming growth factor-beta1-secreting Th3 T cells by oral administration of myelin in multiple sclerosis patients," J. Clin. Invest. 98:70-77 (1996).
Gallimore et al., "Regulation of tumour immunity by CD25+ T cells," Immunology 107(1):5-9 (2002).
Gao et al., "CD4+CD25+ cells regulate CD8 cell energy in neonatal tolerant mice," Transplantation 68:1891-1897 (1999).
Gavin, et al., "Control of immune homeostasis by Naturally Arising Regulatory CD4+ T Cells," Curr Opin Immunol 15(6):690-696 (2003).
Godfrey et al., "Ex vivo depletion of alloreactive cells based on CFSE dye dilution, activation antigen selection, and dendritic cell stimulation," Blood 103:1158-1165 (Feb. 2004).
Godfrey et al., "In vitro expanded human CD4+CD25+ T regulatory cells can markedly inhibit allogeneic dendritic cell stimulated MLR cultures," Blood 104(2):453-461 (Jul. 15, 2004).
Greenfield et al., "B7.2 expressed by T cells does not induce CD28-mediated costimulatory activity but retains CTLA4 binding: implications for induction of antitumor immunity to T cell tumors," J. Immunol. 158:2025-2034 (1997).
Groux et al., "A CD4+ T-cell subset inhibits antigen-specific T-cell responses and prevents colitis," Nature 389:737-42 (1997).
Hall et al., "Anti-CD4 monoclonal antibody-induced tolerance to MHC-incompatible cardiac allografts maintained by CD4+ suppressor T cells that are not dependent upon IL-4," 161(10):5147-5146 (1998).
Hansen et al., "Monoclonal antibodies identifying a novel T-cell antigen and Ia antigens of human lymphocytes," Immunogenetics 10:247-260 (1980).
Hara et al., "IL-10 is required fur regulatory T cells to mediate tolerance to alloantigens in vivo," J. Immunol. 166:3789-3796 (2001).
Harris et al., "Prevention of graft-versus-host disease (GVHD) by elimination of recipient-reactive donor T cells with recombinant toxins that target the interleukin 2 (IL-2) receptor," Bone Marrow Transplant 23:137-144 (1999).
Hoffmann et al., "Large-scale in vitro expansion of polyclonal human CD4(+)CD25high regulatory T cells." 2004, Blood, 104(3):895-903.
Hoffmann et al., "Donor-type CD4(+)CD25(+) regulatory T cells suppress lethal acute graft-versus-host disease after allogeneic bone marrow transplantation," J Exp Med 196(3):389-399 (2002).
Jiang et al., "Induction of allopeptide-specific human CD4+CD25+ regulatory T cells ex vivo," Blood 102(6):2180-2186 (2003).
Jones et al., "Post-hematopoietic cell transplantation control of graft-versus-host disease by donor CD425 T cells to allow an effective graft-versus-leukemia response," Biol Blood Marrow Transplant 9(4):243-256 (2003).
Jonuleit et al., "Infectious tolerance: human CD25(+) regulatory T cells convey suppressor activity to conventional CD4(+) T helper cells," J. Exp. Med. 196:255-260 (2002).
Jonuleit et al., "Identification and functional characterization of human CD4(+)CD25(+) T cells with regulatory properties isolated from peripheral blood," J. Exp. Med. 193:1285-1294 (2001).
Kung et al., "Monoclonal antibodies defining distinctive human T cell surface antigens," Science 206:347-349 (1979).
Laport et al., "Adoptive transfger of costimulated T cells induces lymphocytosis in patients with relapsed/refractory non-Hodgkin lymphoma following CD34+ selected hematopoietic cell transplantation," Blood 102(6):2004-2013 (2003).
Lenardo, "Interleukin-2 programs mouse alpha beta T lymphocytes for apoptosis," Nature 353:858-861 (1991).
Levine et al., "Effects of CD28 costimulation on long-term proliferation of CD4+ T cells in the absence of exogenous feeder cells," J. Immunol. 159(12): 5921-5930 (1997).
Levings et al., "Human CD25+CD4+ T suppressor cell clones produce transforming growth factor beta, but not interleukin 10, and are distinct from type 1 T regulatory cells," J. Exp. Med. 196:1335-1346 (2002).
Levings et al., "Human cd25(+)cd4(+) t regulatory cells suppress naive and memory T cell proliferation and can be expanded in vitro without loss of function," J. Exp. Med. 193:1295-1302 (2001).
Lin et al., "Efficient expansion of regulatory T cells in vitro and in vivo with a CD28 superagonist," Eur J. Immunol 33(3):626-638 (2003).
Lissy et al., "TCR antigen-induced cell death occurs from a late G1 phase cell cycle check point," Immunity 8:57-65 (1998).
Nakamura et al., "Cell contact-dependent immunosuppression by CD4(+)CD25(+) regulatory T cells is mediated by cell surface-bound transforming growth factor beta," J. Exp. Med. 194:629-644 (2001).
Ng, et al., "Human CD4(+)CD25(+) cells: a naturally occurring population of regulatory T cells," Blood 98(9):2736-2744 (2001).
Ochsenbein, et al., "Roles of tumour localization, second signals and cross priming in cytotoxic T-cell induction," Nature 411:1058-1064 (2001).
Onizuka et al., "Tumor rejection by in vivo administration of anti-CD25 (interleukin-2 receptor alpha) monoclonal antibody," Cancer Res. 59:3128-3133 (1999).
Pasare et al., "Toll pathway-dependent blockade of CD4+CD25+ T cell-mediated suppression by dendritic cells," Science (5609):1033-1036 (2003).
Peng et al., "Tumor-induced L-selectin high suppressor T cells mediate potent effector T cell blockade and cause failure of otherwise curative adoptive immunotherapy," J. Immunol 169(9):4811-4821 (2002).
Piccirillo et al., "Cutting edge: control of CD8+ T cell activation by CD4+CD25+ immunoregulatory cells," J. Immunol. 167:1137-1140 (2001).
Read et al., "Cytotoxic T lymphocyte-associated antigen 4 plays an essential role in the function of CD25(+)CD4(+) regulatory cells that control intestinal inflammation," J. Exp. Med. 192:295-302 (2000).
Sakaguchi, "Naturally arising CD4 regulatory T cells for immunologic self-tolerance and negative control of immune responses," Annu Rev Immunol (2004, published on-line Nov. 17, 2003).
Sakaguchi et al., "Immunologic self-tolerance maintained by activated T cells expressing IL-2 receptor alpha-chains (CD25). Breakdown of a single mechanism of self-tolerance causes various auto immune diseases." J. Immunol. 155:1151-1164 (1995).
Sakaguchi et al., "Immunologic tolerance maintained by CD25+ CD4+ regulatory T cells: their common role in controlling autoimmunity, tumor immunity, and transplantation tolerance," Immunol. Rev. 182:18-32 (2001).
Sallusto et al., "Efficient presentation of soluble antigen by cultured human dendritic cells is maintained by granulocyte/macrophage colony-stimulating factor plus interleukin 4 and downregulated by tumor necrosis factor alpha," J Exp Med 179(4):1109-1118 (1994).
Salomon et al., "CD28 costimulation is essential for the homeostasis of the CD4+CD25+ immunoregulatory T cells that control autoimmune diabetes," Immunity 12:431-440 (2000).
Shevach, "CD4+ CD25+ suppressor T cells: more questions than answers," Nat. Rev. Immunol. 2:389-400 (2002).
Shevach, "Certified professionals: CD4(+)CD25(+) suppressor T cells," J. Exp. Med. 193:F41-F46 (2001).
Shevach, "Regulatory T cells in autoimmmunity,"Annu. Rev. Immunol. 18:423-449 (2000).
Shevach et al., "Control of T-cell activation by CD4+CD25+ suppressor T cells," Immunol Rev 182:58-67 (2001).
Shimizu et al., "Induction of tumor immunity by removing CD25+CD4+ T cells: a common basis between tumor immunity and autoimmunity," J. Immunol. 163:5211-5218 (1999).

Spisek et al., "Standardized generation of fully mature p70 IL-12 secreting monocyte-derived dendritic cells for clinical use," *Cancer Immunol Immunother* 50(8):417-421 (2001).

Staveley-O'Carroll, et al., "Induction of antigen-specific T cell anergy: An early event in the course of tumor progression," *Proc. Natl. Acad. Sci. USA* 95:1178-1183 (1998).

Stephens et al., "Human CD4(+)CD25(+) thymocytes and peripheral T cells have immune suppressive activity in vitro," *Eur. J. Immunol.* 31:1247-1254 (2001).

Suri-Payer et al., "CD4+CD25+ T cells inhibit both the induction and effector function of autoreactive T cells and represent a unique lineage of immunoregulatory cells," *J. Immunol.* 160:1212-1218 (1998).

Sufi-Payer et al., "Pathogenesis of post-thymectomy autoimmune gastritis. Identification of anti-H/K adenosine triphosphatase-reactive T cells," *J. Immunol.* 157:1799-1805 (1996).

Sutmuller, et al., "Synergism of cytotoxic T lymphocyte-associated antigen 4 blockade and depletion of CD25(+) regulatory T cells in antitumor therapy reveals alternative pathways for suppression of autoreactive cytotoxic T lymphocyte responses," *J. Exp. Med.* 194:823-832 (2001).

Suvas, et al., "CD4+CD25+ T Cells regulate virus-specific primary and memory CD8+ T cell responses," *J Exp Med* 198(6):889-901 (2003).

Taams, et al., "Human anergic/suppressive CD4(+)CD25(+) T cells: a highly differentiated and apoptosis-prone population," *Eur. J. Immunol.* 31:1122-1131 (2001).

Takahashi et al., "Immunologic self-tolerance maintained by CD25+CD4+ naturally anergic and suppressive T cells: induction of autoimmune disease by breaking their anergic/suppressive state," *Int. Immunol.* 10:1969-1980 (1998).

Takahashi et al., "Immunologic self-tolerance maintained by CD25(+)CD4(+) regulatory T cells constitutively expressing cytotoxic T lymphocyte-associated antigen 4," *J. Exp. Med.* 192:303-310 (2000).

Taylor et al., "CD4(+)CD25(+) immune regulatory cells are required for induction of tolerance to alloantigen via costirnulatory blockade," *J. Exp. Med.* 193:1311-1318 (2001).

Taylor et al., "The infusion of ex vivo activated and expanded CD4(+)CD25(+) immune regulatory cells inhibits graft-versus-host disease lethality," *Blood* 99(10):3493-3499 (2002).

Thornton et al., "CD4+CD25+ immunoregulatory T cells suppress polyclonal T cell activation in vitro by inhibiting interleukin 2 production," *J. Exp. Med.* 188:287-296 (1998).

Thornton et al., "Suppressor effector function of CD4+CD25+ immunoregulatory T cells is antigen nonspecific," *J. Immunol.* 164:183-190 (2000).

Thornton, et al., "Activation requirements for the induction of CD4+CD25+ T cell suppressor function," *Eur J Immunol* 34(2):366-376 (2004).

Thorstenson et al., "Generation of anergic and potentially immunorgulatory CD25+CD4 T cells in vivo after induction of peripheral tolerance with intravenous or oral antigen," *J Immunol* 167(1)188-195 (2001).

Trenado et al., "Recipient-type specific CD4+CD25+ regulatory T cells favor immune reconstitution and control graft-vesus-host disease while maintaining graft-versus-leukemia," *J Clin Invest* 112(11):1688-1696 (2003).

Vella et al., "Cytokine-induced survival of activated T cells in vitro and in vivo," *Proc. Natl. Acad. Sci. USA* 95:3810-3815 (1998).

Walker et al., "Induction of FoxP3 and acquisition of T regulatory activity by stimulated human CD4+CD25+ T cells," *J Clin Invest* 112(9):1437-1443 (2003).

Wesselborg et al., "Induction of activation-driven death (apoptosis) in activated but not resting peripheral blood T cells," *J. Immunol.* 150:4338-4345 (1993).

Willerford et al., "Interleukin-2 receptor alpha chain regulates the size and content of the peripheral lymphoid compartment," *Immunity* 3:521-530 (1995).

Woo et al., "Regulatory CD4(+)CD25(+) T cells in tumors from patients with early-stage non-small cell lung cancer and late-stage ovarian cancer," *Cancer Res.* 61:4766-4772 (2001).

'Wood. et al., "Regulatory T cells in transplantation tolerance," *Nat Rev Immunol* 3(3):199-210 (2003).

Yamagiwa et al., "A role for TGF-beta in the generation and expansion of CD4+CD25+ regulatory T cells from human peripheral blood," *J. Immunol.* 166:7282-7289 (2001).

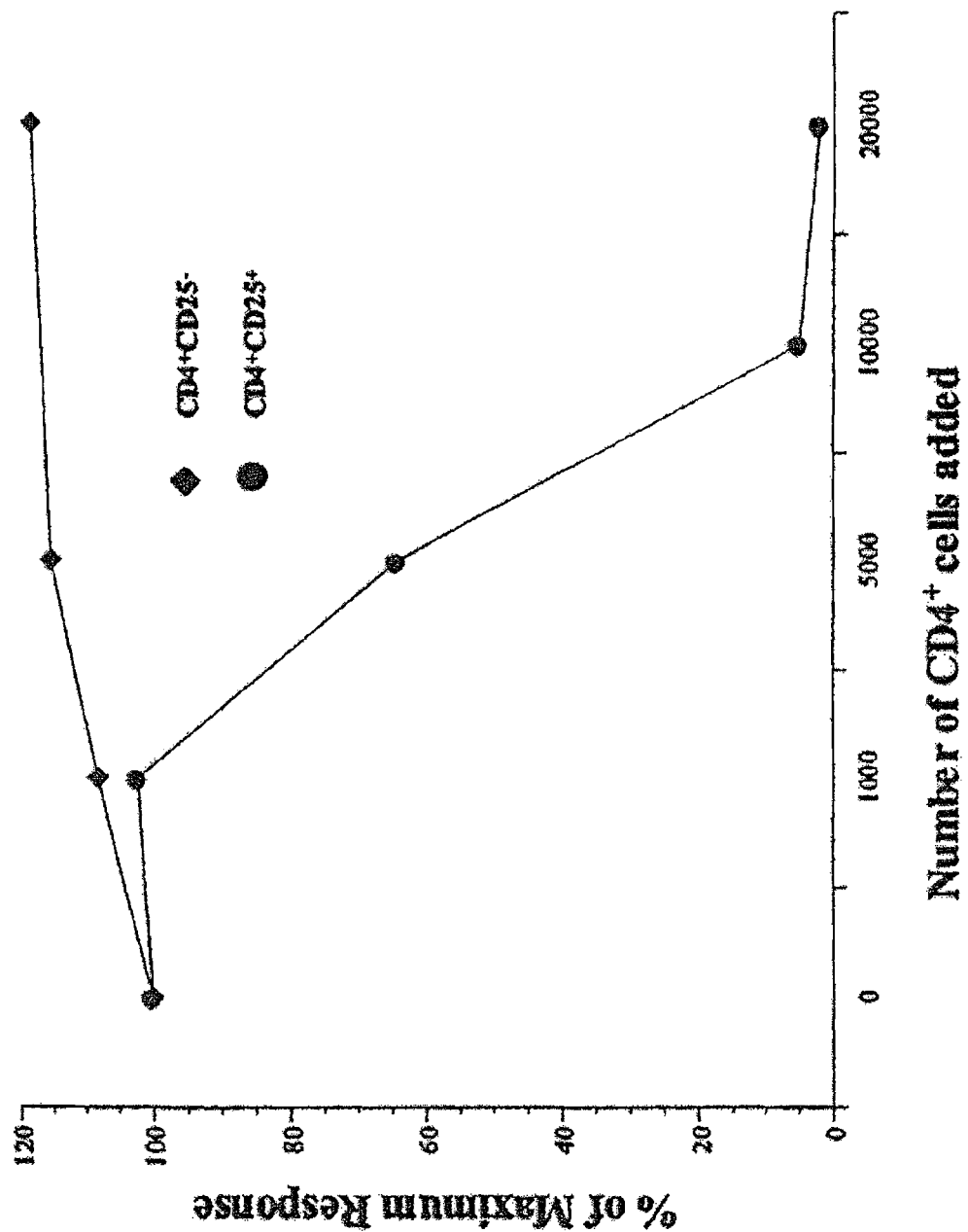

Number of CD4+CD25+ cells added

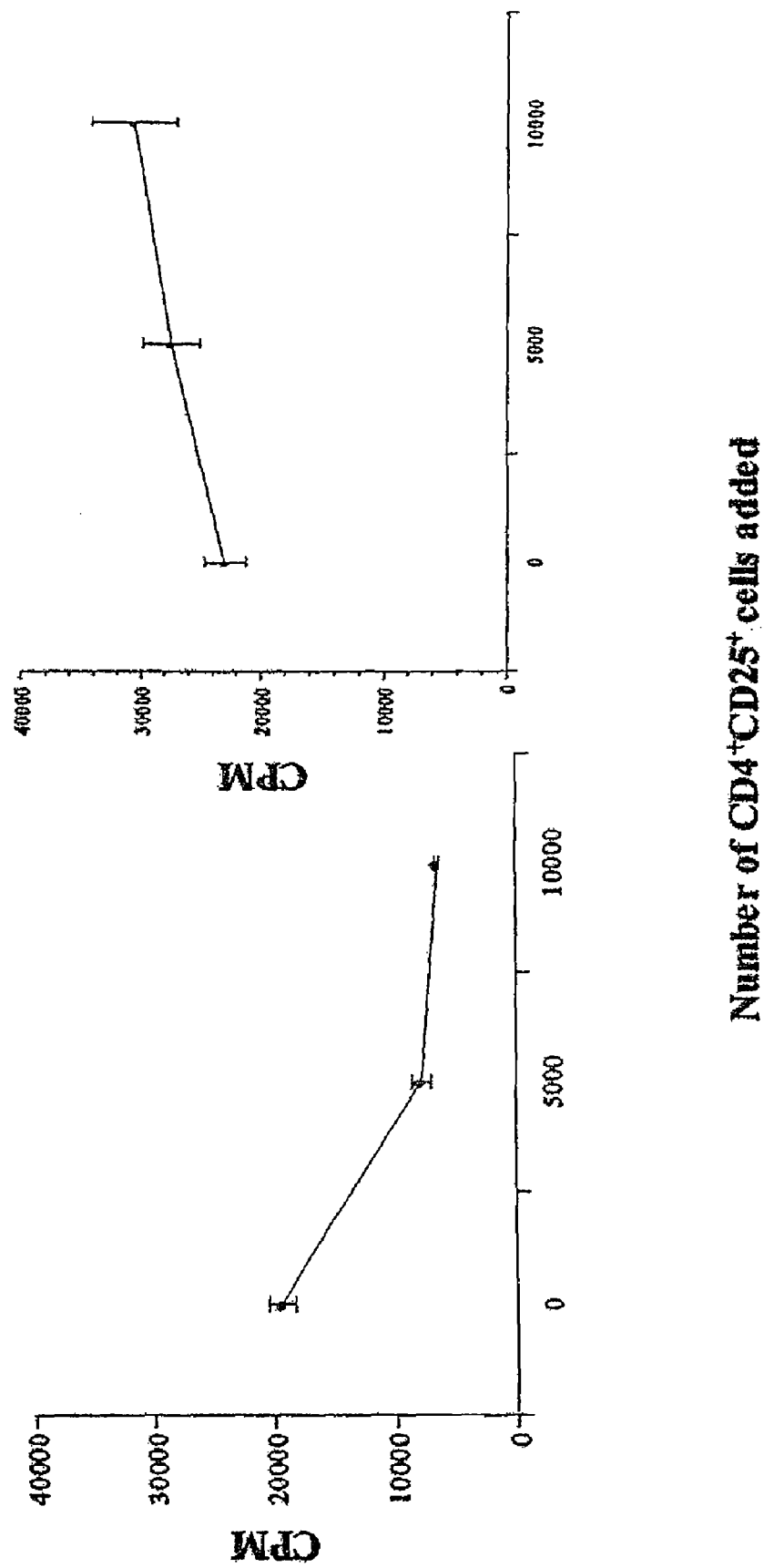

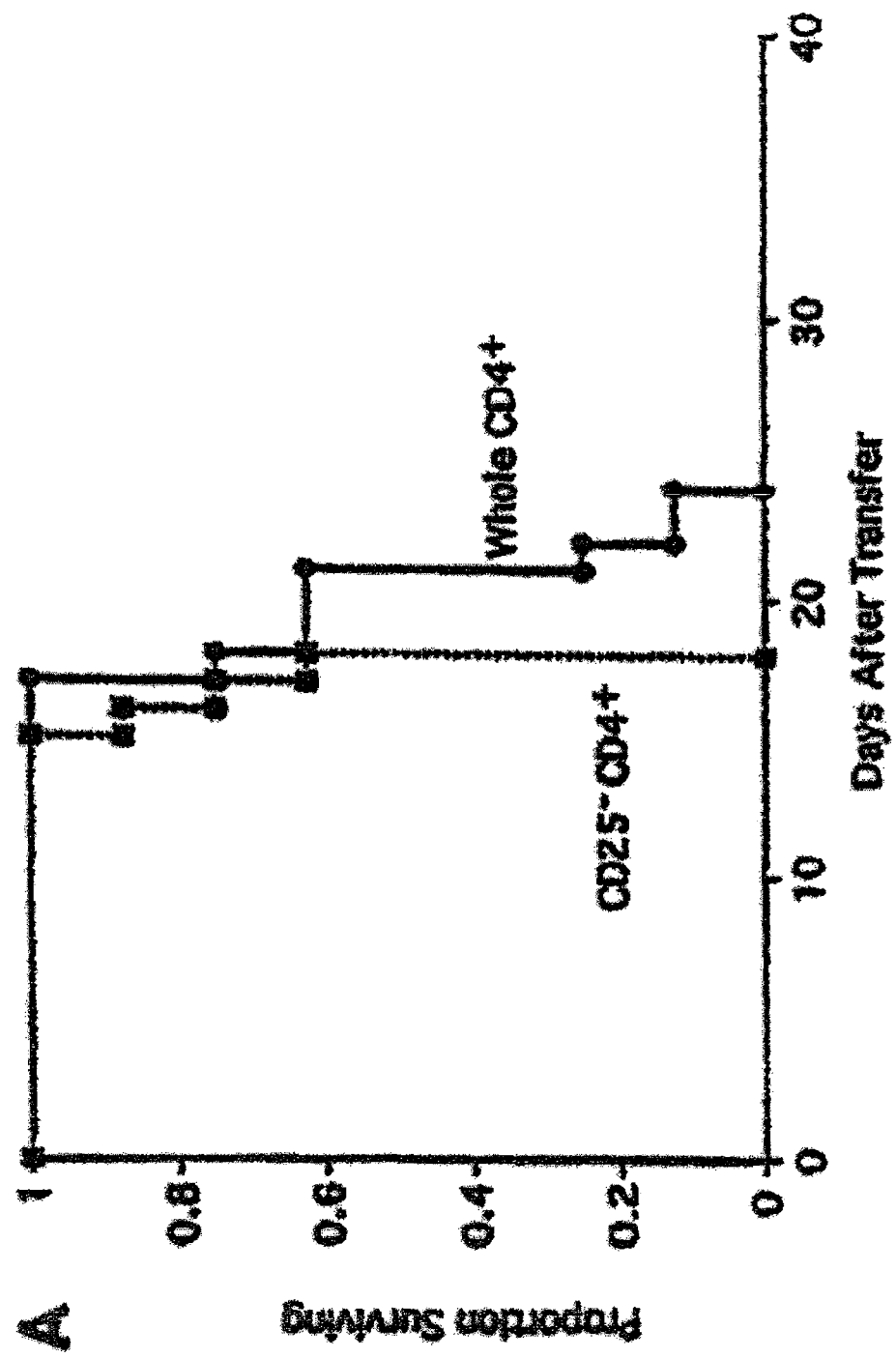

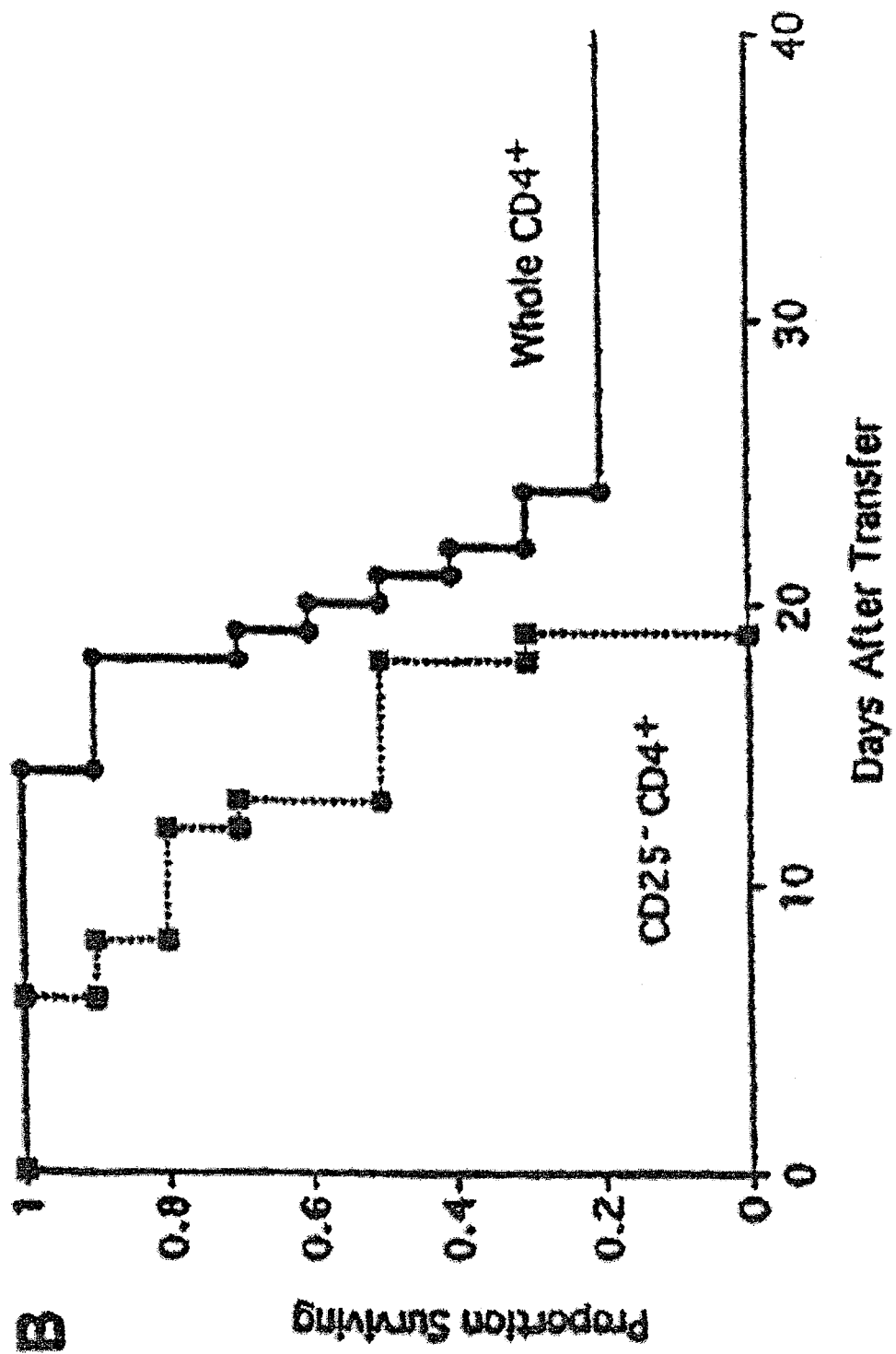

FIG. 15C
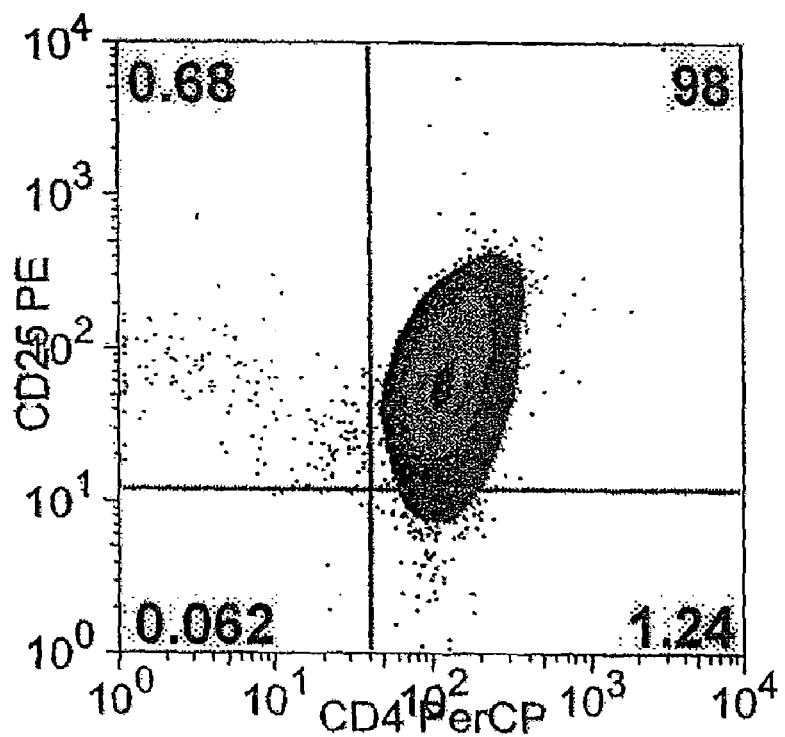
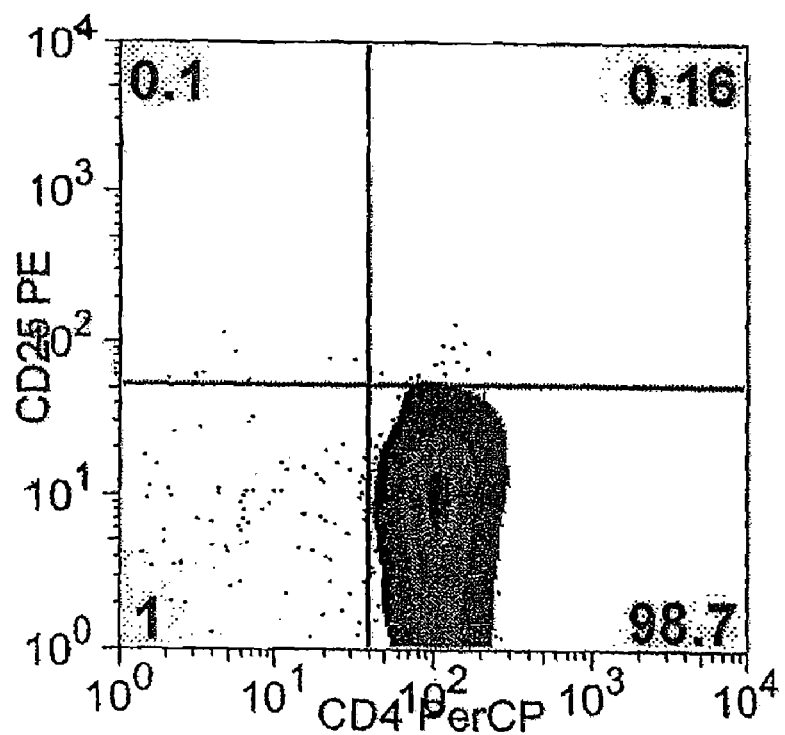
FIG. 15D

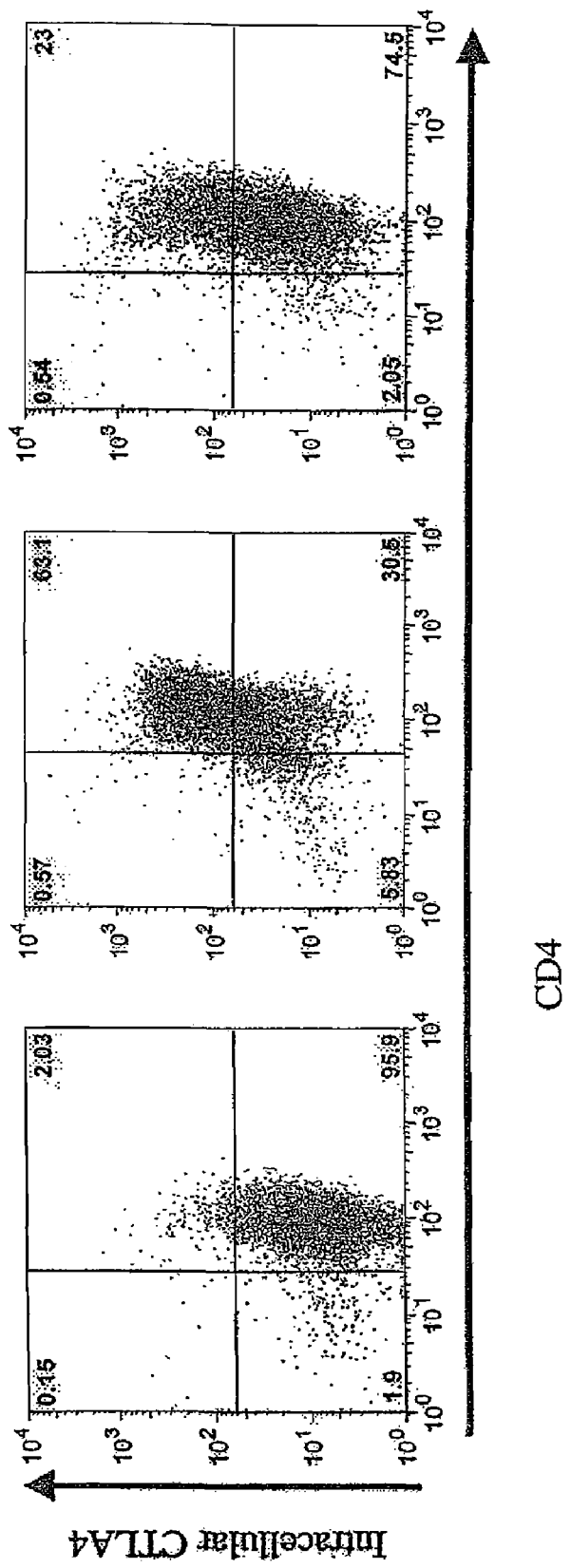

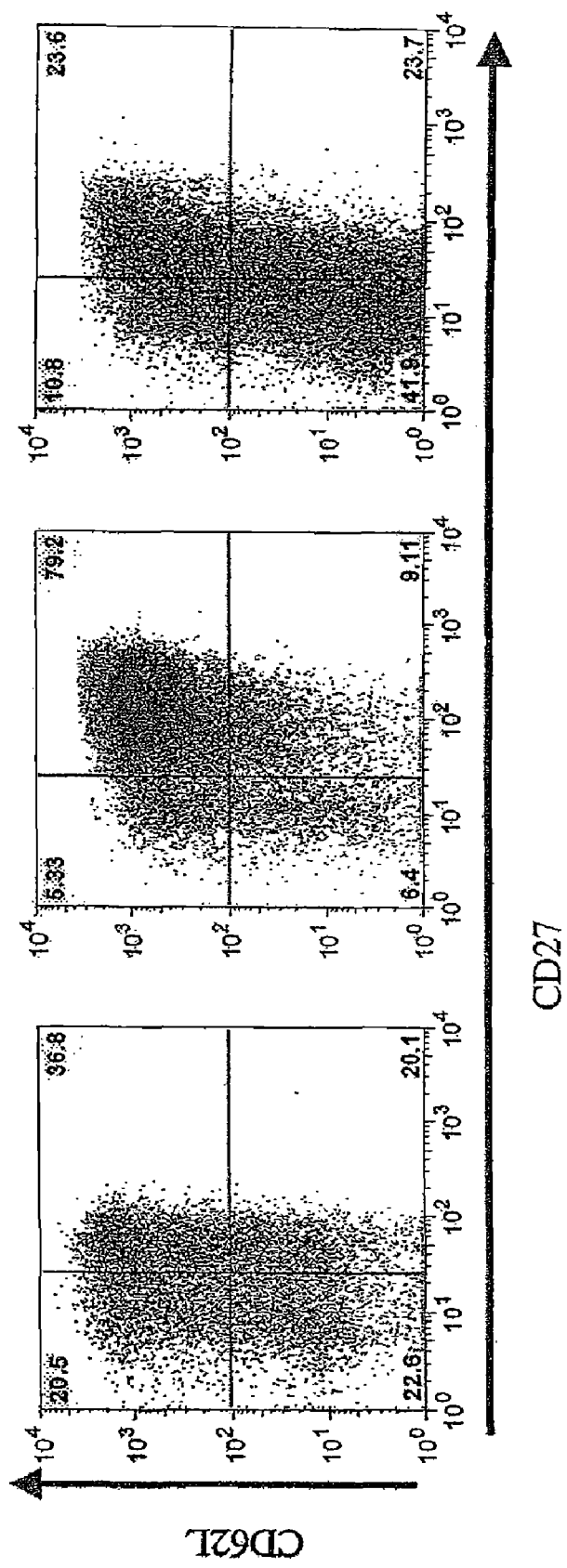

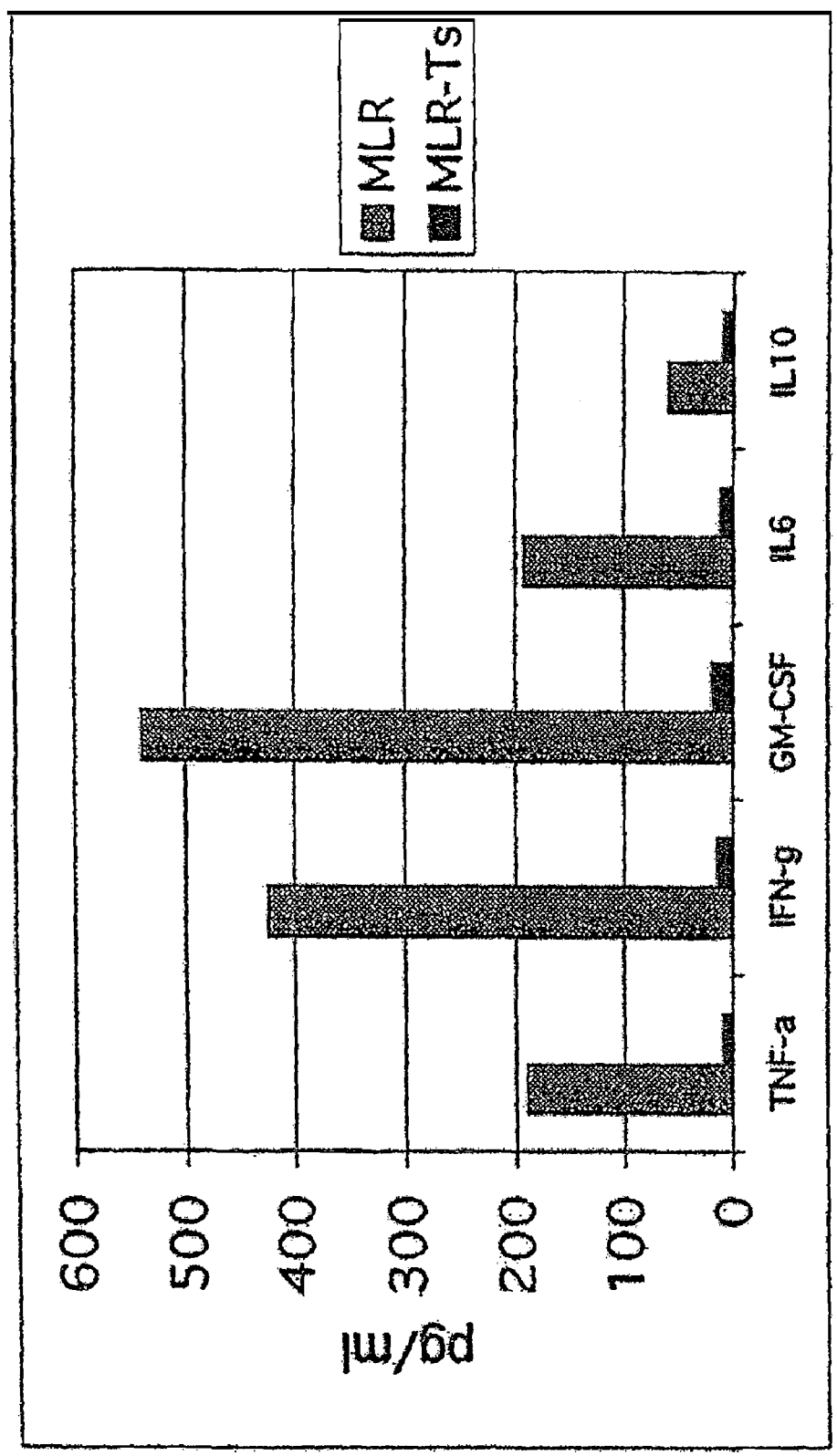

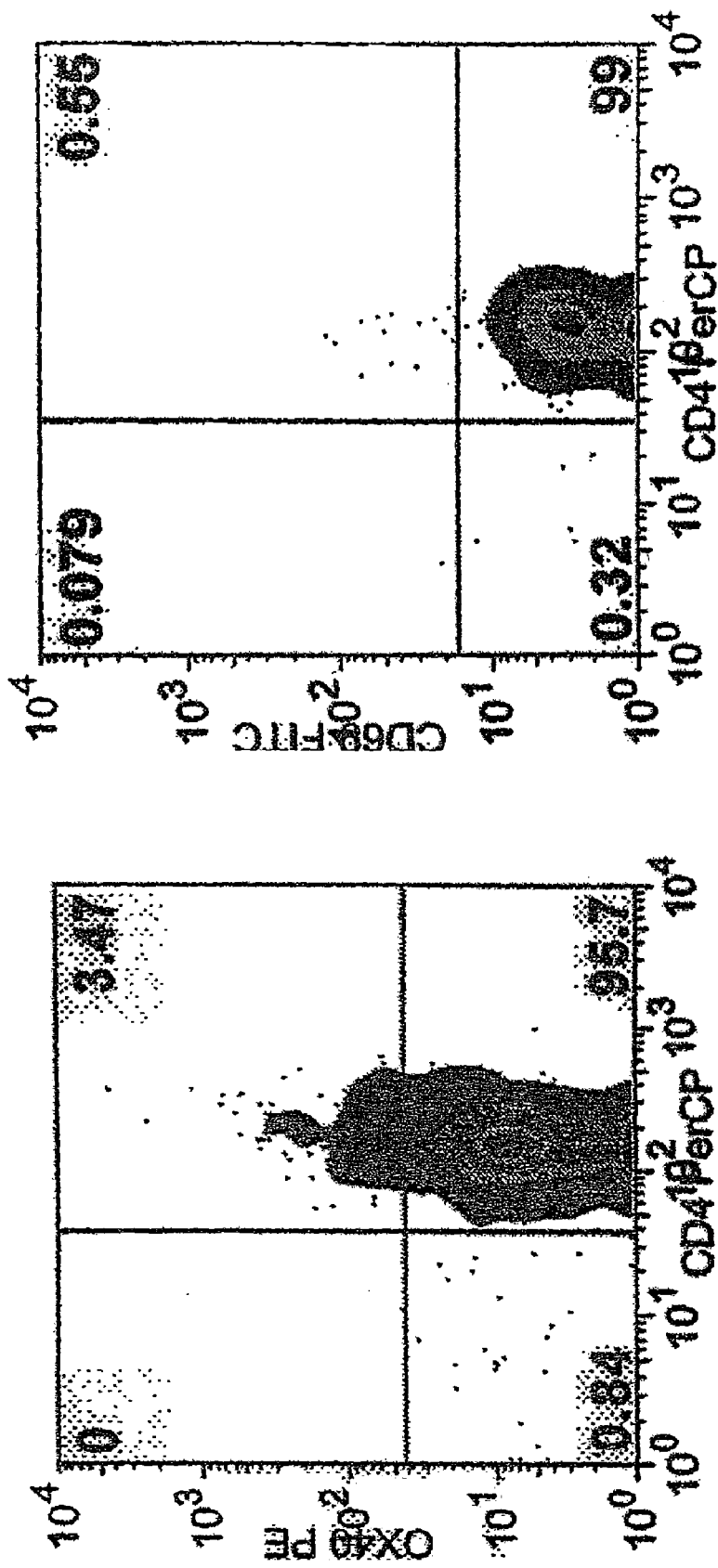

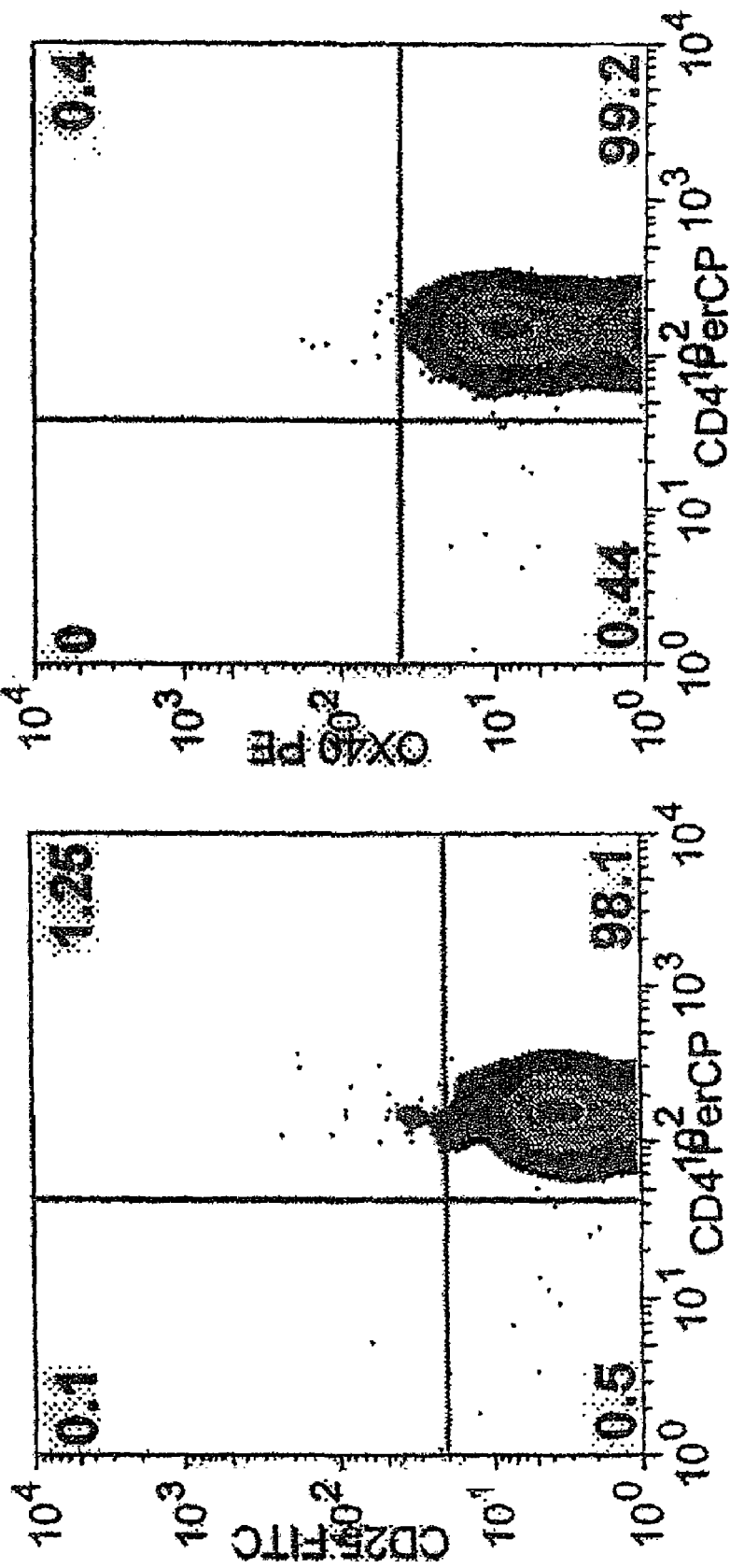

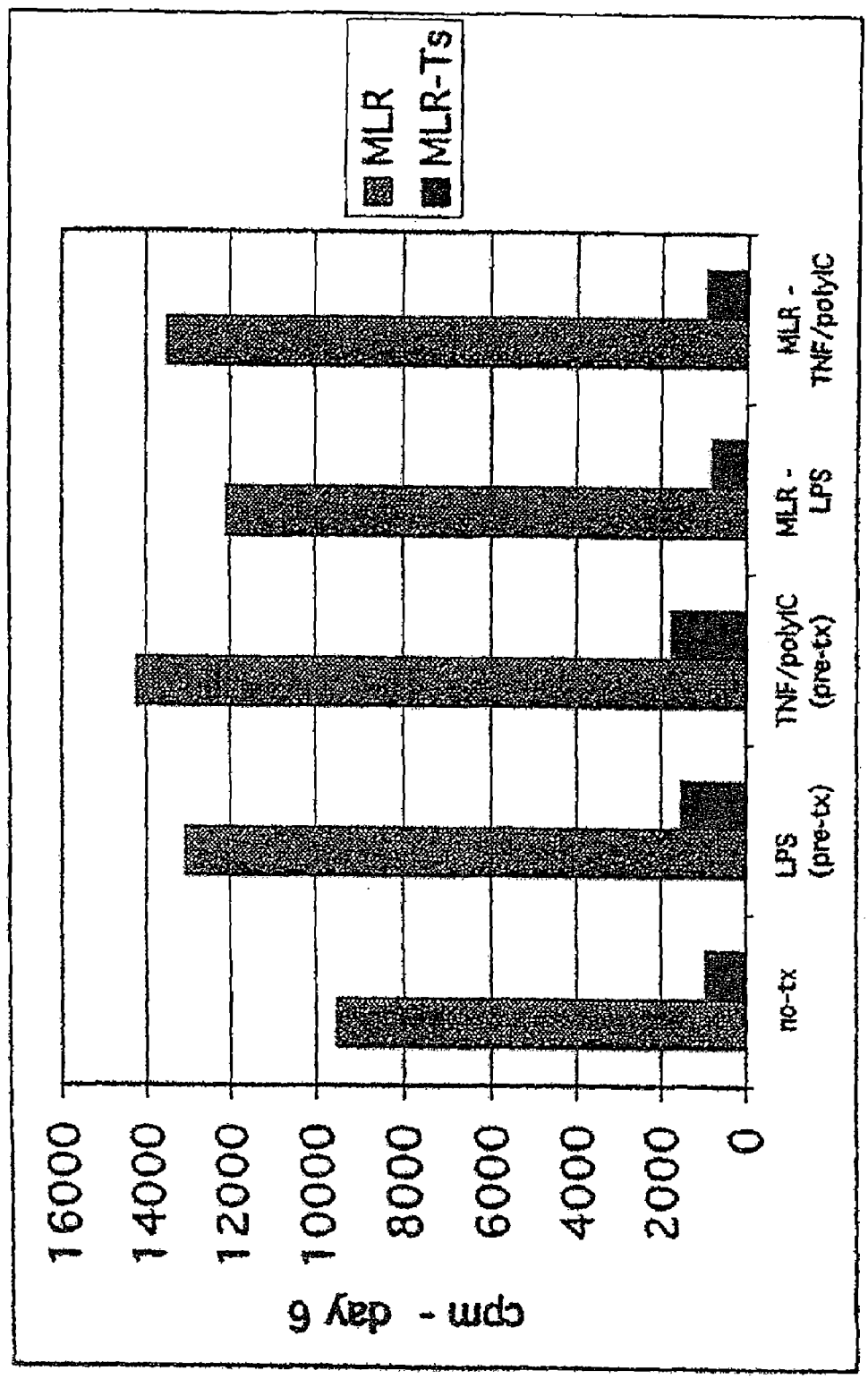

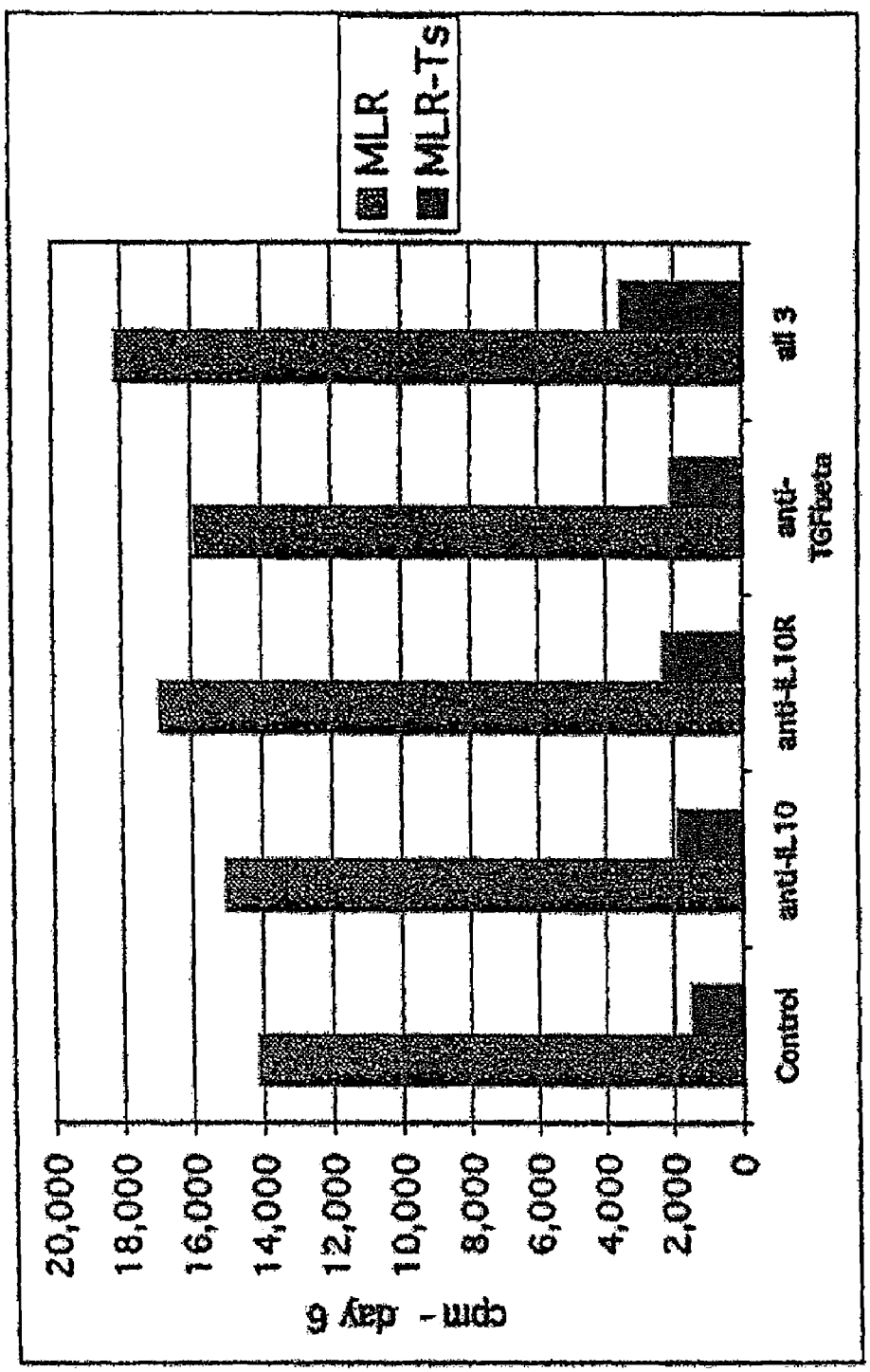

REGULATORY T CELLS AND THEIR USE IN IMMUNOTHERAPY AND SUPPRESSION OF AUTOIMMUNE RESPONSES

CROSS REFERENCE TO RELATED APPLICATIONS

This Application is a divisional of U.S. application Ser. No. 10/827,023, filed Apr. 19, 2004, now issued as U.S. Pat. No. 7,651,855, which is entitled to priority pursuant to 35 U.S.C, §119(e) to U.S, Provisional Application No. 60/463,591, filed Apr. 17, 2003 and U.S. Provisional Application No. 60/550,481, filed Mar. 5, 2004 which are incorporated by reference in their entirety.

GOVERNMENT INTEREST

This invention was made with government support under Grant Nos. R01 AI34495, R37 HL56067, and PO1 AI 35225 awarded by the National Institutes of Health. The Government has certain rights in this invention.

FIELD OF THE INVENTION

The present invention relates to regulatory T cells and methods of long-term, culture-expanding, activating and using same in immunotherapy and for the suppression of autoimmune responses, including GVHD.

BACKGROUND OF THE INVENTION

It has long been thought that suppressor cells play a role in the progression of cancer (Dye et al., J. Exp. Med. 154:1033-1042 (1981)). In fact, active suppression by T regulatory cells plays an important role in the down-regulation of T cell responses to foreign and self-antigens.

T cells are a class of lymphocytes, having specific T cell receptors (TCRs) that are produced as a result of gene rearrangement. T cells have diverse roles, which are accomplished by the differentiation of distinct subsets of T cells, recognizable by discrete patterns of gene expression. Several major T cell subsets are recognized based on receptor expression, such as TCR-$\alpha/\beta$, and TCR $\gamma/\Delta$ and invariant natural killer cells. Other T cell subsets are defined by the surface molecules and cytokines secreted therefrom. For example, T helper cells (CD4 cells) secrete cytokines, and help B cells and cytotoxic T cells to survive and carry out effector functions. Cytotoxic T cells (CTLs) are generally CD8 cells, and they are specialized to kill target cells, such as infected cells or tumor cells. Natural killer (NK) cells are related to T cells, but do not have TCRs, and have a shorter lifespan, although they do share some functions with T cells and are able to secrete cytokines and kill some kinds of target cells.

Human and mouse peripheral blood contains a small population of T cell lymphocytes that express the T regulatory phenotype ("Treg"), i.e., positive for both CD4 and CD25 antigens (i.e., those $CD4^+$ T cells that are also distinctly positive for CD25). First characterized in mice, where they constitute 6-10% of lymph node and splenic $CD4^+$ T cell populations, this population of $CD4^+CD25^+$ cells represents approximately only 5-10% of human peripheral blood mononuclear cells (PBMC), or 2-7% of $CD4^+$ T cells, although some donors exhibit a more distinct population of $CD4^+$ and $CD25^+$ cells. About 1-2% of human peripheral blood PBMCs are both CD4 positive ($CD4^+$) and CD25 brightly positive ($CD25^+$) cells.

There are several subsets of Treg cells (Bluestone et al., Nature Rev. Immunol. 3:253 (2003)). One subset of regulatory cells develops in the thymus. Thymic derived Treg cells function by a cytokine-independent mechanism, which involves cell to cell contact (Shevach, Nature Rev. Immunol 2:389 (2002)). They are essential for the induction and maintenance of self-tolerance and for the prevention of autoimmunity (Shevach, Annu. Rev. Immunol. 18:423-449 (2000); Stephens et al., 2001; Turns et al., 2001; Thornton et al., 1998; Salomon et al., Immunity 12:431-440 (2000); Sakaguchi et al., Immunol. Rev. 182:18-32 (2001)). These professional regulatory cells prevent the activation and proliferation of autoreactive T cells that have escaped thymic deletion or recognize extrathymic antigens, thus they are critical for homeostasis and immune regulation, as well as for protecting the host against the development of autoimmunity (Suri-Payer et al., J. Immunol. 157:1799-1805 (1996); Asano et al., J. Exp. Med. 184:387-396 (1996); Bonomo et al., J. Immunol. 154:6602-6611 (1995); Willerford et al., Immunity 3:521-530 (1995); Takahashi et al., Int. Immunol. 10:1969-1980 (1998); Salomon et al., Immunity 12:431-440 (2000); Read et al., J. Exp. Med. 192:295-302 (2000). Thus, immune regulatory $CD4^+CD25^+$ T cells are often referred to as "professional suppressor cells."

However, Treg cells can also be generated by the activation of mature, peripheral $CD4^+$ T cells. Studies have indicated that peripherally derived Treg cells mediate their inhibitory activities by producing immunosuppressive cytokines, such as transforming growth factor-beta (TGF-$\beta$) and IL-10 (Kingsley et al., J. Immunol. 168:1080 (2002); Nakamura et al., J. Exp. Med. 194:629-644 (2001)). After antigen-specific activation, these Treg cells can non-specifically suppress proliferation of either $CD4^+$ or $CD25^+$ T cells (demonstrated by FACS sorting in low dose immobilized anti-CD3 mAb-based co-culture suppressor assays by Baecher-Allan et al., J. Immunol. 167(3):1245-1253 (2001)).

Studies have shown that $CD4^+CD25^+$ cells are able to inhibit anti-CD3 stimulation of T cells when co-cultured with autologous antigen presenting cells (APC), but only through direct contact (Stephens et al., Eur. J. Immunol. 31:1247-1254 (2001); Taams et al., Eur. J. Immunol. 31:1122-1131 (2001); Thornton et al., J. Exp. Med. 188:287-296 (1998)). However, in mice this inhibitory effect was not able to overcome direct T cell stimulation with immobilized anti-CD3 or with anti-CD3/CD28 (Thornton et al., 1998). In previous reports, human $CD4^+CD25^+$ T cells isolated from peripheral blood required pre-activation in order to reveal their suppressive properties, as direct culture of the regulatory cells was generally insufficient to mediate suppressive effects (Dieckmann et al., J. Exp. Med. 193:1303-1310 (2001)). Others have also found that the inhibitory properties of human $CD4^+CD25^+$ T cells are activation-dependent, but antigen-nonspecific (Jonuleit et al., J. Exp. Med. 193:1285-1294 (2001); Levings et al., J. Exp. Med. 193(11):1295-1302 (2001); Yamagiwa et al., J. Immunol. 166:7282-7289 (2001)), and have demonstrated constitutive expression of intracellular stores of cytotoxic T lymphocyte antigen-4 (CTLA-4) (Jonuleit et al., 2001; Read et al., J. Exp. Med. 192:295-302 (2000); Yamagiwa et al., 2001; Takahashi et al., J. Exp. Med. 192:303-310 (2000)). Moreover, after T-cell receptor (TCR)-mediated stimulation, $CD4^+CD25^+$ T cells suppress the activation of naive $CD4^+CD25^+$ T cells activated by alloantigens and mitogens (Jonuleit et al., 2001).

Both mouse and human Treg cells express CTLA-4, however the role of CTLA-4 in tolerance induction and its capacity to impart inhibitory function to regulatory $CD4^+CD25^+$ T cells is controversial. CTLA-4 (also known as CD152) is a homolog of CD28 and is a receptor for the CD80 and CD86 ligands. CTLA-4 inhibits T cell responses in an antigen and TCR-dependent manner. T cells that have impaired CTLA-4 function have enhanced T cell proliferation and cytokine production. In contrast, enhanced CTLA-4 function leads to inhibited cytokine secretion and impaired cell cycle progression both in vitro and in vivo. In the mouse, CTLA-4 is not required for suppressive function of the Treg cells, as opposed to its requirement in humans. This may be explained in part by the recent discovery that there are multiple forms of CTLA-4, and that this can vary between strains of mice or humans.

A recent study has shown that Treg cells grow extensively in vivo (Tang, *J. Immunol.* 171:3348 (2003)), while others have suggested that the efficacy of therapeutic cancer vaccination in mice can be enhanced by removing $CD4^+CD25^+$ T cells (Sutmuller et al., *J. Exp. Med.* 194:823-832 (2001)). Studies have also indicated that depletion of regulatory cells led to increased tumor-specific immune responses and eradication of tumors in otherwise non-responding animals (Onizuka et al., *Cancer Res.* 59:3128-3133 (1999); Shimizu et al., *J. Immunol.* 163:5211-5218 (1999)). Susceptible mouse strains that were made $CD4^+CD25^+$ deficient by neonatal thymectomy were shown to develop a wide spectrum of organ-specific autoimmunities that could be prevented by an infusion of $CD4^+CD25^+$ T cells by 10-14 days of age (Suri-Payer et al., *J. Immunol.* 160:1212-1218 (1998)). That study also found that $CD4^+CD25^+$ T cells could inhibit autoimmunity induced by autoantigen-specific T cell clones. The transfer of $CD4^+CD25^-$ T cells into nude mice also reportedly led to the development of autoimmune disorders which could be prevented by the co-transfer of $CD4^+CD25^+$ T cells using lymphocytes first depleted of $CD25^+$ cells (Sakaguchi et al., *J. Immunol.* 155:1151-1164 (1995)).

However, data also indicate that the role of $CD4^+CD25^+$ cells is not limited to self-tolerance and the prevention of autoimmunity. While few studies have addressed the role of $CD4^+CD25^+$ T cells in alloresponses or in transplantation, $CD4^+CD25^+$ T cells have been reported to prevent allograft rejection, both in vitro and in vivo (Hara et al., *J. Immunol.* 166:3789-3796 (2001); Taylor et al., *J. Exp. Med.* 193:1311-1318 (2001)). Allogeneic stimulation of human T cell proliferation is also blocked by $CD4^+CD25^+$ T cells (Yamagiwa et al., 2001), whereas Wood's laboratory has shown that $CD4^+CD25^+$ T cells suppress mixed lymphocyte responses (MLR), but only when the alloantigen was presented by the indirect, and not the direct, pathway of allorecognition (Hara et al., 2001). It is likely that direct antigen presentation occurs between the regulatory T cells and the anti-CD3/28 stimulated responder T cells, as the sorted $CD4^+25^+$ cells are highly depleted of professional APC.

The inventors have shown that $CD4^+CD25^+$ T cells exist in high proportions in the tumor infiltrating lymphocytes of patients with non-small cell lung cancer (NSCLC) (Woo et al., *Cancer Res.* 61:4766-4772 (2001)), and that $CD4^+CD25^+$ cells were an essential requirement for the ex vivo induction of tolerance to alloantigen via co-stimulatory blockade (Taylor et al., *J. Exp. Med.* 193:1311-1318 (2001)). Most of the literature states, however, that the immune system is in a state of ignorance to peripheral solid tumors, thus it is anergic (Ochsenbein, et al., *Nature* 411:1058-1064 (2001); Staveley-O'Carroll et al., *Proc. Natl. Acad. Sci. USA* 95:1178-1183 (1998)). The explanation for the differential ability of the $CD4^+CD25^+$ T cells to suppress autologous and allogeneic T cell proliferation is most likely complex. As a result, the role of $CD4^+CD25^+$ T cells in human tumors or any effect that they may have in preventing the host from mounting an immune response to autoantigens, such as tumor antigens, has to date remained unknown.

Treg are have been described in the literature as being hypoproliferative in vitro (Sakaguchi, *Ann. Rev. Immunol.* 22:531 (2004)). Trenado et al. provided the first evaluation of the therapeutic efficacy of ex vivo activated and expanded $CD4^+CD25^+$ regulatory cells in an in vivo animal model of disease (Trenado et al., *J. Clin. Invest.* 112(11):1688-1696 (2002)). In that situation, the infusion of ex vivo activated and expanded donor $CD4^+CD25^+$ cells was shown to significantly inhibit, rapidly-lethal GVHD, however, these data are presented only for mice—not in humans. Moreover, in the murine studies for the conditions tested, although the freshly isolated or cultured Treg cells have been able to suppress GVHD, graft-versus-leukemia effects (GVL activity) was allowed (Trenado et al., 2002; Jones et al., *Biol. Blood Marrow Transplant* 9(4):243-256 (2003); Edinger et al., *Nat. Med.* 9(9):1144-1150 (2003)), as was immune reconstitution (Trenado et al., 2002).

However, human blood is quite different in composition from that of a mouse, meaning that without extensive experimentation, the murine studies cannot be translated into equivalent responses in human cells. Human blood contains memory cells (~50%), which may be CD25 dim and overlap with the $CD4^+CD25^+$ suppressor cell population, making human Treg cells very difficult to purify. By comparison, the CD25 dim cells are only minimally present in rodents, or completely absent from young pathogen free mice (the condition utilized in most murine studies). In humans, purification of Treg based on CD25-selection (the only known surface marker of circulating suppressor cells, since CTLA-4 is not on the surface of fresh cells) results in enrichment of Treg cells, but it is not sufficient for full purification. Partially pure suppressor populations may briefly evidence suppression following short-term culture/activation, but these are quickly overgrown by the contaminating conventional T cells.

As a result, findings comparable to those of Trenado et al. have never been reported for human cells. Those published reports that do show proliferation of $CD4^+CD25^+$ cells, fail to find suppressor function, and until the present invention, no one has been able to obtain extensive in vitro or ex vivo expansion of human Treg cells, while at the same time maintaining GMP conditions. Only one prior publication describes the expansion of human $CD4^+CD25^+$ cells (Levings et al., 2001). Yet, in this paper, only one figure is shown of suppressor function, and it is shown to have only a modest effect. With a 1:1 ratio of suppressor cells to responder cells, only approximately 60%-65% inhibition of proliferation was noted, which is less than that which is typically observed with mouse Treg cells. Thus, the reported suppression was of such a small magnitude, that is could have resulted from non-specific effects (e.g., growth factor consumption, overcrowding, displacement from antigen presenting cells etc). Moreover, the culture was maintained by Levings et al. for only a short term (only 14 days), and the cells most likely represent a mixed culture of regulatory cells and conventional T cells.

To culture the Treg cells, Leavings et al. used JY lymphoblastoid cells (EBV virally transformed lymphoblastoid cell line) cultured with soluble anti-CD3 (1 μg/ml), in the presence of a feeder cell mixture of allogeneic PBMCs. Purification of the $CD4^+CD25^+$ cells was reported by the authors using a two stage magnetic microbead protocol, wherein first the cells were depleted of non-T cells and CD8 type of T cells using antibodies to CD8, CD11b, CD16, CD19, CD36, and CD56, which makes the resulting product unsuitable for therapeutic use in humans. Then, the cells were selected for CD25 positivity.

Yet, while Leavings et al. reported 90% purity of the Treg cells, no disclosure was made regarding stringency. This is problematic, since a very high level of stringency is absolutely critical for the isolation of human cells of sufficient purity ($CD25^+$) for suppressor cell line generation, a finding that until the present invention, has neither been discussed nor appreciated in the prior art. However, as will be shown below, the inadequacy of isolation and expansion methods used by others for the generation of the suppressor cell lines, has significantly interfered with advances in the research on human Treg cells. Consequently, it has not been possible to previously use Treg cells effectively for therapeutic purposes.

Thus, there has been a need for methods of producing sufficient number of these Treg cells to permit characterization and to provide for safe and effective therapeutic use in human patients. There has also remained a need for a greater understanding of the $CD4^+CD25^+$ T cells and their function in tumor immuno-surveillance and in the immunotherapy or immuno-suppression of cancers, particularly solid tumor cancers, such as lung cancer. Equally important has been a need to suppress in vivo alloresponses and autoimmune responses, such as, although not limited to, graft-vs-host disease (GVHD), and to elucidate and expand upon the role of $CD4^+CD25^+$ cellular therapy and to define methods for isolating or producing such $CD4^+CD25^+$ suppressor cells.

SUMMARY OF THE INVENTION

In light of the foregoing stated needs in the art, the present invention provides methods for manipulating and modulating a subpopulation of regulatory T cells (Treg cells), the $CD4^+CD25^+$ T cells, as an important component of cancer immunotherapy in solid cancer tumors, such as lung tumors, and for suppression, inhibition and prevention of alloresponses and auto-immune responses. The $CD4^+CD25^+$ T cells were found to mediate potent inhibition of autologous T cell proliferation; while regulatory T cells from patient tumors failed to inhibit the proliferation of allogeneic T cells and appear to induce or maintain tolerance to tumors in patients with lung cancer. Consequently, it is an object to provide methods to modify and regulate the development of Treg cells in vivo that could lead to a failure of tumor immunosurveillance or to enhanced tumor growth.

In addition, the data presented here indicate that $CD4^+CD25^+$ cells play an important role in alloresponses in vivo, specifically graft-vs-host disease (GVHD) generation. Ex vivo depletion of $CD4^+CD25^+$ cells from the donor T cell inoculum or in vivo CD25-depletion of the recipient pre-transplant resulted in increased GVHD responses. These findings were observed irrespective of the strain combinations or total body irradiation (TBI) conditioning regime, and regardless of whether GVHD was mediated by $CD4^+$ T cells, or by both $CD4^+$ and $CD8^+$ T cells.

Consequently, it is an object of this invention to also provide methods to promote engraftment of human transplanted tissue, including whole or selected populations of blood or bone marrow transplants, particularly by suppressing, inhibiting, blocking or preventing GVHD by means of a population of activated and ex vivo culture enhanced Treg cells administered in vivo. Advantageously such methods are further achieved with reduced intensity regimens and little or no immune suppression. Such engraftment promotion effects can thus be applied to solid organ transplant patients as a means of achieving drug-free tolerance with reduced or no conditioning regimen requirements, or to allogeneic bone marrow or autoimmune patients with autologous or allogeneic bone marrow, as means of resetting the immune system.

It is also an object of the present invention to provide a method for the ex vivo treatment of $CD4^+CD25^+$ regulatory T cells, so that the activated and culture-expanded cells may be infused into the host to produce an immunotherapeutic response. In its simplest form, the invention provides preferred, ex vivo, long-term, culture-expanding methods for human $CD4^+CD25^+$ regulatory cells, while maintaining enhanced suppressive activity, comprising: a) obtaining regulatory T cells from the patient or an allogeneic donor; b) isolating a population of $CD4^+CD25^+$ Treg cells by stringent microbead purification from the obtained cells, followed by c) activating and long-term culture-enhancing the cultured $CD4^+CD25^+$ cell, thereby increasing the number of modified $CD4^+CD25^+$ suppressor cells in the culture.

The preferred cell isolation method was designed to be highly stringent for $CD25^+$ cell isolation, once the inventors determined that the CD25 dim cells are not suppressors. As a result, the CD25 dim cells must be carefully selected out. Thus, a very high level of stringency is absolutely critical for isolation of cells of sufficient purity ($CD25^+$) for suppressor cell line generation because the CD25 dim cells can grow faster than the $CD25^+$ cells, and if included in starting populations will overgrow the $CD25^+$ cells and preclude manifestation of the suppressor function. Absent a stringent methodology, it is not possible to isolate suppressor populations that are pure enough for potent suppression, and for long term growth.

Advantageously, the disclosed purification process enables evaluation of subsets of CD25 cells. The CD45RA subset, a minor subset comprising only ~15% of $CD25^+$ cells, seems to contain the majority of suppressor cells capable of forming a cell line. This novel finding in the present invention has enabled the generation of suppressor cells lines in all donors tested (12/12), whereas previous protocols in the art have demonstrated a consistent 10-20% failure rate (even with extremely stringent CD25 purification and/or lineage depletion).

As an alternative to selective purification alone, a selective culture methodology also enables potent suppressor cell line generation. Accordingly, the invention further provides a preferred ex vivo, long-term, human $CD4^+CD25^+$ cell-culture-expanding method for producing therapeutic human Treg cells with enhanced suppressive activity. This method is preferably, but not necessarily used in conjunction with the highly stringent isolation technology. The unique culture-expanding method comprises a second-generation lineage depletion protocol using two steps and a cleavable microbead. Special cell-sized beads (magnetic iron-dextran beads-Dynabeads) are used that are coated with antibodies to CD3 and CD28. The anti-CD28 provides critical signals for augmented activation and growth of the hypo-proliferative Treg cells. Quite surprisingly, the inventors discovered that different ratios of CD3/CD28 have some selective culture effects. $CD4^+CD25^+$ cell lines grown with the beads with low ratio (low anti-CD3 compared to anti-CD28) are much more stable, and less likely to be overgrown with conventional T cells. The beads can easily be removed by passing the cultured cells through a magnetic column. Cell sorting is not required. As embodied, the preferred method also uses autologous $CD4^+$ T cells as feeders. Thus, there is no need for transformed tumor lines to facilitate growth.

Moreover, the cell lines produced by the preferred methods are uniform, as evidenced by flow cytometric characterization of phenotype, and they can be cultured for 2 months or more. As an added advantage, the culture-expanded cells retain potent functional suppressor activity (>95% inhibition, even with dilution to a 1:10 ratio of suppressor cell to responder cell, which rules out potential non-specific causes for suppression). Titration experiments reveal that the resulting suppressor cells can be titered to a ratio as low 1:16 ("suppressor: esponder ratio"), and still achieve 90% suppression.

When assayed, the culture-expanded human suppressor cells of the present invention are capable of 95% suppression of an MLR, either with fresh $CD4^+$ cells or cultured $CD4^+$ $CD25^-$ cells as responding T cells. Moreover, these CD25 dim interfering cells are $CD45RO^+$ memory cells (explaining their absence in young pathogen free mice). By the use of a CD45RA (naïve cell marker) it is possible to isolate a clean population of $CD4^+CD25^+CD45RA^+$ cells, which uniformly form potent suppressor cell lines, >90% donors (n=20). Moreover, functional data shows the blockade of responder T cell activation and prevention of cytokine production by the resulting culture-expanded cells. In one embodiment the activated and expanded $CD4^+CD25^+$ cells inhibit the autologous proliferation of peripheral blood cells. In another embodiment, the activated and expanded $CD4^+CD25^+$ cells block or prevent GVHD, or inhibit or reverse the disease if already in progress. In yet another embodiment, the activated and enhanced cells are introduced into a different host; whereas in yet another embodiment, the cells are established as a cell line for continuous therapeutic use.

Moreover, culture-expansion methods are also provided using alternative expansion strategies that do not necessarily rely upon feeder cells, such as by the use of anti-CD3/28 beads+IL-2. Moreover culture-expansion can be accomplished with or without host APCs and/or DCs when such alternative methods as anti-CD3/28 beads+IL-2 are used.

Preferably, the host is a human host and the culture-expanded cells are human, although animals, including animal models for human disease states, are also included in this invention and therapeutic treatments of such animals are contemplated herein.

The ex vivo stimulation methods of the present invention have decided advantages. For example: 1) activation and enhancement is $CD4^+CD25^+$ cell specific; 2) stimulation in long-term culture allows for the removal of the stimulating antigens prior to reintroduction of the cells in the host; and 3) lack of systemic in vivo exposure to the activating and enhancing antigens precludes significant interference with naturally occurring or induced immunogenic responses. Moreover, success is achieved with minimal host toxicity using the ex vivo activation and enhancement techniques, and the suppressor cell composition is prepared entirely in accordance with GMP conditions, meaning that the ex vivo, culture-enhanced $CD4^+CD25^+$ cells can be quickly approved for human infusion.

For clinical application, the cell product must achieve a certain effector to target ratio in vivo in order to obtain the desired beneficial effect. In many cases, the input cells at the start of cell culture will be limiting due to the rarity of suppressive precursor cells, or to limiting amounts of clinical material. The provided methods are designed to produce on the order of $10^9$ culture-enhanced cells for clinical applications. Furthermore, in order for tissue culture process to be clinically relevant, it must be scalable to large scale and be compliant with FDA approved procedures and reagents. Accordingly, the methods of the present invention, specifically designed to meet these requirements, advantageously produce an enhanced $CD4^+CD25^+$ suppressor cell infusion that is sufficiently specific to overcome volume-associated problems that would make using naturally occurring Treg cells impossible to achieve an immunosuppressive or preventative therapeutic effect in a patient, and the methods utilize conditions that have been previously-approved for human treatment.

The culture-expanded cells produced by the present long-term, culture-expansion methods can be viewed as a reagent provided by the present invention for treating GVHD, comprising activated and enhanced (modified) $CD4^+CD25^+$ cells. Preferably, the T cells are suspended in media suitable for intravenous administration to a human transplant or cancer patient, such as a media comprising a physiological buffered solution. While not limited to any mechanism, it is believed that long-term culturing of the cells in the manner proposed results in potent subset enrichment and activation, thereby creating a sufficient population of the cells to effect therapeutic benefits to the patient.

It is yet another object of the invention to provide a method for inducing an anti-GVHD response in vivo comprising contacting host $CD4^+CD25^+$ cells with activating and/or enhancing compositions ex vivo and infusing thus activated and/or enhanced $CD4^+CD25^+$ cells into the autologous host, who has or will undergo allogeneic transplant that may produce or has already initiated GVHD response in the transplant recipient. The cells are typically hematopoietic cells, such as peripheral blood lymphocytes, spleen cells, tumor-infiltrating lymphocytes or lymph node cells.

Thus, a preferred method for human treatment as provided by the present invention comprises: a) obtaining regulatory T cells from the patient or an allogeneic donor; b) isolating a population of $CD4^+CD25^+$ cells from the obtained cells, followed by c) activating and long-term culture-enhancing the cultured $CD4^+CD25^+$ cells, wherein the culture-enhancing and activating method for creating modified $CD4^+CD25^+$ cells in a media comprise the presence of human IL-2, IL-15 or other disclosed interleukin or compound to further enhance cell proliferation, thereby increasing the number of modified $CD4^+CD25^+$ suppressor cells in the culture; and d) re-introducing at least a portion of the modified $CD4^+CD25^+$ suppressor T cells into the host patient so as to induce an in vivo therapeutic response. Such response prevents, blocks, suppresses, inhibits or reverses GVHD or other autoimmune response, or peripheral blood cell proliferation in a cancer patient.

In yet another embodiment, the method utilizes the ex vivo, long-term, culture enhanced $CD4^+CD25^+$ cells produced using the culture methods provided herein. While in still another embodiment, the method utilizes ex vivo, long-term, culture enhanced $CD4^+CD25^+$ Treg cells derived from bone marrow, using the culture methods provided herein for peripheral blood, except in this case, bone marrow aspirates would be used to acquire the Treg cell population.

It is a further object to obtain lymphocytes prior to the onset of cancer, from cancer-free hosts, and store the cells using conventional techniques until needed at the onset of disease, at which time the cells may be thawed, cultured and activated and enhanced as herein previously described for reinfusion into the host. Alternatively, an established cell line may be made from cancer-free hosts (allogeneic or autologous). The cell line can be stored as above, activated and culture-enhanced until needed. Similarly, it is an object to obtain lymphocytes prior to the allogeneic transplant from the transplant recipient, and store the cells using conventional techniques until the transplant is completed, at which time the cells may be thawed, $CD25^+$ depleted and/or culture-enhanced and activated as herein described for reinfusion into the host to block, suppress, inhibit or prevent GVHD, or to reverse GVHD if already initiated. Alternatively, an established cell line may be prepared from the host before transplant, and stored as above, or CD25+ depleted and/or culture-enhanced and activated as above, until needed.

In one embodiment, the method further comprises the step of administering human IL-2, IL-15 or other disclosed agent to the host patient in vivo after re-introducing the modified CD4+CD25+ cells. The autologously re-introduced ex vivo modified cells are thus considered to be a cellular implant. In an alternative embodiment, the host is similarly treated after modified CD4+CD25+ donor cells are allogeneically introduced into the recipient.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

FIG. 2A is a flow histogram from 2 representative patients demonstrating CTLA-4 expression in CD4+CD25− and CD4+CD25+ TIL and PBMC. FIG. 2B shows the mean (±.S.E.) percentage of cells expressing CTLA-4 in CD4+CD25− tumor infiltrating lymphocytes (left), CD4+CD25+ tumor infiltrating lymphocytes (middle), and CD4+CD25+ peripheral blood mononuclear cells (PBMC) (right) from 5 consecutive NSCLC patients.

FIGS. 3A-3B graphically shows that direct inhibition of anti-CD3 or anti-CD3/CD28 induced autologous T cell proliferation by tumor infiltrating CD4+CD25+ cells. Autologous PBL were cultured alone or with increasing numbers of sort purified CD4+CD25+ or CD4+CD25− tumor infiltrating lymphocytes (TIL) from lung cancer specimens, and the cells were stimulated with soluble or plate bound anti-CD3 (FIG. 3A) or with plastic immobilized anti-CD3/CD28 (FIG. 3B) and [³H]thymidine incorporation was measured. Results are expressed as % response of PBL cultured alone; 100% proliferation for the CD25− plot=37081±4094 cpm, and for the CD25+ plot=29465±1007 cpm.

FIGS. 4A-4D show that tumor infiltrating CD4+CD25+ cells failed to suppress T cells from allogeneic normal donors or from lung cancer patients. Allogeneic peripheral T cells from normal donor (FIG. 4A) or autologous PBL from a NSCLC patient (FIG. 4B) were cultured with the indicated numbers of tumor infiltrating CD4+CD25+ cells from the cancer patient. In FIG. 4C, peripheral blood T cells from a normal donor were cultured with autologous sort purified peripheral blood CD4+CD25+ donor T cells. In FIG. 4D, tumor infiltrating CD4+CD25+ or CD4+CD25− cells were cultured with allogeneic PBL from a NSCLC patient. All cell cultures were stimulated with plate bound anti-CD3/CD28, and [³H]thymidine incorporation was measured. Results are expressed as means of triplicate cultures (±S.E.) for one of three (FIG. 4A), two (FIG. 4B), two (FIG. 4C), or four (FIG. 4D) independent experiments, each with similar results.

FIG. 5A is an ELISA of the supernatants from cultures of CD4+CD25+ and of CD3+ cells depleted of CD4+CD25+ cells from lung cancer patients tested for TGF-β. Results are representative from 1 of 6 patients (±S.E for triplicate wells). In FIG. 5B, autologous PBL were cultured alone or with varying numbers of CD4+CD25+ cells and stimulated with plate bound anti-CD3/CD28. Anti-TGF-β neutralizing antibody was added, and [³H]thymidine incorporation was measured. Results are expressed as means of triplicate cultures (±S.E.) for one of two independent experiments with similar results.

FIGS. 6A and 6B graphically show that depletion of CD4+CD25+ cells accelerates GVHD lethality. Whole CD4+ or CD25-depleted CD4+ B6 T cells were transferred into sublethally irradiated bm12 recipients (in FIG. 6A, 1×10⁵ cells were administered per animal; in FIG. 6B 5×10⁴ cells were administered per animal). x-axis=days after transfer of cells; y-axis=proportion of recipients surviving. n=8/group FIG. 6A, p=0.024; FIG. 6B, p=0.0068.

FIGS. 15A-15D depict purification of CD4$^+$CD25$^+$ cells from peripheral blood using representative 2-color FACS plots of PBMC and purified CD4$^+$CD25$^+$ and CD4$^+$CD25$^-$ cells. FIG. 15A shows the results of an examination of peripheral blood reveals CD4$^+$CD25$^+$ cells constitute 1-3% of PBMC. There are a variable number of non-CD4+ cells that express CD25, generally of lower intensity expression (mostly B cells). FIG. 15B shows that some donors evidence a more distinct CD4+CD25+ population. FIG. 15C shows CD4$^+$CD25$^+$ cells, purified by anti-CD25-FITC and anti-FITC cleavable microbeads, and subsequently lineage depleted. Intensity of CD25-PE staining is slightly decreased by prior staining with anti-CD25-FITC. FIG. 15D shows CD4$^+$CD25$^-$ cells, purified by CD25 depletion of PBMC, followed by CD4$^+$ positive selection. Data are representative of 20 donor evaluations, and 10 cell purification experiments.

FIG. 16A shows proliferation of highly purified CD4$^+$CD25$^-$ cells (Δ) and double column-lineage negative CD4$^+$CD25$^-$ cells (■), in short term 96 well $^3$H-Thymidine incorporation assays. CD4$^+$CD25$^-$ cells markedly proliferate, while CD4$^+$CD25$^+$ cells only minimally and transiently proliferate. FIG. 16B shows augmentation of proliferation of highly purified double column-lineage negative CD4$^+$CD25$^+$ cells (■), in short term 96 well $^3$H-Thymidine incorporation assays. IL-2 at 100 IU/ml augments expansion (♦). However, irradiated CD4$^+$CD25$^-$ feeder cell supplementation (1:1 ratio) (●), provides for increased expansion, which is more sustained. Representative of 4 experiments. FIG. 16C shows long term culture accumulation of CD4$^+$CD25$^+$ cell lines. Cell lines were stimulated once with anti-CD3/anti-CD28 mAb-coated beads (□), or with immobilized anti-CD3 (■), both were supplemented with feeder cells. Cells were split and fed IL2 every 3-4 days as needed. Data reported as fold expansion of cell number, and are representative of 22 cultures for anti-CD3/CD28 mAb-coated beads, and 3 cultures for plastic-immobilized anti-CD3 mAb.

FIG. 17A shows representative cell lines derived from CD4$^+$CD25$^+$ cells (double column-lineage depletion purification) are good suppressors (●). In contrast, cell lines derived from CD25$^-$ cells (Δ) augment the MLR, versus control MLR cultures (□). Results representative of 22 experiments. FIG. 17B shows fresh standard MACS purified CD4$^+$CD25$^+$ cells (♦), added to MLR, compared with a representative weakly suppressive CD4$^+$CD25$^+$ cell line (●), versus control MLR (□). Results representative of 4 experiments. FIG. 17C shows that MLR reaction was nearly completely blocked by addition of potently suppressive cultured CD4$^+$CD25$^+$ cells (●), versus control MLR (□). Representative of 7 potent suppressor cell lines, tested in 14 MLR.

FIG. 18A-18K presents flow cytometric comparisons of CD25$^+$ versus CD25$^-$ cell lines after 3-4 weeks culture expansion. Antigen expression was profiled by FACS analysis. Shown are representative plots of CD25$^-$ derived cell lines, compared with potent suppressor cell lines, and weakly suppressive cell lines. (FIGS. 18A-18C). FIG. 18A shows that cell lines derived from CD25$^-$ cells express low levels of CD25 as they revert to a more quiescent state. FIG. 18B shows that potent suppressor cell lines maintain high levels of CD25 expression. FIG. 18C shows that cell lines derived from CD4$^+$CD25$^+$ cells that have weak suppressor function express intermediate levels of CD25. (FIGS. 18D-18F). FIG. 18D shows that CD4$^+$CD25$^-$ derived cell lines express minimal intracellular CTLA4. FIG. 18E shows that potent suppressor cell lines maintain high intracellular expression of CTLA4. FIG. 18F shows that weak suppressor lines express intermediate levels. (FIG. 18G-18I). FIG. 18G shows that CD25$^-$ derived cell lines express variable levels of CD62L and diminished CD27. FIG. 18H shows that potent suppressor cell lines contain a higher percentage of cells that express both. CD62L and CD27. FIG. 18I shows that weak suppressor cell lines contain a lower percentage of cells that express CD62L and CD27. FIGS. 18J-18K show cell sorting of suppressor cell line subsets reveals potent suppressor cells to express CD62L and CD27. FIG. 18J is a FACS plot showing sorting gates for CD62L and CD27 subsets. FIG. 18K presents a functional analysis in MLR, reveals suppressor activity solely within the CD62L and CD27 double positive subset (striped bar). Control MLR cultures (gray bar) and suppressed MLR (dark bar). As shown, the CD62L$^+$/CD27$^-$ subset (brick bar), and the CD62L$^-$/CD27$^-$ subset (weaved bar) both augment the MLR.

FIGS. 19A-19D graphically depict that cultured CD4$^+$CD25$^+$ cells consistently and markedly suppress MLR proliferation and cytokine secretion. Potent CD25$^+$ suppressor cell lines were tested in multiple MLR from various unrelated donors. FIG. 19A shows 8 separate MLR displaying variance of control and suppressed proliferation. In most all donor combinations it was markedly impaired. Control MLR cultures (gray bars) and suppressed MLR (dark bars). Results are representative of over 20 experiments with 7 different potent suppressor cell lines. FIG. 19B shows the effect when graded numbers of potent cultured suppressor cells were added to MLR reaction to determine the minimum number needed for inhibition. Up to a 1:16 dilution (roughly 3,125 suppressors), still markedly impaired MLR when using the most potent of the suppressor cell lines. Three plots are shown, representative of 6 potent suppressor cell lines. FIG. 19C presents a daily assessment of IL-2 levels in culture supernatant, revealing a profound block in IL2 accumulation in suppressed MLR cultures (●), versus control MLR cultures (□). Representative of 4 MLR analyses. FIG. 19D presents an assessment of other cytokines produced by activated T cells, revealing profound impairment of accumulation. Significant levels of TNF-α, TFN-γ, GM-CSF, IL-6 or IL-10 are not produced. Shown are levels on day 6, peak of accumulation in control MLR cultures (light bars), versus suppressed MLR cultures (dark bars). Representative of 4 MLR analyses.

FIG. 20A-20G show that cultured Treg cells impair the activation of responding T cells, and can suppress MLR driven by mature DC. MLR were evaluated for expression of activation antigens after one day of culture. Shown are control MLR stained for CD69 in FIG. 20A, CD25 in FIG. 20B, and OX40 (CD134) in FIG. 20C. In suppressed MLR responding T cells were first gated on HLA-A2 to distinguish them from the HLA-A2 negative suppressor cells. Separately shown are responder cells from suppressed MLR stained for CD69 in FIG. 20D, CD25 in FIG. 20E, and OX40 (CD134) in FIG. 20F. Results are representative of 3 experiments. FIG. 20G shows the maturation of DCs, prior to MLR, by LPS or TNF/polyIC combination, or that inclusion of these stimulating factors in MLR fails to bypass suppression. Control MLR cultures (gray bars) and suppressed MLR (dark bars).

FIG. 21A-21D graphically depicts the results of a functional analysis of suppression in MLR. FIG. 21A shows that suppressor cell lines lack significant cytotoxicity for DC in chromium release assays (●). Control lysis mediated by NK cell line NK92 (□). FIG. 21B shows that suppressor cell lines lack natural killer (NK) or lymphokine activated killing (LAK) type activity and show no lytic activity against K562 in chromium release assays (●). Control lysis mediated by NK cell line NK92 (□). 5,000 labeled targets were used in both FIGS. 21A and 21B, with up to a 20:1 effector/target ratio in each. FIG. 21C shows in MLR assays, that using neutralizing antibodies to immunosuppressive factors IL-10, and to TGF-β, as well as anti-IL-10R, or combinations of all three—each failed to reverse the suppression mediated by the cultured suppressor cell lines. FIG. 21D shows that the potent suppressor cell lines have minimal inhibitory activity added to MLR driven by DCs that are autologous to the suppressor (and allogeneic to the responder). Suppressor cell line Ts-A (cross-hatched bars) was used to suppress MLR cultures driven by DC-A (from the same donor as the suppressor) or by DC-B (from a different donor from suppressor). Suppressor cell line Ts-B (checkered bars), was also tested against DC-A and DC-B. Representative of 4 experiments.

DESCRIPTION OF PREFERRED EMBODIMENTS OF THE INVENTION

Figure 1:
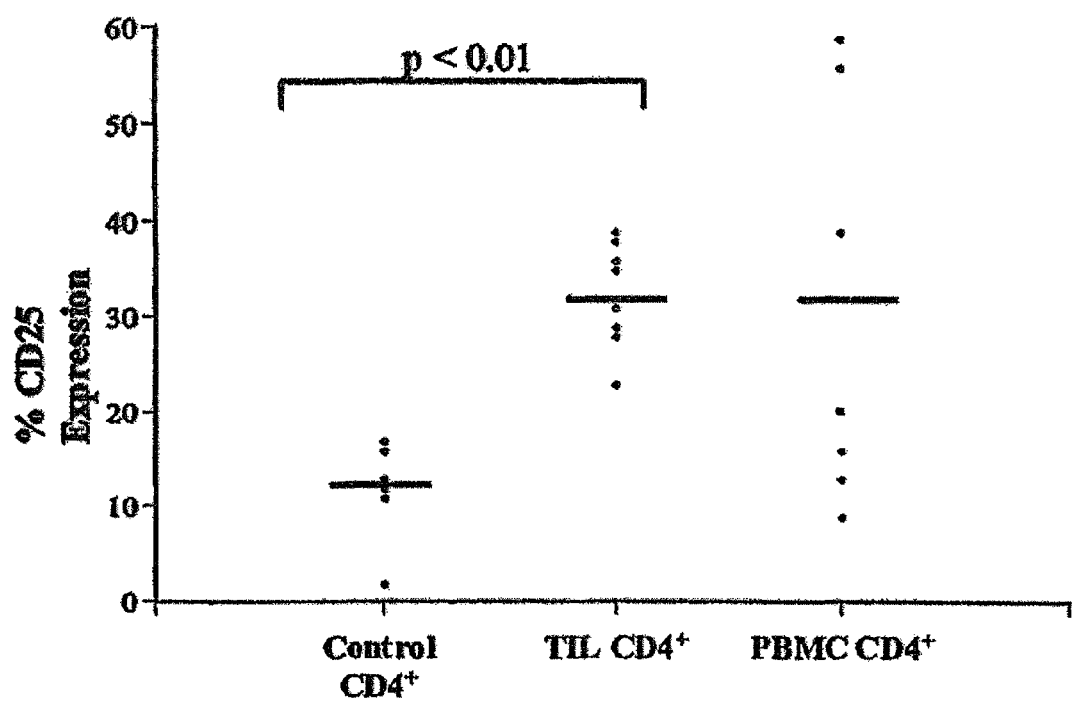
FIG. 1 graphically display the frequency (%) of CD4+CD25+ lymphocytes present in total CD4+ cells isolated from lung cancer tumor specimens as compared with the peripheral blood lymphocytes (PBL) of lung cancer patients as determined by flow cytometry. Distributions and means are shown: PBL of normal donors, n=7 [left]; unstimulated tumor infiltrating lymphocytes (TIL) from patients with NSCLC, n=8 [center]; or unstimulated PBL from patients with NSCLC, n=9 [right]. P values were calculated using the Student 2-tailed t test.

In the present invention, primary lung tumor specimens from patients with early stage lung cancer were found to harbor large numbers of T cells with the phenotype previously ascribed to regulatory T cells ("Treg cells"). In contrast to previous descriptions of regulatory T cells, the CD4$^+$CD25$^+$ lymphocytes in tumors have strikingly high surface expression of CTLA-4, and they directly inhibit proliferation of autologous, but not allogeneic, T cells. This suppressive effect of the tumor resident CD4$^+$CD25$^+$ T cells was potent, and occurred even after vigorous activation of the responding T cells, establishing a strong correlation between Treg cells and suppression of the activation and response of cytotoxic cells. Thus, the present invention provides methods for ex vivo activating and specifically long term culturing and enhancing the Treg cells, the activated and enhanced Treg cells themselves, and methods for using the activated and enhanced Treg cells in immunotherapy and for the suppression of autoimmune responses, including GVHD.

As used herein, "allogeneic cells" (allogenicity) are those isolated from one individual (the donor) and infused into another (the recipient or host); whereas "autologous cells" (autology) refer to those cells that are isolated and infused back into the same individual (recipient or host). Accordingly, allogeneic T cell proliferation is stimulated by antigen presenting cells ("APC") from another individual, while autologous T cell proliferation is stimulated by self-APCs. Unless specified, the APC in the present invention can, therefore, be of any type known in the art.

"Antigens" are entities that initiate immune responses. "Alloantigens" refer to agents that cause the immune system of one individual to recognize and destroy the cells of another individual when the two are mixed together. "Mitogens" are agents that induce all T cells to proliferate in an antigen non-specific manner.

"Mixed lymphocyte reaction," "mixed lymphocyte culture," "MLR," and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes, which in this particular invention are Treg cells. A frequent objective of an MLC is to provide allogeneic stimulation, such as may initiate proliferation of the Treg cells; but unless indicated, proliferation during the culture is not required. In the proper context, these terms may alternatively refer to a mixture of cells derived from such a culture. When cells from an MLC are administered as a bolus to a human, it is referred to as a "cellular implant."

Although CD4$^+$CD25$^+$ immune regulatory cells are important regulators of in vivo homeostasis and are required for the prevention of autoimmunity, the role of these professional suppressor cells in alloresponses has been less well studied. Based on findings that Treg cells suppress activation of cytotoxic T cells, a preferred embodiment of the present invention actually utilizes the professional suppressor cells to regulate T-cell responses to alloantigen and to investigate the generation of graft-vs-host disease (GVHD). This is demonstrated by the acceleration of GVHD and/or by the increase in lethality that occurred in the present embodiment, wherein CD25$^+$ cells were depleted ex vivo from the donor T cell inoculum or the recipient was conditioned in vivo by the pre-transplant administration of an anti-CD25 monoclonal antibody (mAb) infusion. Depletion of CD25$^+$ cells resulted in an increase in GVHD regardless of whether donor anti-host responses were mediated by CD4$^+$ T cells or both CD4$^+$ and CD8$^+$ T cells.

This is consistent with data by others (e.g., Piccirillo et al., *J. Immunol.* 167:1137-1140 (2001); Gao et al., *Transplantation* 68:1891-1897 (1999)). Additionally, CD25$^+$ cell depletion was found to accelerate GVHD in several strain combinations, irrespective of intensity of conditioning, indicating that even in a high proinflammatory cytokine milieu, CD25$^+$ cells were functioning as suppressors of alloresponses. Thus, the depletion data in the present invention indicated the role of CD25$^+$ cells in inhibition of alloresponses, and showed that the infusion of CD25$^+$ cells could prevent or ameliorate GVHD, whereas previous data indicated that fresh naïve CD4$^+$CD25$^+$ cells did not mediate GVHD lethality alone and had only a modest protective effect when infused with GVHD-inducing T cells at a 1:1 ratio (Taylor et al., 2001).

While there are two populations of CD25 positive cells, CD25$^+$ cells in general constitute 5-10% of the total CD4$^+$ T cell population in all human peripheral blood mononuclear cells (PBMCs). However, only 1-2% of the CD25$^+$ cells express very high levels of CD25 and are thought to be the bona fide Treg cells, or at minimum Tregs with enhanced function. As a result, it would be difficult to infuse sufficient numbers of purified regulatory cells to be of significant therapeutic benefit.

Data by Thornton and Shevach, using APCs coupled with anti-CD3 and IL-2 to activate Treg cells, indicated that in mice, $CD4^+CD25^+$ cells could become more potent suppressor cells upon ex vivo activation (Thornton et al., *J Immunol.* 164:183-190 (2000)). Unfortunately, the Thornton infusion offers no therapeutic benefit for humans since the method would not be FDA approvable, nor did it teach any way to expand the cells. As previously noted, mouse T cell growth is significantly different from human T cell growth requirements (see Mestas, *J. Immunol.* 172: 2731 (2004)). Moreover, while anti-CD40L (CD154) or anti-B7 (anti-CD80 and CD86) mAbs completely blocked an in vitro response, neither effectively prevented GVHD in vivo.

Interestingly, one highly effective earlier method utilized anti-CD3/28 beads (Takahashi et al., *Int. Immunol.* 10:1969-80 (1998)), but Takahashi teaches that the inclusion of soluble anti-CD28 mAb with anti-CD3 mAb blocks suppression. $CD4^+CD25^+$ cells have been shown to be non-responsive in vitro to multiple stimuli—except anti-CD3+IL-2. However, non-responsive cells that undergo vigorous expansion become responsive. Therefore, the literature suggests that robust expansion would occur at the expense of retention of suppressor cell activity, and only low levels of expansion were reported. Thus, the present methods would not have been predicted by the prior art to be able to expand $CD4^+CD25^+$ cells without loss of suppressive activity, and would not have been predicted to provide such robust expansion as is shown in the present invention with an increase of suppressor cell function.

However, recognizing the need for an effective therapeutic method for treating patients to suppress and prevent GVHD, the present invention utilizes a GMP compliant culture system to both activate and expand the Treg cells. A preferred embodiment of the present invention uses anti-CD3/28 mAb coated beads in combination with IL-2 and irradiated feeder cells to induce both (i) robust expansion by >100-fold and (ii) an increase in suppressor cell activity. Moreover, the robust expansion rates disclosed herein are associated with more potent suppressor cell activity than was previously reported in the literature (see Godfrey et al., *Blood in press* 2004, epub on line, Mar. 18, 2004).

A "cell line" or "cell culture" denotes higher eukaryotic cells grown or maintained in vitro. It is understood that the descendants of a cell may not be completely identical (either morphologically, genotypically, or phenotypically) to the parent cell. Initial studies in mouse models of bone marrow transplantation (BMT) have shown that $CD4^+CD25^+$ cells can prevent GVHD across major histocompatibility (MHC) barriers (Taylor et al., *Blood* 99(10):3493-3499 (2002), Hoffman et al., *J. Exp. Med.* 196(3):389-399 (2002), Cohen et al., *J. Exp. Med.* 196(3):401-406 (2002)). However, the present embodiments demonstrate that $CD4^+CD25^+$ cells can be expanded to an even greater degree with longer culture duration ("long term") than was previously possible. Therefore, the preferred embodiments of the present invention describe "long-term, culture expanded" $CD4^+CD25^+$ cells or Treg cells or $CD25^+$ cells.

By "long term" is meant a culture period lasting more than 1 week, preferably $\geq$10 days, more preferably $\geq$2 weeks, more preferably $\geq$3-4 weeks, more preferably $\geq$1 month, more preferably $\geq$6-8 weeks, more preferably $\geq$2 months, more preferably $\geq$3 months, more preferably $\geq$6 months, and most preferably 1 year or longer—so long as some level of cellular function, specifically suppressor activity is retained. Accordingly, data presented in the present invention indicate that, although different ex vivo activation protocols led to varying recoveries or expansion of $CD4^+CD25^+$ cells, all of the protocols resulted in cells that significantly suppressed or inhibited GVHD.

The ex vivo activation protocols investigated in these studies are intended to be exemplary to the practitioner, and to provide evidence of the effectiveness of the principle. The provided protocols were, however, never meant to be an exhaustive list of potential strategies for expansion and activation, since there are already many known methods of treating blood ex vivo that could be applied, e.g., those used in U.S. Pat. Nos. 6,251,385; 6,203,787; 6,051,227; 5,962,318; 5,728,388; 5,472,867; 5,399,493, while newer methods remain to be discovered that will permit improvements to the principles taught herein.

As used herein, "treatment" or "therapy" refers to clinical intervention in an attempt to alter the natural course of the individual or cell being treated, and may be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, preventing metastasis, lowering the rate of disease progression, ameliorating or palliating the disease state, and causing remission or improved prognosis. The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An "immunogenic amount" is an amount shown in the subject group being treated or tested (either diseased or not) that is sufficient to elicit an immunological response, which may comprise either a humoral response, a cellular response, or both. Preferably in accordance with the present invention, suppression is achieved at >30% over that which would occur absent practice of the culture-expansion methods disclosed herein. More preferably, the suppression achieved is $\geq$40%, more preferably at $\geq$50%, more preferably at $\geq$70%, more preferably at >85%, more preferably at $\geq$90%, more preferably at $\geq$95%, more preferably at $\geq$99, and most preferably at $\geq$100%, so long as the ex vivo culture of the cells is sustainable long term.

The terms "suppression," "inhibition" and "prevention" are used herein in accordance with accepted definitions, i.e., "suppression" results when an ongoing immune response is blocked or significantly reduced as compared with the level of immune response that results absent treatment by the present invention. Similarly, "inhibition" refers to blocking the occurrence of an immune response or significantly reduces such response as compared with the level of immune response that results absent treatment by the present invention. When administered prophylacticly, such blockage may be complete so that no targeted immune response occurs, typically referred to as a "prevention" with regard to completely blocking the immune response before onset; or in the present invention, the treatment may advantageously reduce the effect as compared to the normal untreated state, typically referred to as suppression or inhibition.

In terms of clinical response for subjects bearing a neoplastic disease, an effective amount is amount sufficient to palliate, ameliorate, stabilize, reverse or slow progression of the disease, or otherwise reduce pathological consequences of the disease. Similarly, in transplant patients experiencing the onset of GVHD, or those that are susceptible to GVHD, an effective amount is that amount which is sufficient to block or prevent its onset; or if GVHD pathology has begun, to palliate, ameliorate, stabilize, reverse or slow progression of the disease, or otherwise reduce pathological consequences of the disease. In any case, an effective amount may be given in single or divided doses. Preferred quantities and cell ratios for use in an effective amount are given elsewhere in this disclosure.

As $CD4^+CD25^+$ immune regulatory cells are a very heterogeneous population, it seems likely that different methods of activation and expansion may result in distinct populations of cells with potentially different suppressor/effector function. The heterogeneity of $CD4^+CD25^+$ immune regulatory still being elucidated. Currently they can subdivided into two major classes Adaptive and Natural. These cell types have been defined by Bluestone et al., 2003, supra, and are summarize in the following table (Table 1)

TABLE 1

| A comparison of natural and adaptive regulatory cells. | | |
|---|---|---|
| Feature | Natural Treg cells | Adaptive Treg cells |
| Site of induction | thymus | Periphery |
| CD28-CD80/CD66 dependent | yes | No |
| IL-2 dependent | yes | Yes |
| CD25 expression | yes (high) | Variable |
| Specificity | Self-antigens in thymus | Tissue-specific antigens and foreign antigens |
| Mechanism of effector cell suppression | T-cell-T-cell/APC contact; cytokine dependent | T-cell-T-cell/APC contact; cytokine dependent |

For example, some types of T regulatory cells are dependent upon exogenous TGF-β or a combination of IL-10 and TGF-β for propagation and generation of suppressor cell activity, whereas the cell populations of the present invention are not dependent upon such exogenous growth factors. This point out another difference between human $CD4^+CD25^+$ cells and animal model (murine) counterparts. Mouse cells produce less TGF-β than that which is produced by human Treg cells, as shown in IL-10 studies. This adds an unaccounted for variable in the reported findings resulting from the use of cultured murine cells because fetal calf sera lots, etc contain various levels of TGF-β.

Because anti-CD3/28 beads+IL-2 appears to expand all $CD4^+CD25^+$ subpopulations, an advantage of the present invention is that $CD4^+CD25^+$ cells can be expanded from the heterogeneous population or subsets of the $CD4^+CD25^+$ cells with more potent function. Such has been the case for $CD4^+CD25^+$ cells that express high levels of L-selectin, a homing receptor, that has recently been found to be a more potent suppressor of GVHD than the subset expressing low levels of L-selectin (CD62L) (see examples that follow).

Human $CD4^+CD25^+$ cell culture and enhancement. Initial means of generating suppressor cell cultures included immobilized anti-CD3 plus IL-2 and TGF-β for culture (see, e.g., Kung et al., Science 206(4416):347-349 regarding CD3 antibody clone OKT3). Cells were grown in plastic plates which had anti-CD3 pre-immobilized onto the plate at various concentrations, with 1-5 μg/ml (immobilization concentration) being optimal. Early on, as described in the Examples that follow, it was evident to the inventors that TGF-β was not required for function (FIG. 5), but it did seem to augment suppressor ability slightly. As conditions are varied, the need/benefit for TGF-β may, however, change. For example, using CD62L (L-selectin hi) cells as described in the Examples, TGF-β may not be needed since the latter are more potent suppressors of GVHD than non-fractionated $CD4^+25^+$ cells.

The use of anti-CD3/anti-CD28 beads induced robust proliferation of suppressor cells, having the effect of plastic-bound antibody. CD28 stimulation also enhances the activation of Treg cells and a present embodiment shows that beads coated with anti-CD3 and anti-CD28 (anti-CD3/CD28) antibody mixed with Treg cells at a 1:10 ratio optimal expands and preserves Treg function. CD28 is a disulfide bonded homodimer, expressed on the surface of the majority of T cells (June et al., Immunol Today 11:211 (1990)). CD28 can be identified by a number of commercially available CD28 monoclonal antibodies, as would be known to one of skill in the art.

Figure 11:
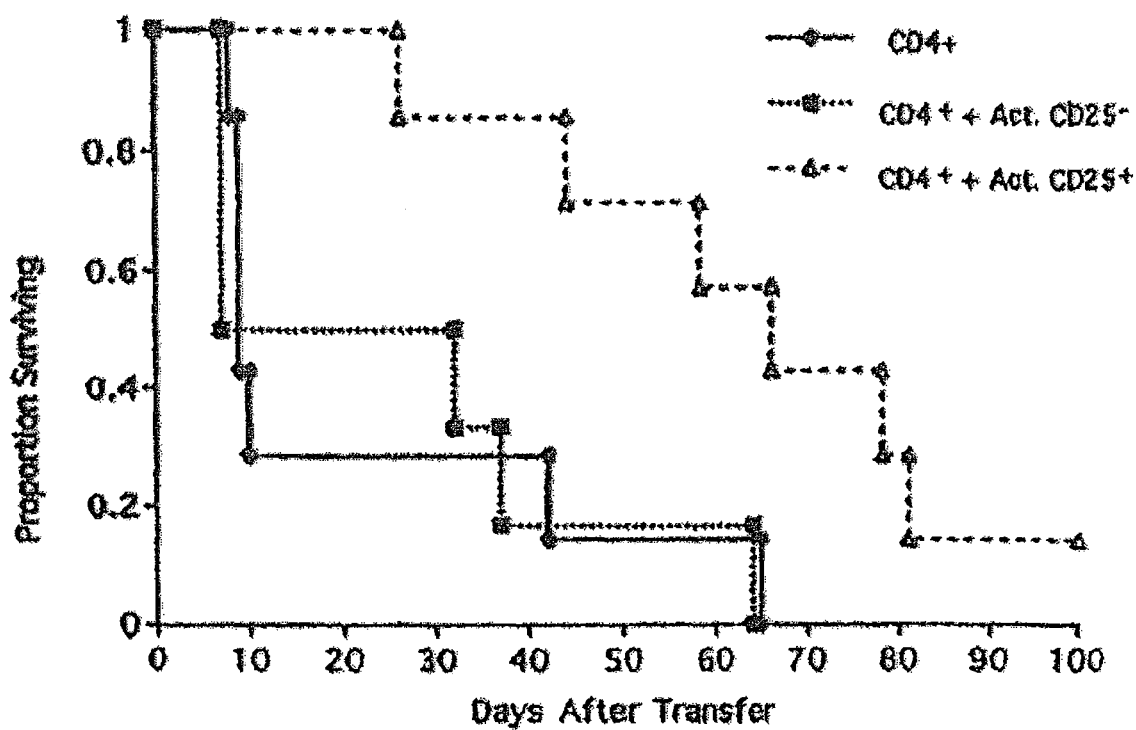
FIG. 11 graphically shows that ex vivo expanded and activated CD25+ cells inhibit GVHD. Naïve B6 CD4+ T cells were infused into non-irradiated, NK-depleted BALB/c SCID recipients. Cohorts of mice received a separate injection of activated CD4+CD25+ cells or CD4+CD25− cells. Cells were activated and expanded by immobilized anti-CD3 mAb and high dose IL-2. x-axis=days after transfer of cells. y-axis=proportion of recipients surviving. n 8/group; p=0.022 for CD4+ vs CD4++CD25+.
Figure 12:
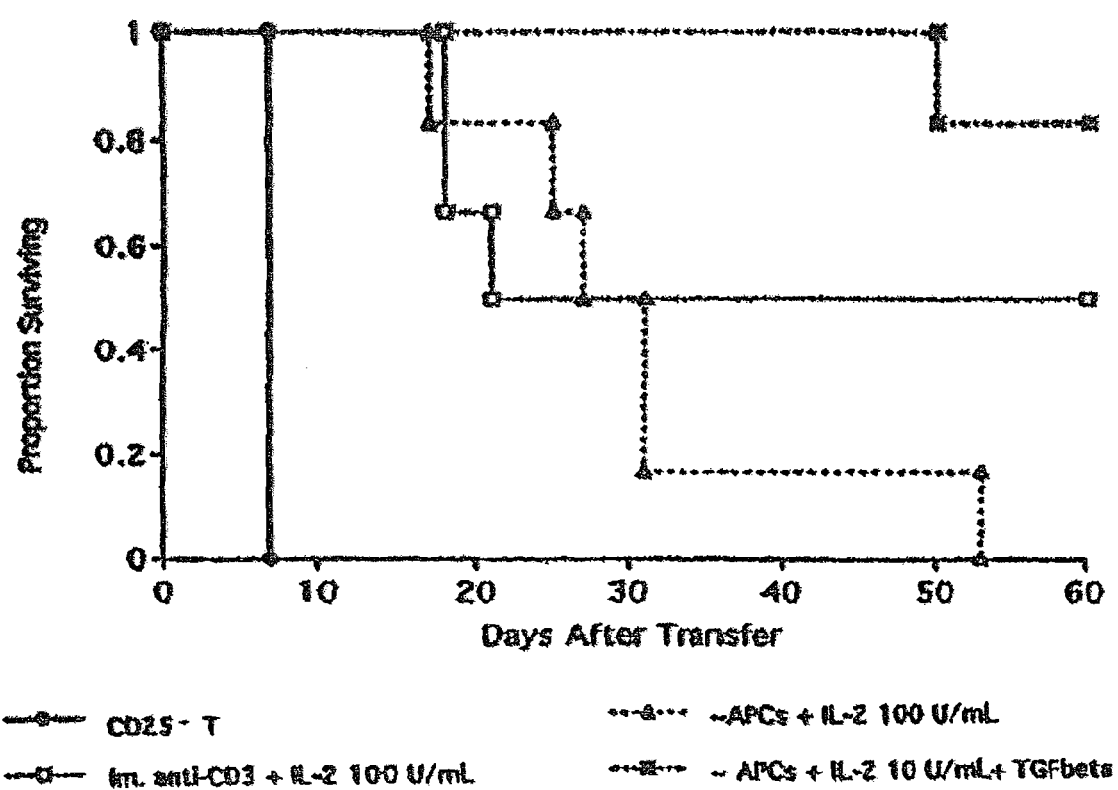
FIG. 12 graphically shows that CD25$^+$ cells cultured under different conditions inhibit GVHD. CD25-depleted (CD25$^-$) B6 T cells were infused into non-irradiated, NK-depleted BALB/c SCID recipients. A second group of mice received a separate injection of CD25$^+$ cells expanded as in FIG. 11, with immobilized anti-CD3 mAb and high dose IL-2 (open boxes). A third group of mice received a separate injection of CD25$^+$ cells cultured with irradiated BALB/c splenocytes and high dose IL-2 (open triangles). A fourth group of mice received a separate injection of CD25$^+$ cells cultured with irradiated BALB/c splenocytes, low dose IL-2 and TGF-β (star). x-axis=days after transfer of cells. y-axis=proportion of recipients surviving. n=6/group; all p values ≦0.016 compared to control group (closed circle).

Initial concerns that co-stimulation might abrogate suppression (as it does in short term assays) proved to be unfounded. Interestingly, an anti-CD3-only coating on the beads was a poor inducer of proliferation. In fact, the cells grew to 5- to 10-times as much as in equivalent immobilized-CD3 cultures, and they retained suppressor function. Cultures with IL-2 or IL-15 induced equivalent proliferation and suppressor function (FIGS. 11 and 12).

Once a workable system for a reasonably reproducible isolation and culture and assay of suppressor cells was developed in the present invention, it was then possible for the inventors to systematically vary parameters to identify methods for improved cell isolation and culture. By performing more stringent purification strategies, more potent and reproducible suppressor cell lines were isolated. This led to anti-CD25 microbead titration experiments (titer 1:6), and the development of a double column purification protocol, which then led to a consistent generation of potent suppressor cell lines (having ≧80% success rate). CD25 is the IL-2Rα molecule (see e.g., Waldmann, Immunol Today 14:264 (1993)), identifiable by a number of commercially-available monoclonal antibodies (Ab or mAb, as used herein) or by the binding of labeled IL-2 to CD25.

In the present invention, the CD25 Ab was used to enrich the cell population for $CD4^+CD25^+$ on the basis of their CD25 expression. Doing this prior to stimulation enhanced the ability to expand those Treg cells that had potent suppressive activities. In fact, when various ratios of anti-CD3 to anti-CD28 were tested (20:1, 5:1, 1:1, 1:5, 1:20, respectively) on the microbeads, the higher ratio anti-CD28 beads induced selective outgrowth of suppressor T cells. The 1:5 and 1:20 ratio anti-CD3/anti-CD28 beads generated cell lines that were less contaminated with non-suppressor T cells. The cell lines derived using lower amounts of anti-CD3 were more potent, and retained a much increased CD27 and CD62L expression, indicating that the naïve T cell phenotype of these cells has been maintained. These are cell surface markers commonly used to distinguish naïve versus memory T cells (see, e.g., DeRosa, Nat. Med. 7: 245 (2001)). CD27 is a receptor, which is lost on effector cell differentiation, and CD62L and CCR7 are important for cell migration to the lymphoid organs. Thus, in vivo these suppressor cells logically home normally to lymphoid organs and restrict activation and expansion of alloreactive cells at these sites, including Peyers patches critical for GVHD induction.

It has been reported, that in the human system it was necessary to isolate the CD25$^+$ bright subset of CD4$^+$CD25$^+$ cells in order to detect suppressor activity (with freshly isolated cells) in antibody-based co-culture assays (Baecher-Allan et al., 2001). This was also found in the preferred culture system of the present invention, where the most stringently purified CD4$^+$CD25$^+$ cells form the best suppressor cell line precursors. Contaminating CD25$^-$ dim cells in CD25$^+$ fractions can grow faster and overgrow the CD25$^+$ bright cells, and thereby preclude the full manifestation of suppressor cell function. Thus, in the preferred embodiments of this invention "stringent purification" is emphasized (preferably two cycles of selection, and extensive washing). A "high level of stringency" is preferred to optimize purity, even at the cost of a lower cell yield. Such highly stringent techniques would be known to and understood by one skilled in the art.

Lower titers of anti-CD25 magnetic microbeads (1/5th of the manufacturer's recommendation) and a re-purification over a second column greatly facilitated the generation of Treg cell lines with potent suppressive capabilities. By comparison, the use of even lower titers of anti-CD25 mAb-coated magnetic microbeads or addition of a third column step to the purification, did not significantly improve results over those of the preferred culture system (see Example 8), and in fact, disadvantageously decreased yields.

By increasing the stringency of CD4$^+$CD25$^+$ T cell purification, eventually the isolated CD25 bright cells no longer grew, even with the anti-CD3/anti-CD28 beads. However, after trying various accessory cell populations, irradiated CD4$^+$ T cells (used as "feeder cells") were found to be the best for facilitating growth for the present invention. The cells appeared to secrete suppressor cell growth factors, including but not limited to IL-2. However, conditioned media (supernatant from anti-CD3/anti-CD28 stimulated CD4$^+$ T cells) greatly facilitated suppressor cell growth, even more so than that which resulted from IL-2 supplementation.

Nevertheless, alternative culture-expansion strategies, such as may be known to one skilled in the art, are also contemplated that may not require the addition of a feeder cell population. For example, anti-CD3/28 beads+IL-2 may be used, in which case host APCs and/or dendritic cells may or may not be beneficial or required.

Improved suppressor cell line generation. In the course of the experiments, it was found that the suppressor cell lines were susceptible to overgrowth by CD8$^+$ non-suppressor cells. Thus, a two step purification protocol was developed to deplete CD8$^+$ T cells. This included a multi-sort magnetic microbead approach, wherein cells were first stained with anti-CD25 FITC (fluorescein-5-isothiocyanate) by recognized methods, and then isolated with anti-FITC microbeads, again using known methods. The beads were then cleaved from the preparation, followed by a second step wherein anti-CD8 microbeads were used to deplete the CD8$^+$ T cells. Anti-CD19, anti-CD20, anti-CD14, and anti-CD56 were added to simultaneously deplete B cells, monocytes, and NK cells from the preparation. Cell lines generated from this purification strategy proved to be more reproducibly generated (>90%), and more stable over longer culture times than other methods.

Using the two step purification protocol, it was possible to explore CD4$^+$CD25$^+$ subsets on freshly isolated suppressor cell populations. Minor subsets of CD4$^+$CD25$^+$ cells were found that included integrin β7 and CD200 (~10% of CD4$^+$CD25$^+$ cells), and major subsets were found to include LAIR (leukocyte-associated immunoglobulin-like receptor-1, see, e.g., Meyaard et al., *Immunity* (2):283-90) CD101 cells (representing ~80% of CD4$^+$CD25$^+$ cells, see, e.g., Allez et al., *Gastroenterology* 123(5):1516-1526 (2002)). The cell lines do not express CD103 (integrin-alpha-E), expressed at high levels on a potent subset of mouse CD4$^+$CD25$^+$ cells. In addition, about 20% of the CD4$^+$CD25$^+$ cells express CD45RA. This antigen is not expected to be expressed on suppressor cells, as they have been described in several reports to be CD45RO positive (generally mutually exclusive expression, except for transiently during activation of naïve cells). However, the isolation of these cells was much better than the CD45RA$^-$ cells for generating suppressor cell lines (to date 12/12 cell lines isolated by this method were found to be potent suppressors). On naïve T cells the CD45RA splice variant is expressed on the T cell surface. Once a T cell differentiates into a memory cell, it usually expresses the CD45RO isoform (see, e.g., DeRosa, 2001; Tchilian et al., *Arch. Immunol. Ther. Exp.* (Warsz) 50(2):85-93 (2002)).

Although the best protection (despite the lower number of infused cells) was mediated by the culture method that resulted in the lowest recovery (allogeneic splenocytes, low dose IL-2 and a growth factor (TGF-β), as shown in the examples that follow), culture protocols can be modified in light of the information provided herein and known principles to optimize both expansion and suppressor function. Allogeneic splenocytes did not result in sufficient expansion of CD25$^+$ cells even in the presence of high dose IL-2 under these conditions to be clinically feasible in humans based upon the findings in the mouse model. However, it is anticipated that a more potent antigen presenting cell, such as an activated monocyte-derived dendritic cell (DC) would result in better expansion and superior function through the delivery of multiple physiological signals that may also aid cell survival as shown in the examples that follow.

However, because CD4$^+$CD25$^+$ cells do not require activation via alloantigen per se to inhibit alloantigen-reactive CD25$^-$ T cells (i.e., the population of Treg cells depleted of CD25$^+$ cells), it may be desirable to achieve maximal activation (and expansion) by polyclonal inducers of TCR signaling, as long as activation-induced cell death does not completely mitigate the beneficial effect. "Activation" refers to stimulating or enhancing cellular proliferation and the cell division necessary to produce progeny cells from the original cell population. Although there is significant inhibition of GVHD with CD25$^+$ cells cultured with immobilized anti-CD3 mAb and high dose IL-2, the inclusion of TGF-β in any of the activation protocols may be warranted, as data presented herein indicate that TGF-β is a growth factor for CD25$^+$ regulatory cells, and additionally that it renders them more resistant to activation-induced cell death Yamagiwa et al, 2001; Nakamura et al., 2001).

Surprisingly, the activation or maturation of the dendritic cells (DCs) did not lead to the bypass of suppression. "Maturation" is the conversion of the morphology and function of APCs from an immature to an activated mature state. The activated DC is the most potent APC. Dendritic cells go from immature>mature>activated states. By comparison, "activation" is the acquisition of cell surface molecules and biological properties in immature or mature cells. Accordingly, the APC/DC cells are capable of supporting an immune response. A series of signals and cytokines triggers the differentiation. TNF, PGE$_2$, and interferon can make a DC go from immature to mature; whereas CD40L signaling or LPS can make a DC go from mature to activated.

Thus, the present finding provides in human cells a marked contrast to what has been recently reported for freshly isolated murine Treg cells, where LPS or CpG-containing DNA oligodeoxynucleotide-mediated signaling of spleen-derived DCs led to the bypass of suppression (Pasare et al., *Science* 299(5609):1033-1036 (2003)). However, in that system the Treg cells were neither culture-activated, nor culture-expanded.

In contrast in the preferred embodiments of the present invention, the activated and expanded human Treg cells can override the cytokines and co-stimulatory molecules expressed by activated DC, and still block the MLR response. The finding of increased potency of suppressor function after culture is consistent with what has been shown with the activation of murine Treg cells. Suppressor function is activation dependent (Shevach et al., 2002, supra), and short term culture with anti-CD3 and IL2 augments suppressive ability (Thornton et al., 2000). This is interpreted to mean that the long term cultured Treg cells are primed (more sensitive) to reactivation of TCR, and hence TCR induced suppressor function is more readily expressed.

In an alternative embodiment, to increase $CD4^+CD25^+$ cell yield, thus permitting the anti-GVHD effect to be enhanced, cytokines are added in the culture, e.g., IL-4 and IL-7, which have been shown to increase survival of T cells (Vella et al., *Proc. Natl. Acad. Sci. USA* 95:3810-3815 (1998)), IL-10, which has been shown to be responsible for the generation of regulatory T cells (Groux et al., *Nature* 389:737-42 (1997)), and IL-15 which has been shown to synergize with low dose IL-2 to induce vigorous proliferation of human $CD4^+CD25^+$ cells (Dieckmann et al., 2001).

Therapeutic efficacy of activation and expansion protocols. An important contribution of the present invention is that this model allows for the evaluation of the in vivo therapeutic efficacy of activation and expansion protocols of $CD4^+CD25^+$ cells in a relevant animal model. Because of the known potential deficits of activated cultured cells in homing, migration, survival, and function in vivo, it is important that the regulatory function of ex vivo activated and expanded regulatory cells be considered for in vivo applications, as well as in vitro.

The regulatory role of the $CD4^+CD25^+$ cells in immune responses to foreign or alloantigens, the increase in GVHD lethality resulting from CD25-depletion, as well as the in vivo depletion data, in which anti-CD25 mAb is administered to the recipient in autoimmunity, suggest therapies of clinical relevance. Anti-CD25 mAb administered to the recipient pre-transplant in an attempt to avoid depletion of host-reactive donor T cells that would up-regulate CD25 as an activation marker during GVHD, resulted in accelerated GVHD. This was surprising since, based on the prior art alone, this scenario would have been predicted to ameliorate GVHD (Anasetti et al., *Bone Marrow Transplant* 7:375-381 (1991); Harris et al., *Bone Marrow Transplant* 23:137-144 (1999); Cahn et al., *Transplantation* 60:939-942 (1995); Blaise et al., *Bone Marrow Transplant* 8:105-111 (1991)). However, as GVHD was worsened by the infusion of anti-CD25 mAb prior to transplantation, it appears that resistant host $CD25^+$ cells may also inhibit the generation of GVHD by the donor T cell inoculum via a host anti-donor resistance mechanism.

As shown in the examples that follow, ex vivo expanded and activated immune regulatory $CD4^+CD25^+$ cells significantly inhibited rapidly lethal GVHD in vivo. As noted above, a number of cell types can be used. When cells from lymph nodes are used, all types of lymph nodes are contemplated (e.g., inguinal, mesenteric, superficial distal auxiliary, and the like), and may be from healthy or diseased patients depending on the desired outcome. For example, tumor-draining lymph node cells may be isolated, purified and culture-expanded using the methods provided herein. A sufficiently large number of such cells (i.e., a number adequate to show the desired suppressive or preventative reaction upon re-infusion into an autologous host or infusion into an allogeneic recipient) are purified at a high level of stringency and diluted in synthetic culture media (e.g., RPMI 1640 with typical supplements) under the disclosed conditions for the appropriate period of time. Any number of standard culture techniques can be employed (e.g., multi-well plates in an incubator at, for example, 37° C. in a 5% $CO_2$ atmosphere). For ex vivo stimulation, the cells are removed aseptically from the host and single cell suspensions are prepared under sterile conditions. Cell preparations may be filtered (e.g., through a layer of nylon mesh), centrifuged and subjected to a gentle lysing procedure, if necessary.

The ex vivo culture-expanded cells may be reintroduced to the host or to another patient by a number of approaches. Preferably, they are injected intravenously. Optionally, the host may be treated with agents to promote the in vivo function and survival of the stimulated cells (e.g., IL-2 or IL-15). Of course, the culture-expanded cells may also be reintroduced in a variety of pharmaceutical formulations. These may contain such normally employed additives as binders, fillers, carriers, preservatives, stabilizing agents, emulsifiers, and buffers. Suitable diluents and excipients are, for example, water, saline, and dextrose, as ustilized in the methods described below.

Thus, either donor (allogeneic) or host-type $CD25^+$ (autologous) cells are useful for inhibiting GVHD responses, and further suggesting that maintenance of host $CD25^+$ cells would be clinically desirable. Because human $CD4^+CD25^+$ regulatory cells have been shown to inhibit in vitro allo-responses of both naïve and memory $CD4^+$ T cells, and can be expanded in vitro with maintenance of suppressor function (Dieckmann et al., 2001; Levings et al., 2001; Jonuleit et al., 2001), these principles are applicable to the present invention. The Levings report is the only disclosure of human CD4+ CD25+ polyclonal expansion, using soluble anti-CD3, and lymphoblastoid cells and PBMC as feeder cells+IL-2. However, the suppressive function noted by Levings et al. was merely a 65% reduction of proliferation at a suppressor/responder cell ratio of 1:1, which was less than typically observed with mouse Treg cells. Thus, the Levings et al. report is not considered to be significant with regard to the present long term, ex vivo culture expansion methods used herein.

Therapeutic Methods. The methods of the present invention are particularly useful for humans, but may also be practiced on veterinary subjects. An "individual," "subject," "patient" or "host" referred to herein is a vertebrate, preferably a mammal. More preferably, such individual is a human and the culture-expanded cells are human, although animals, including animal models for human disease states, are also included in this invention and therapeutic treatments of such animals are contemplated herein. Such animal model can be used to test and adjust the compositions and methods of this invention, if desired. Certain models involve injecting in-bred animals with established syngeneic cell lines. Also useful are chimeric animal models, described in U.S. Pat. Nos. 5,663, 481, 5,602,305 and 5,476,993; EP application 379,554; and International Appl. WO 91/01760. Non-human mammals include, but are not limited to, veterinary or farm animals, sport animals, and pets. Accordingly, as opposed to animal models, such animals may be undergoing selected therapeutic treatments.

The immune status of the recipient or host may be any of the following. The individual may be immunologically naive with respect to certain antigen presenting cells (APC) or tumor-associated antigens (TAA) present in the composition. The individual may not currently be expressing anti-tumor immunity, but may have immunological memory, particularly T cell memory relating to a particular antigen.

The compositions containing the present modified and/or activated and enhanced cell population, or a cocktail thereof, can be administered for the prophylactic and/or therapeutic treatments. In therapeutic application, compositions are administered to a patient in an amount sufficient to prevent, suppress, block or inhibit, or at least partially arrest the immunogenic response, such as that which takes place prior to the onset of GVHD or during the GVHD response and its complications. An amount adequate to accomplish this is defined as a "therapeutically effective dose." Amounts effective for this use will depend upon the severity of the disease and the general state of the patient's own immune system, but generally range from about 0.05 mg/kg body weight to about 5 mg/kg body weight, preferably between about 0.2 mg/kg body weight to about 1.5 mg/kg body weight.

In prophylactic applications, compositions containing the present modified, and/or activated and enhanced cell population, or a cocktail thereof, are administered to a patient not already in a disease state to enhance the patient's resistance. Such an amount is defined to be a "prophylactically effective dose." In this use, the precise amounts again depend upon the host's state of health and general level of immunity, but is generally in the ranges described above.

Single or multiple administrations of the compositions can be carried out with dose levels and pattern being selected by the treating physician. In any event, the pharmaceutical formulations should provide a quantity of the modified CD25 cells of this invention sufficient to treat the patient effectively.

The terms "immunogen," or "immunogenic composition" or "vaccine" are used herein to refer to a compound or composition, as appropriate, that is capable of either: a) generating an immune response against an antigen in a naïve individual; or b) reconstituting, boosting, or maintaining an immune response in an individual. The immunological response may comprise antibodies, immunoreactive cells (such as helper/inducer or cytotoxic cells), or any combination thereof.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins, such as mitomycin C, or irradiation. Cells that have been fixed or permeabilized and are incapable of division are also examples of inactivated cells.

In general, the practice of embodied methods of the present invention will employ, unless otherwise indicated, conventional techniques of molecular biology, microbiology, cell biology, biochemistry and immunology, which are within the skill of the art. Such techniques and necessary definitions are explained fully in the literature, such as, *Molecular Cloning: A Laboratory Manual*, 2nd edition (Sambrook et al., 1989); *Oligonucleotide Synthesis* (Gait, ed., 1984); *Animal Cell Culture* (Freshney, ed., 1987); *Methods in Enzymology* (Academic Press, Inc.); *Handbook of Experimental Immunology* (Weir & Blackwell, eds.); *Gene Transfer Vectors for Mammalian Cells* (Miller & Calos, eds., 1987); *Current Protocols in Molecular Biology* (Ausubel et al., eds., 1987); *PCR: The Polymerase Chain Reaction*, (Mullis et al., eds., 1994); *Current Protocols in Immunology* (Coligan et al., eds., 1991). General procedures for the preparation and administration of pharmaceutical compositions are outlined in *Remington's Pharmaceutical Sciences*, 18th Edition (1990), Martin ed., Mack Publishing Co., Pa.

The treated individual may be exhibiting an active autoimmune response (either humoral or cellular immunity, or both) or GVHD. However, the subject should be at least partly immunocompetent, so as to minimize a GVHD reaction of pathological scope. However, it is recognized that cancer patients or those affected by autoimmune or other immunogenic diseases often show a degree of immunosuppression, and this does not necessarily prevent the use of the compositions of the invention, as long as the compositions may be given safely and effectively Examples of cancers that can be treated according to this invention include, but are not limited to tumors from sites that are thought to be immune privileged, such as the brain, and sites that are not immune privileged, such as the lung, colon, breast, liver, uterus or ovary, pancreas, prostate, skin and blood, as well as many other specific or non-specific sites in the body of a human or animal. Examples of such tumors are well known to those of skill in the art and include small cell lung cancers.

Modes of Administration and Dose. The compositions of this invention can be administered to the subject by any recognized methods, either systemically or at a localized site. The most convenient time to administer the alloactivated cells to prevent GVHD in a transplant patient or in a cancer patient is during the time of surgery. To keep the cells at the site until completion of the surgical procedure, it is convenient to administer the cells in a pharmaceutically compatible artificial gel, or in clotted plasma or by utilizing any other known controlled release mechanism.

When less invasive procedures are desired, the composition can be injected at a desired location through a needle. For deeper sites, the needle can be positioned using endoscopic ultrasound techniques, radioscintigraphy, or some other imaging technique, alone or in combination with the use of an appropriate scope or cannula. For such applications, the cell population is conveniently administered when suspended in isotonic saline or a neutral buffer to a volume of about 10 ml.

Similarly, prior to or simultaneously with an allogeneic transplant, an effective amount of isolated $CD4^+CD25^+$ cells, preferably modified to improve or culture-enhance their suppressive effect are administered as a cellular implant to the transplant recipient (the host) in an amount sufficient to prevent or block the occurrence of GVHD. In the alternative, the cellular implant is administered following the allogeneic transplant to block, inhibit or reverse GVHD that may have already begun. The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^6$ to $10^{12}$ cells, more preferably $10^8$ to $10^{11}$ cells, including allogeneic stimulators and responders. Preferably, between about $1\times10^9$ to $5\times10^{10}$ cells are used; more preferably between about $2\times10^9$ to $2\times10^{10}$. On average as many as $1\times10^9$ culture-expanded Treg cells will be needed for clinical trials in a human. Multiple doses when used in combination to achieve a desired effect each fall within the definition of an effective amount.

The various components of the implanted or injected composition are present in an "effective combination," meaning that there are sufficient amounts of each of the components for the composition to be effective. Preferably, at least about $1\times10^8$, more preferably between about $1\times10^9$ to $5\times10^{10}$, and more preferably between about $2\times10^9$ to $2\times10^{10}$ responder cells are present. Preferably, at least about $1 \times 10^7$, more preferably between about $5 \times 10^7$ to $5 \times 10^9$ and; more preferably between about $1 \times 10^8$ to $2 \times 10^9$ suppressor cells are present. Ratios of allogeneic lymphocytes to suppressor leukocytes is generally between 1:1 and 100:1, usually between about 5:1 and about 25:1, and typically about 10:1, as further described in specific examples herein. However, any number of component cells or other constituents may be used, as long as the composition is effective as a whole. This will also depend upon culture conditions and other factors during preparation.

The pharmaceutical compositions of this invention may be given following, preceding, in lieu of, or in combination with, other therapies relating to generating an immune response or treating cancer in the subject or reducing the effect of GVHD. For example, the subject may have previously been or concurrently be in the process of treatment by chemotherapy, radiation therapy, and other forms of immunotherapy and adoptive transfer.

Where such modalities are used, they are preferably employed in a way or at a time that does not interfere with the immunogenicity of the compositions of this invention. The subject may also have been administered another composition, such as a vaccine, in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines. When the culture-expanded Treg cells are derived from a specific origin, such as a cancer or cancer cell, the term is intended to include, for example, not only a primary cancer cell, but any cell derived from a cancer cell ancestor, metastasized cancer cells, and in vitro cultures and cell lines derived from cancer cells.

Certain embodiments of this invention relate to combination therapies. In one combination therapy, the subject is infused with ex vivo culture-expanded autologous or allogeneic $CD4^+CD25^+$ T cells, either before, during, or after tissue transplantation to promote engraftment and suppress or prevent GVDH responses. Although only a single infusion s disclosed, such infusions may be given weekly for a period of time (such as for 4-6 weeks) following the cellular implant, to enhance the extent of the supressive response in the host or the therapeutic effectiveness. The infusions can also be given after intervals of several months in order to replenish the response. Accordingly, certain embodiments of this invention relate to administering a cellular implant, and subsequently boosting the therapeutic effect or immunological response by administering to the patient a composition comprising allo-activated human $CD4^+CD25^+$ T cells autologous or allogeneic to the patient, but treated ex vivo. Certain embodiments may further comprise an inactivated cell population of tumor cells or the progeny thereof when the patient is a cancer patient or progeny In preferred embodiments, an allogeneic cell transplant would also provide the desired results, although it may take more cells than if autologous cells were used. Moreover, the method has a higher probability of success if the cells were purified at a high level of stringency and CD25-depleted to reduce the volume of cells needed to achieve a therapeutic effect in the patient and to enhance the efficiency of the cellular implant.

Timing of administration of compositions of this invention is within the judgment of the managing physician, and depends on the clinical condition of the patient, the objectives of treatment, and concurrent therapies also being administered. Suitable means of immunological monitoring include a one-way MLR using patient's PBL as responders and primary tumor cells as stimulators. An immunological reaction may also be manifest by a delayed inflammatory response at the injection site. Suitable means of monitoring of the effectiveness of the Treg cell treatment may include in vitro assays, such as MLR, or in vivo tracking, such as CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when the immunological or clinical benefit appears to subside, additional booster or maintenance doses may be given as required.

When multiple cellular implants or combinations of implants and cellular vaccines are given to the same patient, attention should be paid to the possibility that the allogeneic lymphocytes in the vaccine may generate an anti-allotype response. The use of a mixture of allogeneic cells from a plurality of donors, and the use of different allogeneic cell populations in each dose, are both strategies that can help minimize the occurrence of an anti-allotype response.

During the course of therapy, the subject is evaluated on a regular basis for general side effects such as a febrile response. Side effects are managed with appropriate supportive clinical care.

Alternate Embodiments: Tumor lymphocytes may become anergized in the course of tumor growth in vivo and become refractory to activation or expansion. Various cytokines may partially reverse T memory cell anergy, namely, IL-2, IL-4, IL-15, or IL-1 plus IL-6. These cytokines may promote T cell proliferation and may represent an essential "second signal" typically provided by antigen presenting cells. Hence, responsiveness of tumor sensitized lymphocytes may be restored by co-culturing with various cytokines and mitogens, such as anti-CD3 antibody or conconavalin A.

The present invention is further described by example. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims, rather such claims should be construed to encompass any and all variations that become evident as a result of the teachings provided herein.

EXAMPLES

The materials and methods, described in Example 1 were commonly used in Examples 2-5, while those described in Example 6 were commonly used in Example 7.

Example 1

Increased Proportion of $CD4^+CD25^+$ Cells in Patients with NSCLC

Peripheral blood and tumor were collected from patients with either stage I or II non-small cell lung cancer (NSCLC) at the time of surgery after obtaining appropriate informed consent under Institutional Review Board approved protocols. Fresh tumor specimens from 8 NSCLC patients were processed by sterile mechanical dissection followed by enzymatic digestion, as described by Woo et al., 2001. Cells were separated on a Percoll (Pharmacia Biotech AB, Sweden) density gradient. Peripheral blood was obtained at the time of tumor collection, and processed as described by Woo et al., 2001, and frozen.

Cytokine production was determined by placing 70,000 CD3$^+$CD4$^+$CD25$^-$, or CD3$^+$ (–CD4$^+$CD25$^+$) cells into 96-well plates (Falcon, Franklin Lakes, N.J.) for 2-day culture in 200 µl total volume. Supernatants were then harvested and tested for cytokine production using Quantikine human TGF-β, IL-2, and IL-10 ELISA kits (R&D Systems, Minneapolis, Minn.).

The respective CD25 population was digested and the tumor-infiltrating lymphocytes were analyzed by flow cytometry (FIG. 1). For proliferation assays, 96-well plates were coated with 1 µg/mL of anti-CD3 (Kung et al., *Science* 206: 347-349 (1979)) or 1 µg/mL of anti-CD3 and anti-CD28 (Hansen et al., *Immunogenetics* 10:247-260 (1980)) antibody overnight at 37° C. Peripheral blood lymphocytes from patients or normal donors were thawed and cultured in RPMI 10% FCS (Hyclone, Logan, Utah) at 5×10$^4$ cells (200 ul) per well in triplicate at 37° C., 5% CO$_2$. Purified CD3$^+$CD4$^+$CD25$^-$, or CD3$^-$(–CD4$^+$CD25$^+$) T cells were added at varying numbers (0-20,000 depending on the example). Blocking experiments were performed with 10 µg/mL anti-TGF-β antibody (R&D Systems). Proliferation was assayed by measuring [$^3$H]thymidine incorporation (Stephens et al., 2001). Enrichment of CD3$^+$CD4$^+$CD25$^+$, CD3$^+$CD4$^+$CD25$^-$, or CD3$^+$(–CD4$^+$CD25$^+$) cells was performed on a Cytomation (Fort Collins, Colo.) MoFlo Cell Sorter (by gating on lymphocytes, CD3$^+$CD4$^+$ T cells).

Thus, when the frequency (%) of CD4$^+$CD25$^+$ lymphocytes present in the total CD4$^+$ cells population isolated from lung cancer tumor specimens as compared with the peripheral blood lymphocytes (PBL) of the lung cancer patients was determined by flow cytometry, it was determined that 33% of the tumor infiltrating lymphocytes (TIL) were CD4$^+$CD25$^+$. This was consistent with the activated phenotype of regulatory T cells. In FIG. 1, the distributions and means are shown as PBL of normal donors, n=7 [FIG. 1A]; unstimulated tumor infiltrating lymphocytes (TIL) from patients with NSCLC, n=8 [FIG. 1B]; or unstimulated PBL from patients with NSCLC, n=9 [FIG. 1C]. Notably, the peripheral blood of patients with NSCLC had a similar increase in the percentages of CD4$^+$CD25$^+$ cells.

In contrast, less than 15% of the PBL of normal donors had this CD4$^+$CD25$^+$ cell phenotype, which was consistent with previous reports (Shimizu et al., *J. Immunol.* 163:5211-5218 (1999); Jonuleit et al., 2001; Levings et al., 2001; Dieckmann et al., 2001).

Example 2

Bright Constitutive Surface Expression of CD152 (CTLA-4) on Tumor Infiltrating Lymphocytes Recent studies have shown that CTLA-4 is up-regulated on mouse and human regulatory cells (Jonuleit et al., 2001; Dieckmann et al., 2001; Read et al., 2000). Therefore, the lymphocytes from normal donors and NSCLC patients were analyzed for expression of CD4, CD25 and CTLA-4 by flow cytometry.

Figure 2A:
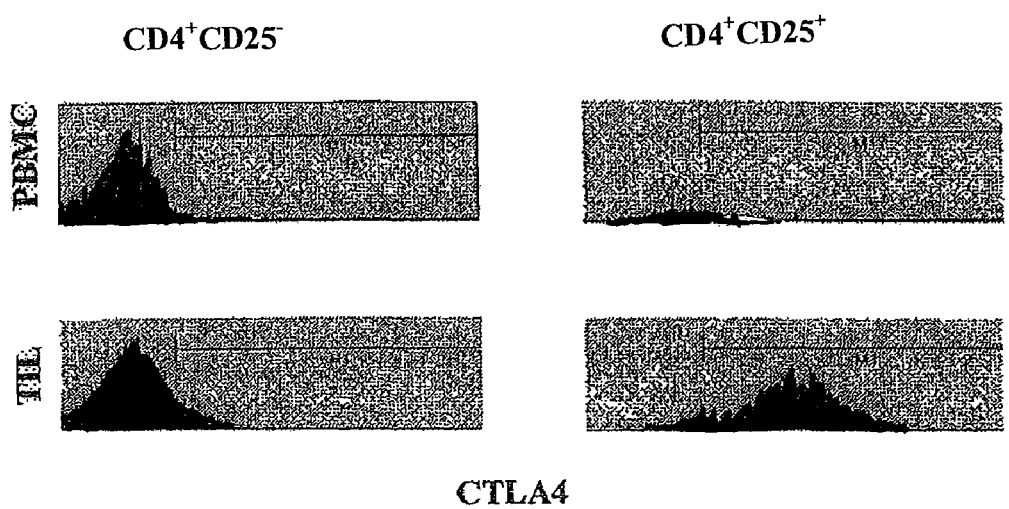
FIGS. 2A-2B graphically show the increased CTLA-4 expression found in tumor infiltrating CD4+CD25+ cells.
Figure 2B:
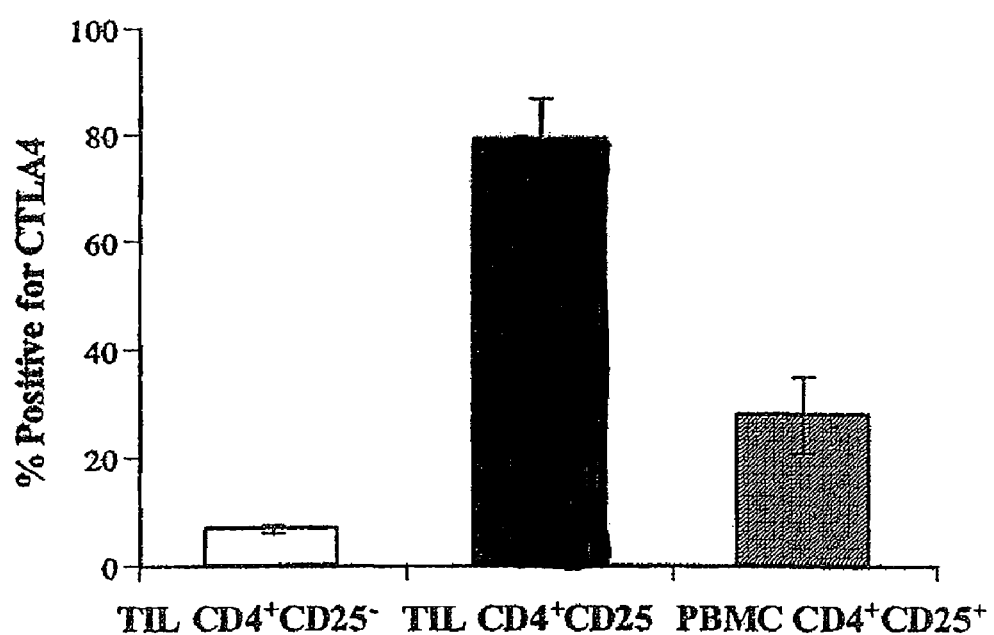

Bright surface expression at levels comparable to CD4 and CD8 levels of expression, rather than the expected dim or undetectable expression of CTLA4 that is usually observed (often requiring permeablizing the cell in order to detect CTLA-4 expression) of CTLA-4 was detected on resting lymphocytes derived from the tumor specimens (FIG. 2), whereas in resting T cells from normal donors, less than 1% of T cells were positive for CTLA-4 expression (data not shown). Therefore, from an evaluation of 2 representative patients demonstrating CTLA-4 expression in CD4$^+$CD25$^-$ and CD4$^+$CD25$^+$ TIL and peripheral blood mononuclear cells (PBMC), a flow histogram is shown in FIG. 2A, while FIG. 2B shows the mean (±S.E.) percentage of cells expressing CTLA-4 in CD4$^+$CD25$^-$ tumor infiltrating lymphocytes (left), CD4$^+$CD25$^+$ TIL (middle), and CD4$^+$CD25$^+$ PBMC (right) from 5 consecutive NSCLC patients. Among the CD4$^+$CD25$^+$ cells from tumor specimens, 80% were positive for and showed increased expression of CTLA-4. In contrast, less than 10% of the CD4$^+$CD25$^-$ lymphocytes in the tumor specimens were positive for CTLA-4.

In order to exclude the binding of shed CTLA-4 to B7 molecules that are expressed on activated human T cells (Greenfield et al., *J. Immunol.* 158:2025-2034 (1997)), CTLA-4 mRNA was measured by quantitative PCR. Substantially higher levels of CTLA-4 mRNA (2 to 7 fold; n=3 patients) was observed in the CD4$^+$CD25$^+$ cells than in the CD4$^+$CD25$^+$ cells (data not shown). In contrast to the near uniform expression of CTLA-4 on CD4$^+$CD25$^+$ cells in tumor specimens, only 30% of the peripheral CD4$^+$CD25$^+$ cells from lung cancer patients stained positive for CTLA-4 (FIG. 2).

Example 3

Tumor Infiltrating CD4$^+$CD25$^+$ Cells Inhibit Proliferation of Autologous Peripheral Blood T Cells To assess the function of CD4$^+$CD25$^+$ CTLA-4$^+$ cells in lung cancer patients, CD4$^+$CD25$^+$ cells were separated from the remaining tumor infiltrating lymphocytes by high speed cell sorting, and their proliferative capacity and effect on T cell proliferation were determined. Regulatory T cells typically fail to proliferate in response to mitogenic stimulation (Shevach et al., *J. Exp. Med.* 193:F41-F46 (2001)). To confirm this, 50,000 CD4$^+$CD25$^+$ or CD3$^+$ tumor-infiltrating lymphocytes (TIL) depleted of CD4$^+$CD25$^+$ cells were stimulated with immobilized anti-CD3 and anti-CD28. The CD3$^+$ cells depleted of CD4$^+$CD25$^+$ cells proliferated, while the CD4$^+$CD25$^+$ cells did not (data not shown).

Next, autologous peripheral blood lymphocytes were stimulated under suboptimal or optimal conditions in the presence of increasing numbers of the putative regulatory cells. Autologous PBL were cultured alone or with increasing numbers of sort purified CD4$^+$CD25$^+$ or CD4$^+$CD25$^-$ tumor infiltrating lymphocytes (TIL) from lung cancer specimens. CD4$^+$CD25$^+$ TIL were added to control cultures. Suboptimal proliferation was induced with soluble anti-CD3 or immobilized anti-CD3, and optimal proliferation was induced with immobilized anti-CD3 and anti-CD28. [$^3$H]thymidine incorporation was measured during the last 18 hours of a 4-day culture. Results were expressed as the percent response of PBL cultured alone. 100% proliferation for the CD25$^-$ plot was 37081±4094 cpm, and 29465±1007 cpm for the CD25$^+$ plot.

Figure 3A:
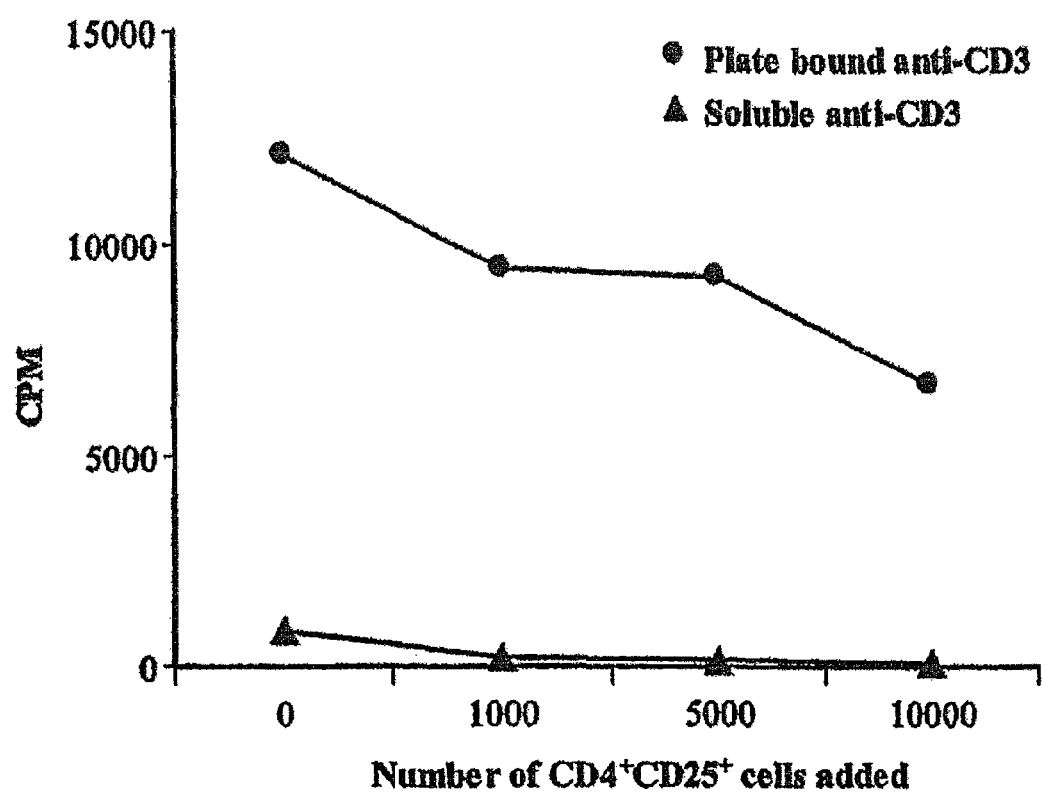

As anticipated, soluble anti-CD3 stimulated low levels of proliferation, and direct inhibition of soluble anti-CD3 stimulated proliferation was seen with the addition of tumor infiltrating CD4$^+$CD25$^+$ T cells (FIG. 3A). Nevertheless, immobilized (plate bound) anti-CD3 induced more vigorous proliferation, and there was a dose dependent decrease in T cell proliferation with the addition of CD4$^+$CD25$^+$ cells.

However, in contrast to previous reports in mouse T cells (Thornton et al., 1998), optimal proliferation stimulated by anti-CD3 and anti-CD28 (plastic immobilized anti-CD3/CD28) was also suppressed by addition of as few as 10-20% CD4$^+$CD25$^+$ lymphocytes derived from the lung cancer specimens (FIG. 3B). This inhibition was potent. In 5 consecutive patients, the addition of 10,000 CD4+CD25+ T cells to 50,000 autologous PBL yielded a 60% mean inhibition of anti-CD3/CD28 stimulated proliferation of autologous PBL. In contrast, neither CD3+ tumor infiltrating lymphocytes depleted of CD4+CD25+ cells (FIG. 3B), nor irradiated PBL (data not shown) cultured with responder cells suppressed proliferation of autologous PBL, demonstrating that the effects were not due to space or nutrient deficiencies.

Example 4

CD4+CD25+ Tumor Infiltrating Lymphocytes Fail to Suppress Allogeneic PBL

Figure 4A:
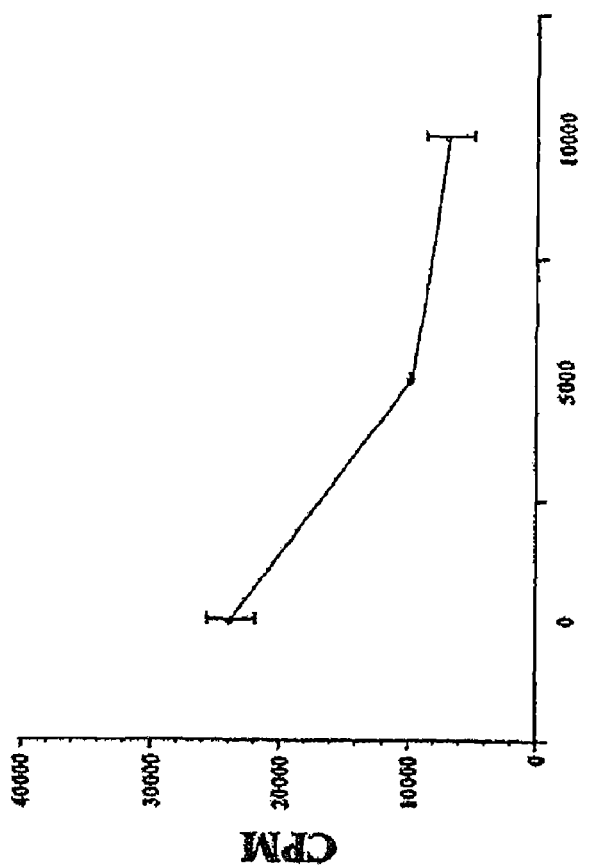
Figure 4B:
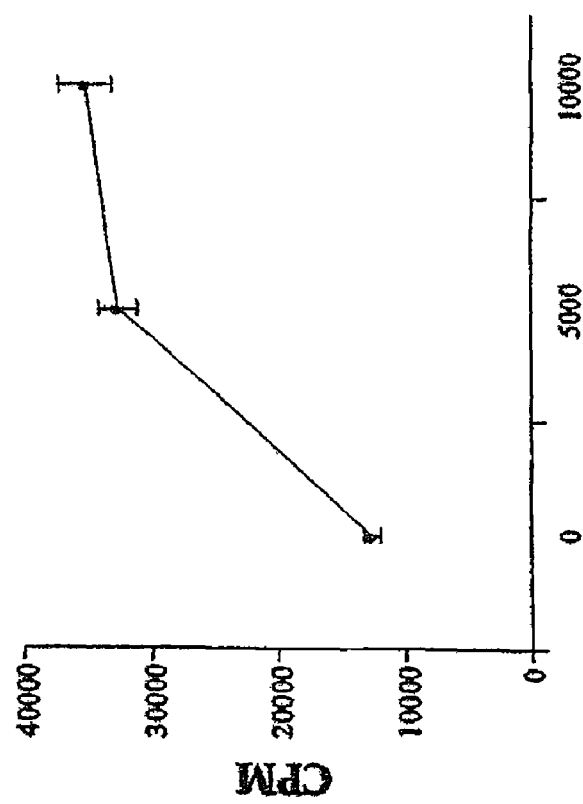

To determine the ability of freshly isolated tumor infiltrating CD4+CD25+ T cells to inhibit the proliferation of peripheral blood T cells, allogeneic peripheral T cells from normal donors or autologous PBL from unrelated lung cancer (NSCLC) patients were cultured with tumor infiltrating CD4+CD25+ cells from the cancer patient (the amount of cells used are shown in FIGS. 4A and 4B, respectively). All cell cultures in this Example were stimulated with plate bound anti-CD3/CD28. [$^3$H]thymidine incorporation was measured during the last 18 hours of a 4-day culture.

The CD4+CD25+ T cells were unable to inhibit the proliferation of anti-CD3/anti-CD28 stimulated PBL from the normal donors (FIG. 4A); and there was actually an enhanced proliferative effect with increasing numbers of CD4+CD25+ T cells. In a companion culture, the tumor derived CD4+CD25+ T cells effectively inhibited the anti-CD3/28 induced proliferation of autologous PBL (FIG. 4B), confirming the inhibitory function of this population of tumor derived CD4+CD25+ T cells. Results are expressed as means of triplicate cultures (±S.E.) for one of three independent experiments in FIG. 4A, or one of two independent experiments in FIG. 4B, each with similar results.

Peripheral blood T cells from a normal donor were then cultured with autologous sort purified peripheral blood CD4+CD25+ donor T cells as shown in FIG. 4C. As was the case with tumor-derived CD4+CD25+ T cells, the proliferation of normal donor responder PBL were suppressed by culturing them with increasing numbers of autologous CD4+CD25+ T cells isolated from the peripheral blood (FIG. 4C). Results are expressed in FIG. 4C as means of triplicate cultures (±S.E.) for one of two independent experiments, each with similar results.

Tumor infiltrating CD4+CD25+ or CD4+CD25− cells were then cultured with allogeneic PBL from a NSCLC patient. However, the tumor derived CD4+CD25+ cells from patient A could not inhibit the proliferation of PBL from patient B, an unrelated NSCLC patient as shown in FIG. 4D. Results are expressed in FIG. 4D as means of triplicate cultures (±S.E.) for one of four independent experiments, each with similar results.

Together these experiments indicate that that the regulatory T cells infiltrating tumors potently suppress the mitogen-induced proliferation of autologous T cells, but that they cannot suppress the proliferation of allogeneic PBL.

Example 5

TGF-β is not Required for Inhibition of Proliferation

To determine whether TGF-β secretion by the regulatory T cells isolated from tumors contributed to their suppressive function, CD4+CD25+ and CD3+ cells depleted of CD4+CD25+ cells from lung cancer specimens were placed in culture for 2 days. Supernatants were tested for TGF-β by ELISA. In results representing from 1 of 6 patients (±S.E for triplicate wells), unstimulated, sort-purified CD4+CD25+ T cells constitutively produced significant amounts of TGF-β (FIG. 5A), but production of IL-2 and IL-10 was undetected by ELISA (data not shown).

Figure 5A:
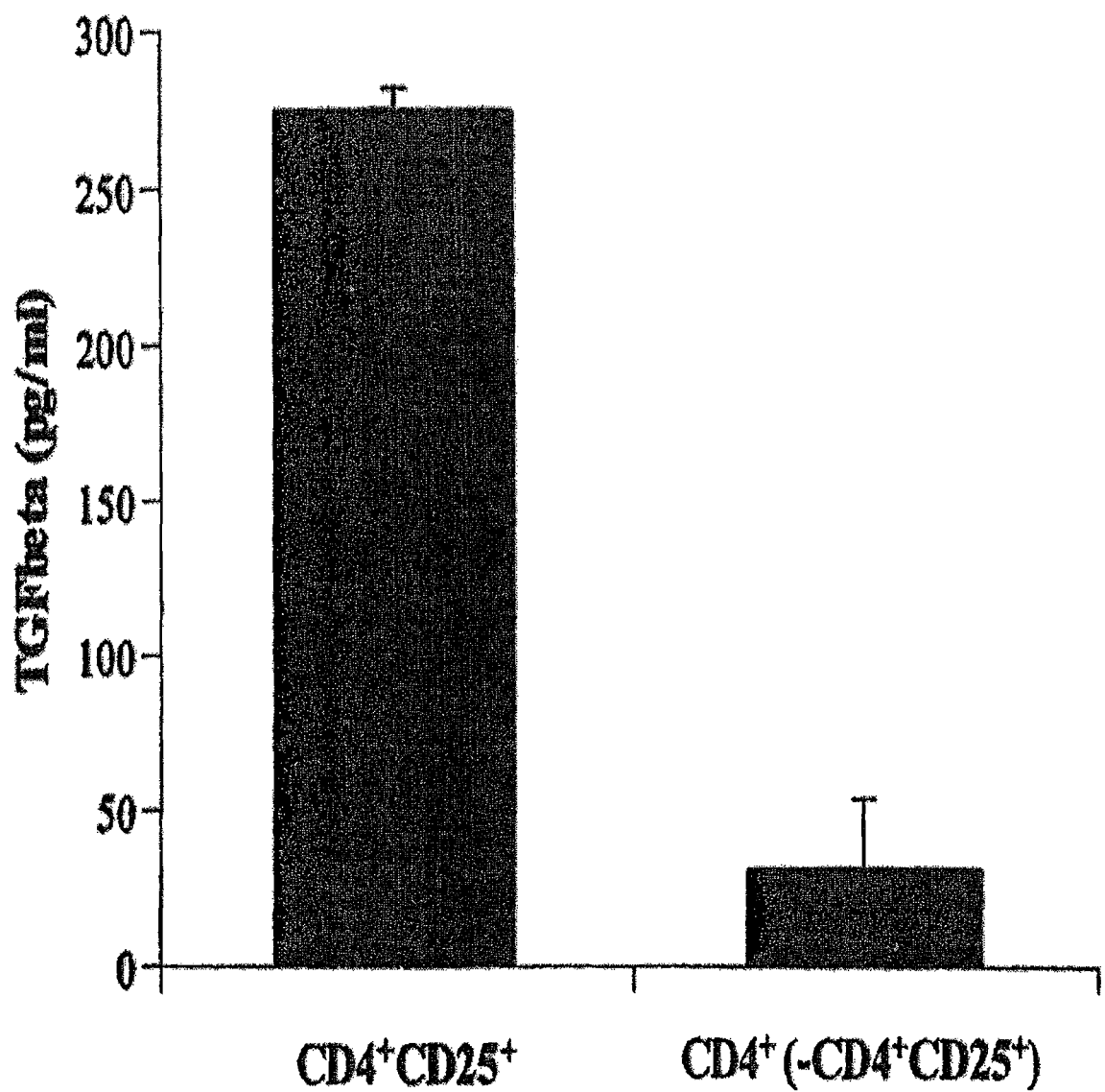
FIGS. 5A and 5B show that constitutive TGF-β secretion by tumor infiltrating CD4+CD25+ cells is not required for inhibition of autologous PBL proliferation.
Figure 5B:
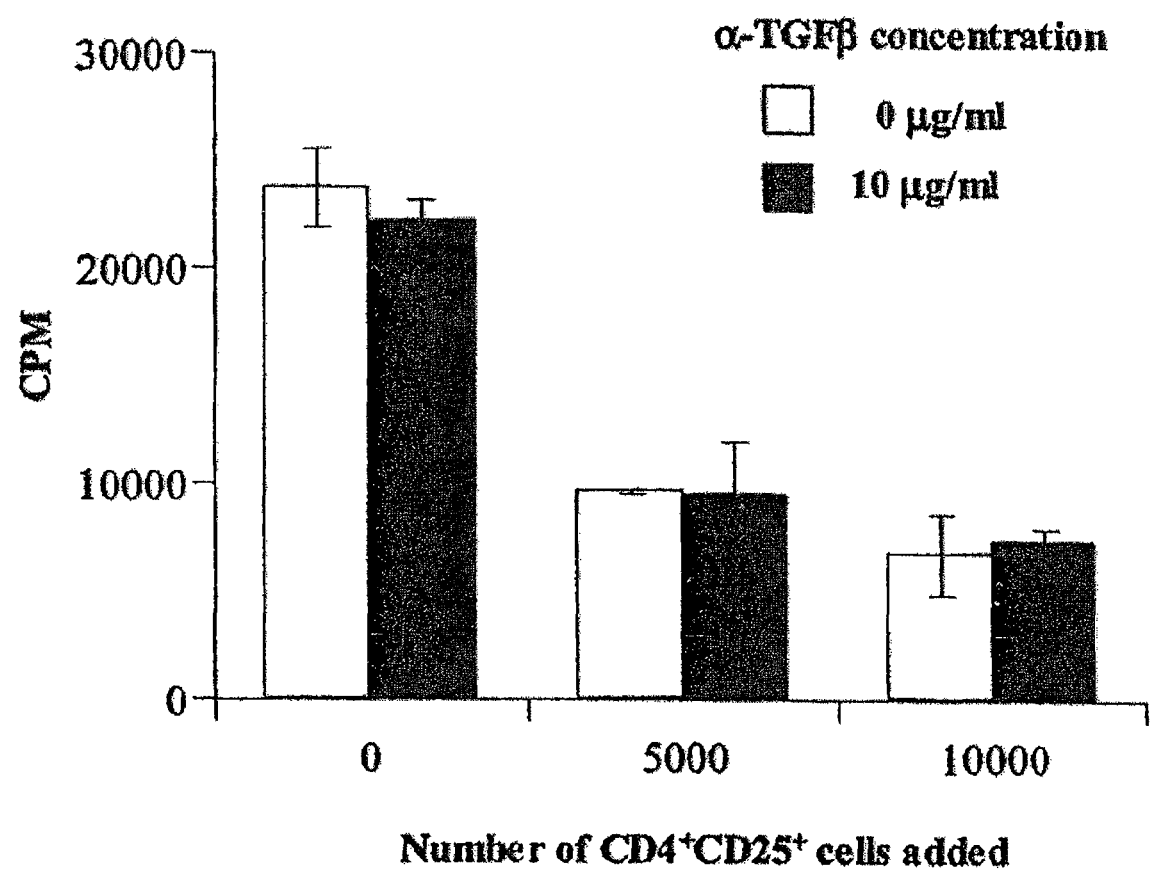

Autologous PBL were cultured alone or with varying numbers of CD4+CD25+ cells and stimulated with plate bound anti-CD3/CD28. Anti-TGF-β neutralizing antibody was added at 0 μg/mL and 10 μg/ml. [$^3$H]thymidine incorporation was measured during the last 18 hours of a 4-day culture. Results were expressed as means of triplicate cultures (±S.E.) for one of two independent experiments with similar results. The addition of 10 μg/mL anti-TGF-β antibody (known to be sufficient to neutralize the effects of 50 ng/mL TGF-β) did not abrogate the suppressive effect of CD4+CD25+ T cells on anti-CD3/28 induced autologous PBL proliferation (FIG. 5B). Accordingly, together FIGS. 5A and 5B show that constitutive TGF-β secretion by tumor infiltrating CD4+CD25+ cells is not required for inhibition of autologous PBL proliferation.

Example 6

Depletion of Immune Regulatory CD4+CD25+ Cells Results in Acceleration of GVHD Mortality In Vivo In prior studies it had been demonstrated that CD4+CD25+ immune regulatory cells are required for the ex vivo induction of tolerance to alloantigen via co-stimulatory blockade (Taylor et al., 2001). Furthermore, the addition of graded numbers of freshly purified B6 CD4+CD25+ cells resulted in the dose-dependent suppression of alloresponses in a MLR composed of B6 CD4+CD25− responders and irradiated bm12 stimulators, while CD25-depletion of CD4+ T cells resulted in a heightened response (Taylor et al., 2001). As a result, the potential role of these professional suppressor cells was investigated in regulating T cell responses to alloantigen and in graft-vs-host disease (GVHD) generation.

To purify whole or CD4+ T cells, in this and the following Examples 7 and 8, using T-cells derived from mice, axillary, mesenteric, and inguinal lymph nodes were mashed, and single cell suspensions were passed through a wire mesh and collected in PBS containing 2% fetal bovine serum (FBS) (HyClone, Logan, Utah). Cell preparations were depleted of NK cells (hybridoma PK136, rat IgG2a) and CD8+ T cells (for CD4+ cell purification) (hybridoma 2.43, rat IgG2b) by incubation with monoclonal antibodies (mAb), followed by passage through a goat anti-mouse and goat anti-rat Ig-coated column (Cellect Cell Enrichment Immunocolumns, Cedarlane, Hornby, Ontario, Canada). The final composition of purified T cells was determined by flow-cytometric analysis to be ≧94% whole or CD4+ T cells.

Where indicated, CD25+ immune regulatory cells were depleted by incubation with anti-CD25 mAb (hybridoma 3C7, rat IgG2b, BD PharMingen (San Diego, Calif.) and sheep anti-rat Dynabeads (Dynal, Lake Success, N.Y.) and determined to be >95% depleted. To enrich for CD4+CD25+ cells, purified CD4+ cells were incubated with anti-CD25 biotin (hybridoma 7D4, rat IgM), followed by streptavidin—PE (both BD PharMingen). After incubation with MACS anti-PE MicroBeads, cells were positively selected on an MS or VS MACS separation column (both Miltenyi Biotec, Auburn, Calif.). Cells were determined to be >90% CD4+CD25+ (also referred to simply as "CD25+ cells.")

Effect of level of irradiation and depletion of CD25+ cells from donor. To determine if depletion of CD25+ cells in a T cell donor inoculum would result in accelerated or increased GVHD mortality in vivo, or whether GVHD mortality was operative under only sublethal total body irradiation (TBI) conditions. B6.C-H2$^{bm12}$/khEg (bm12) (H2$^b$) mice from Jackson Laboratory (Bar Harbor, Me.) were used at 8-12 weeks of age. All mice were housed in a specific pathogen-free facility in microisolator cages. The bm12 recipients were sublethally irradiated (in this particular experiment and throughout the example) by exposing the mice to 6.0 Gy TBI from a $^{137}$Cesium source at a dose rate of 85 cGy/minute, 4 hours prior to cell infusion. The subletally irradiated, bm12 mice were given, in the first experiment 1×10$^5$ class II disparate, whole B6 CD4$^+$ T cells or CD25-depleted B6 CD4$^+$ T cells (FIG. 6A), while in a second experiment, 0.5×10$^5$ of the same whole B6 CD4$^+$ T cells or CD25-depleted B6 CD4$^+$ T cells (FIG. 6B). The cells were administered intravenously.

The mice were monitored daily for survival and weighed twice weekly, as well as examined for the clinical appearance of GVHD. Survival data were analyzed by life-table methods, and actuarial survival rates are shown. Group comparisons were made by log-rank test statistics. P≦0.05 was considered significant. At the higher dose, all mice died of GVHD (FIG. 6A); while at the reduced dose, the survival rate was 20% long term (FIG. 6B; p=0.0068).

Recipients of CD25-depleted CD4$^+$ T cells died of GVHD 1 week to 10 days earlier than recipients of whole CD4$^+$ cells (p=0.024). Because 10$^5$ cells result in a rapid and highly lethal GVHD, the experiment was repeated with a lower cell dose (0.5×10$^5$) in an attempt to magnify the difference in survival (FIG. 6B). All recipients of 0.5×10$^5$ CD25-depleted CD4$^+$ T cells succumbed to GVHD by 19 days after infusion of cells. Therefore, CD25$^+$ cells in the donor T cell inoculum down-regulated GVHD responses, and depletion of CD25$^+$ cells in the donor T cell inoculum accelerated GVHD. Although onset of GVHD was slower in recipients of whole CD4$^+$ T cells, depletion of CD25$^+$ cells of the recipient in vivo pre-transplant, accelerates GVHD.

Figure 7:
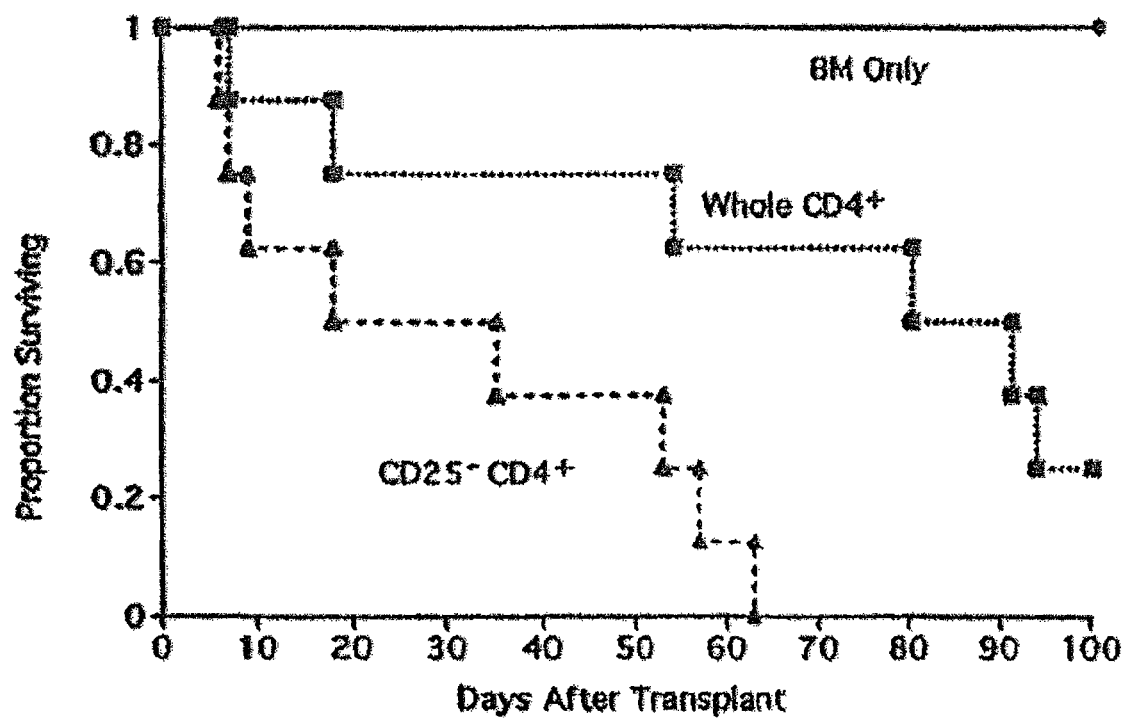
FIG. 7 graphically shows that depletion of CD4+CD25+ cells accelerates GVHD lethality in a different strain combination. Lethally irradiated BALB/c mice were transplanted with B6 BM and either whole CD4+ T cells or CD25-depleted (CD25−) CD4+ T cells. x-axis=days after transplantation. y-axis=proportion of recipients. n=8/group; p=0.016.

Effect on GVHD using T cell-depleted marrow or spleen cells from varied strains. In another series of experiments, BALB/c recipients were lethally irradiated by x-ray on the day prior to transplantation with allogeneic, T cell-depleted bone marrow and either (i) 2×10$^6$ whole spleen or purified whole lymph node CD4$^+$ T cells or (ii) 2×10$^6$ CD-25-depleted CD4$^+$ cells (See, FIG. 7). All recipients of CD25-depleted CD4$^+$ T cells died by day 63 after transplantation (median survival=35 days). In contrast, 25% of mice receiving 2×10$^6$ whole CD4$^+$ T cells survived to day 100 (8 mice/group; median survival=91 days) (FIG. 7, p=0.016).

The effect of CD25 depletion on GVHD generation was tested in 3 different strain combinations in which GVHD was mediated by both CD4$^+$ and CD8$^+$ T cells. BALB/c severe combined immune deficient (SCID) mice (purchased from the National Institutes of Health, Bethesda, Md.) were not irradiated, but were NK-depleted by intraperitoneal injection of 25 µl of anti-asialo GM1 (Wako Chemicals USA, Inc. Richmond, Va.) at 2 and 4 days prior to allogeneic T cell transfer (NK-depleted BALB/c SCID mice). Where indicated, donor-type CD25$^+$ cells were infused by separate intravenous injection.

Figure 8:
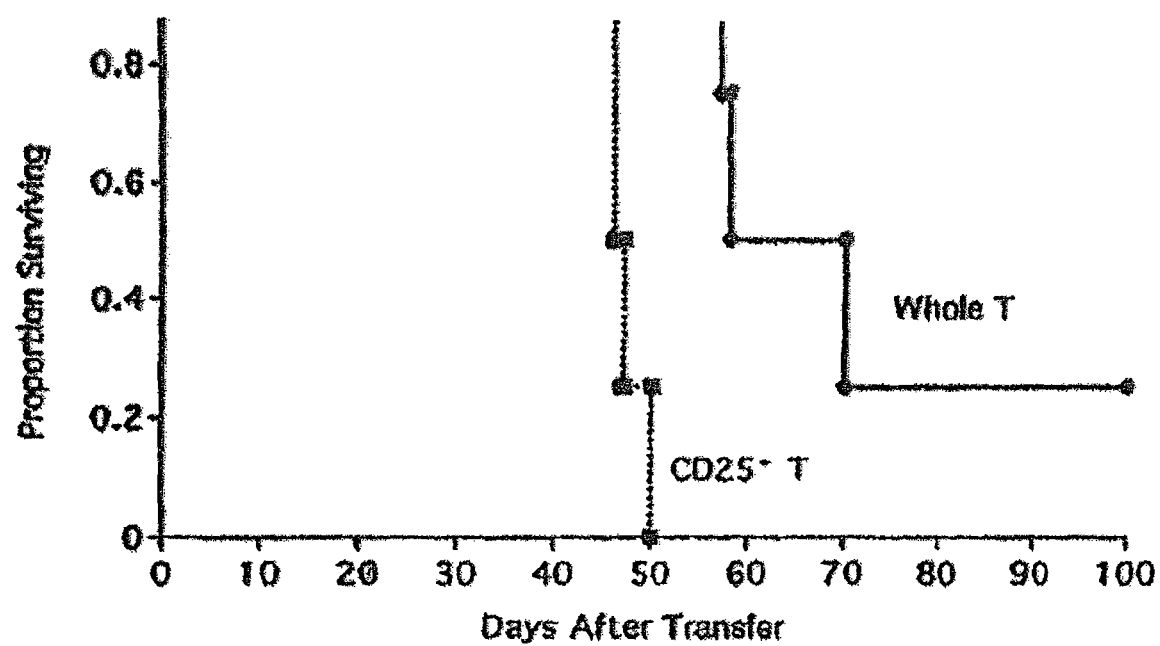
FIG. 8 graphically shows that depletion of CD25+ cells from a whole T cell inoculum accelerates GVHD in a non-irradiated SCID GVHD model. Whole or CD25-depleted B6 T cells were infused into non-irradiated BALB/c SCID mice previously NK-depleted with anti-asialo GM1. x-axis=days after transfer of cells. y-axis=proportion of recipients surviving. n=4/group; p=0.021.

In the first GVHD model, the non-irradiated, NK-depleted BALB/c SCID mice received whole T cells or CD25-depleted T cells (FIG. 8). CD25-depletion of the T cells resulted in an acceleration of GVHD mortality (FIG. 8, p=0.021) indicating that CD4$^+$CD25$^{30}$ cells play a role in GVHD mediated by both CD4$^+$ and CD8$^+$ T cells in the absence of TBI conditioning.

Figure 9:
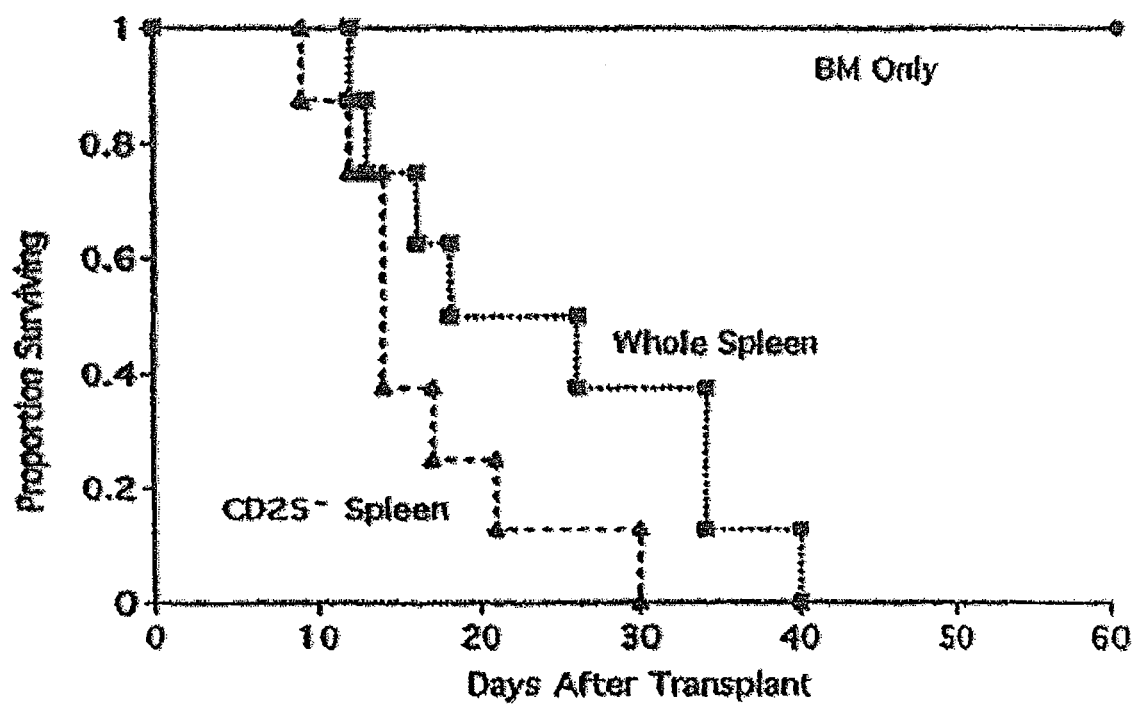
FIG. 9 graphically shows that depletion of CD25+ cells from whole spleen results in an acceleration of GVHD mortality. Lethally irradiated B10.BR mice were transplanted with B6 BM and either 15×10⁶ whole spleen or CD25-depleted spleen. x-axis=days after transfer of cells. y-axis=proportion of recipients surviving. n=8/group; p=0.055.

In a second strain combination, lethally irradiated B10.BR mice (B10.BR (H2$^k$)) from The Jackson Laboratory, Bar Harbor, Me.) received B6 BM and either 15×10$^6$ whole B6 spleen or CD25-depleted B6 spleen cells (FIG. 9). (Note that both B6 and bm12 (both H2$^b$) differ at three amino acids due to mutations in the class II IA region). Recipients of CD25-depleted spleen cells succumbed to GVHD mortality 10 days earlier than recipients of whole spleen cells (p=0.055).

Figure 10:
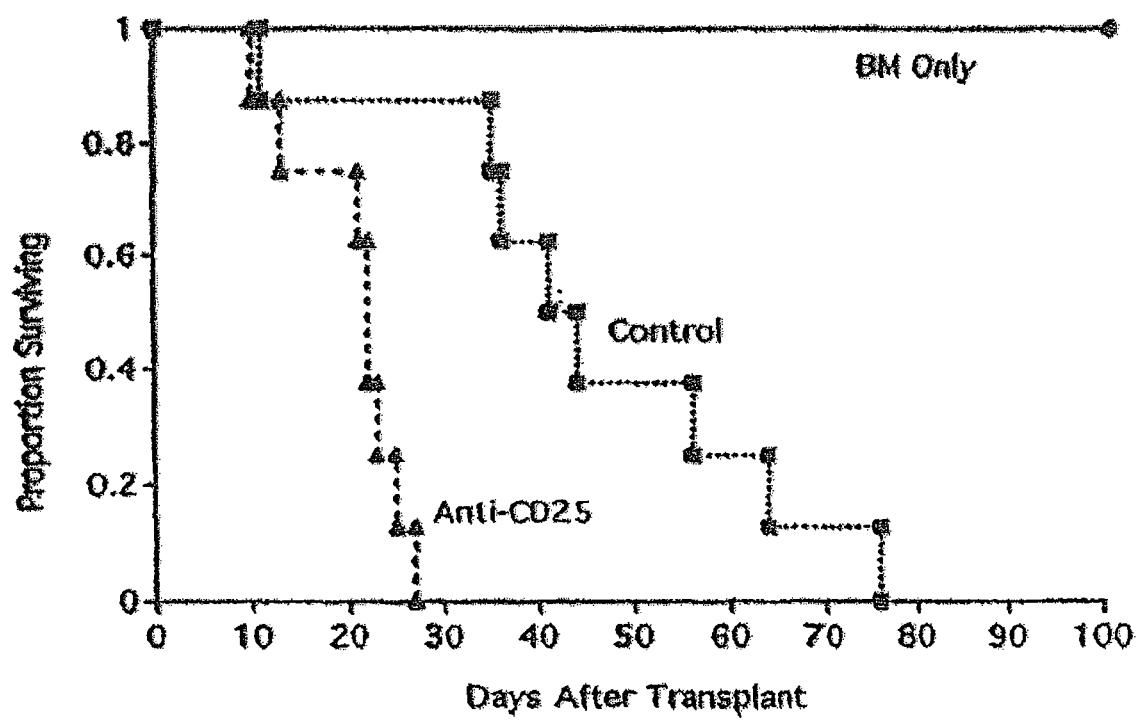
FIG. 10 graphically shows that pre-transplantation in vivo depletion of CD25+ cells accelerates GVHD. Anti-CD25 monoclonal antibody (mAb)-treated or control mAb-treated thymectomized B6 mice were lethally irradiated and transplanted with BALB/c BM and 15×10⁶ spleen cells. Anti-CD25 mAb was administered on days −10, −7 and −4 relative to day of transplantation. x-axis=days after transfer of cells. y-axis=proportion of recipients surviving. n=8/group; p=0.0063.

In a third strain combination, B6 recipient mice were thymectomized prior to transplantation to prevent the emergence of donor BM derived CD4$^+$CD25$^+$ immune regulatory cells after transplantation. Additionally, anti-CD25 mAb (hybridoma 7D4) was administered at a dose of 0.5 mg per injection intravenously on day −10, −7 and −4 relative to day of transplantation (0.5 mg antibody per injection) to these adult-thymectomized recipients pre-transplant to deplete host CD4$^+$CD25$^+$ regulatory cells in vivo. Anti-CD25 mAb was partially purified by ammonium sulfate precipitation of ascites produced in nude mice. Anti-CD25 mAb-treated or control mAb-treated thymectomized B6 mice were lethally irradiated and transplanted with BALB/c BM and 15×10$^6$ whole spleen cells, and survival was monitored (FIG. 10). The mice treated with anti-CD25 mAb in vivo only prior to transplantation had a significantly lower median survival rate as compared to controls (22 vs 44 days). All anti-CD25 mAb-treated recipients succumbed to GVHD mortality by 28 days after transplantation, which was 58 days earlier than recipients of control antibody (FIG. 10, p=0.0063).

Collectively, these data indicate that CD4$^+$CD25$^+$ immune regulatory cells play a significant inhibitory role in GVHD generation, regardless of strain combination or whether GVHD is mediated by CD4$^+$ T cells or by both CD4$^+$ and CD8$^+$ T cells.

Example 7

Infusion of Ex Vivo Activated and Expanded CD4$^+$CD25$^+$ Immune Regulatory Cells Ameliorates GVHD Although previous data indicated that freshly purified CD4$^+$CD25$^+$ cells had only a very modest protective effect on GVHD when administered in a 1:1 ratio with whole CD4$^+$ cells (Taylor et al., 2001), it was hypothesized that the GVHD-protective effect of CD4$^+$CD25$^+$ cells could be clinically exploitable for the inhibition of GVHD lethality. Since CD4$^+$CD25$^+$ cells only account for about 5-10% of the total CD4$^+$ population in both mice and humans, the administration of sufficient numbers of freshly purified immune regulatory cells to be of significant therapeutic benefit may not be clinically practical. However, because data indicate that CD4$^+$CD25$^+$ cells can become more potent suppressor cells upon activation, it was hypothesized that the ex vivo activation and expansion of CD4$^+$CD25$^+$ cells would make immune regulatory cellular therapy clinically feasible. Therefore, to initially determine optimal culture conditions, 4 different conditions were tested for activating the CD25$^+$ cells (i.e., Conditions 1-4), and the effect of each evaluated and the results applied to the remainder of the experiment.

Culturing and Ex Vivo Activation Conditions for Treg Cells

Condition 1: Initial attempts utilized ex vivo incubation of purified CD4$^+$CD25$^+$ cells with soluble anti-CD3 mAb, syngeneic antigen presenting cells (APC), and high dose IL-2 (100 U/ml), as reported by Thornton et al., 2000. Enriched CD25$^+$ cells were suspended at a final concentration of 0.5× 10$^6$ cells/ml in 24-well plates (Costar, Acton, Mass.) and cultured for 1 week. The culture media was DMEM (Bio- Whittaker, Walkersville, Md.) supplemented with 10% FBS (HyClone), 50 mM 2-ME (Sigma, St. Louis, Mo.), 10 mM HEPES buffer, 1 mM sodium pyruvate (Life Technologies, Grand Island, N.Y.), and amino acid supplements (1.5 mM L-glutamine, L-arginine, and L-asparagine) (Sigma) and antibiotics (penicillin, 100 U/ml; streptomycin, 100 mg/ml) (Sigma). Initially, soluble anti-CD3 (0.5 µg/ml) (hybridoma 145-2C11, hamster IgG) (BD PharMingen) and recombinant human IL-2 (5.0 ng/ml) (Amgen, Thousand Oaks, Calif.) was used to activate the cells ("Condition 1").

However, although the activated cells were expanded 10- to 15-fold with this protocol, their suppressor function was significantly impaired. Expanded activated $CD4^+CD25^+$ cells did not suppress GVHD when combined with equal numbers of fresh GVHD-inducing $CD4^+$ T cells (data not shown). Additionally, in contrast to freshly isolated $CD4^+$ T cells, control $CD4^+CD25^-$ cells expanded under the same ex vivo activation protocol failed to mediate lethality when injected into allogeneic recipients indicating that this expansion and activation protocol resulted in a general loss of function in vivo (data not shown).

Condition 2: Next, the $CD25^+$ ex vivo activation protocol was modified using the same culture conditions as above; but, rather than soluble anti-CD3 mAb, the modified protocol utilized immobilized anti-CD3 (5.0 µg/ml and IL-2 (100 U/ml)) ("Condition 2"). After 3 days, the cells were removed from antibody-coated plates, and transferred to fresh plates and fed with IL-2-containing media to permit T-cell receptor- (TCR-) re-expression. They were then expanded in IL-2-containing media for an additional 4 days. This protocol resulted in a 15- to 20-fold expansion of $CD4^+CD25^+$ cells.

The expanded $CD25^+$ cells were evaluated in vivo in C57BL/6 (B6) ($H2^b$), BALB/c ($H2^d$), and BALB/c severe combined immune deficient (SCID) mice (NIH) for their capacity to inhibit GVHD generation. Two million freshly purified B6 $CD4^+$ T cells were infused into non-irradiated, NK-depleted BALB/c SCID recipients. Cohorts of mice received a separate injection of $2\times10^6$ activated $CD4^+CD25^+$ cells or $CD4^+CD25^-$ cells. Cells were activated and expanded by immobilized anti-CD3 mAb and high dose IL-2 for 1 week, and survival and weights were monitored (FIG. 11 and data not shown). The infusion of ex vivo expanded $CD25^+$ cells significantly increased the median survival time from 10 days to 72 days (FIG. 11, p=0.022). Survival in mice receiving supplemental expanded $CD25^-$ cells was not significantly different from control mice receiving only fresh $CD4^+$ T cells (FIG. 11, p=0.285), indicating that the protective effect was specific to the $CD25^+$ population.

Although the administration of activated and expanded $CD25^+$ cells significantly prolonged survival, mice had substantial clinical manifestations of GVHD (20% weight loss, diarrhea, hunched posture, rough poor hair coat and generalized erythema) and did eventually die of GVHD. These data indicated that although $CD25^+$ cells could be expanded considerably ex vivo to obtain sufficient numbers to significantly inhibit GVHD, additional improvements in the activation and expansion protocol were needed to increase the anti-GVHD effect.

Comparative experiment: To optimize the method of activating and culturing B6 $CD25^+$ cells, three different methods were compared. The standard for comparison was the Condition 2 activation protocol, meaning activation via (i) immobilized anti-CD3 and (ii) high dose IL-2 (100 U/ml) as described above. All cultures were >95% viable.

Condition 3: Because immobilized antibody can result in strong TCR signaling and activation-induced cell death (Lenardo, *Nature* 353:858-861 (1991); Wesselborg et al., *J. Immunol.* 150:4338-4345 (1993); Lissy et al., *Immunity* 8:57-65 (1998); Carpenter et al., *J. Immunol.* 165:6205-6213 (2000)), there was a need to test a less potent and global means of activation. Thus, in "Condition 3," irradiated BALB/c splenic stimulators were added to purified B6 $CD25^+$ cells (at a 2:1 ratio), to induce more physiological levels of TCR signaling and activation, and the cells were cultured in the presence of high dose IL-2 (100 U/ml).

An important part of the evaluation of the culturing conditions was the recovery data as the clinical feasibility of this approach was dependent on being able to infuse sufficient numbers of activated $CD25^+$ regulatory cells. The Condition 3 culture protocol, utilizing immobilized anti-CD3 and high dose IL-2, resulted in a 12-fold expansion of cells in 1 week, whereas irradiated allogeneic host-type splenic stimulators to trigger the T-cell receptor for activation, and high-dose IL-2 led to only a 1.5-fold expansion of cells.

Condition 4: Recognizing that although a relatively high dose of IL-2 might be required for optimal expansion, withdrawal from high dose IL-2 could be contributing to poor cell survival upon transfer in vivo, thereby potentially resulting in less than optimal GVHD protection, there was a further reason to test "Condition 4" (Lenardo, 1991). Condition 4 utilized irradiated BALB/c splenic stimulators and low dose IL-2 (reduced to 10 U/ml), and recombinant human transforming growth factor-$\beta_2$ (TGF-$\beta_2$; 1.0 ng/ml) (R&D Systems) was added as an additional growth factor for $CD4^+CD25^+$.

The Condition 4 method, utilizing allogeneic splenic stimulators, low dose IL-2 and TGF-$\beta$ resulted in the lowest recovery, with only 31% of input cells recovered at 1 week.

All 3 types of cultured $CD25^+$ cells ($CD4^+$; $CD4^+$+activated $CD25^-$; $CD4^+$+activated $CD25^+$) were evaluated for their ability to inhibit GVHD mediated by both $CD4^+$ and $CD8^+$ T cells (FIG. 12). Six BALB/c SCID mice received $10^6$ CD25-depleted whole T cells to induce GVHD. Two separate cohorts of mice (6 mice per group) also received $10^6$ $CD25^+$ cells cultured under each of the first 2 conditions (anti-CD3/IL-2 (Condition 2, shown as open boxes in FIG. 12) or allo-APCs/IL-2 (Condition 3, shown as open triangles in FIG. 12)). A third cohort (6 mice per group) received $10^6$ $CD25^-$ depleted whole T cells and $0.5\times10^6$ $CD25^+$ cells cultured with irradiated BALB/c splenocytes, low dose IL-2 and TGF-$\beta$ (Condition 4, shown as stars in FIG. 12); however, insufficient recovery in this group did not permit the full infusion of $10^6$ $CD25^+$ cells.

All recipients of $CD25^-$ T cells died within 8 days after transfer of cells (FIG. 12). In contrast, the infusion of cultured $CD25^+$ cells significantly inhibited GVHD mortality regardless of culture protocol. Fifty percent (3/6) of recipients of fresh $CD25^-$ T cells and $CD25^+$ cells expanded by immobilized anti-CD3 mAb and high dose IL-2 were alive 2 months after the transfer of cells. Survival was prolonged in recipients of $CD25^-$ T cells and $CD25^+$ cells cultured with BALB/c splenocytes and high dose IL-2, but all mice died of GVHD by day 54 (median survival was 31 days) (FIG. 12). All p values $\geq 0.016$ compared to control group (shown as closed circles in FIG. 12).

Despite the lower cell number infused, $CD25^+$ cells cultured under this protocol protected 5 of 6 recipients against GVHD lethality for at least 2 months. Together these data demonstrate that $CD4^+CD25^+$ cells can easily be expanded ex vivo in sufficient numbers to provide significant protection against rapidly lethal GVHD.

Figure 13:
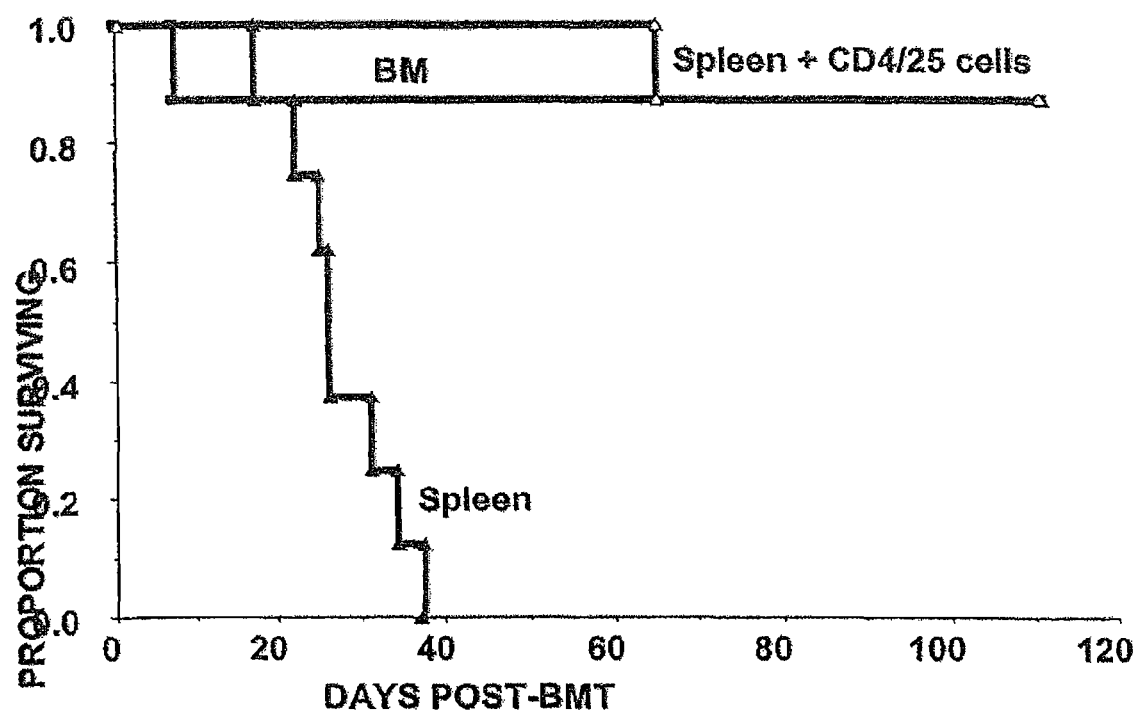
FIG. 13 graphically shows that multiple infusions of activated and expanded CD4$^+$CD25$^+$ cells suppress GVHD mortality in lethally irradiated recepients of full, MHC-disparate donor grafts.

GVHD Therapy after onset of GVHD symptoms: To determine whether the activated and expanded $CD25^+$ Treg cell infusion could be used to treat GVHD, lethally irradiated B10.BR recipients were given C57BL/6 BM alone or BM and splenocytes on day 0. On day 6 post-BMT, at which time there was clear onset of GVHD symptoms, including GVHD-induced weight loss in groups receiving splenocytes, indicative of active and ongoing GVHD, a single infusion of activated and expanded (anti-CD3/IL-2/TGF-β) C57BL/6 CD4$^+$CD25$^+$ cells was administered intravenously. Nine-10 mice per group were transplanted and analyzed. The infusion of activated and expanded CD4$^+$CD25$^+$ cells was able to rescue 40% of mice long-term (152 days) as compared to uniform lethality by day 51 in the control group (P=0.002 in spleen+CD4/25 vs spleen alone) (See, FIG. 13).

Consequently, of the anti-GVHD therapies tested to date, methods utilizing ex vivio activated and expanded CD25$^+$ Treg cell infusions, appears to be the most promising as assessed in the present model systems.

Figure 14:
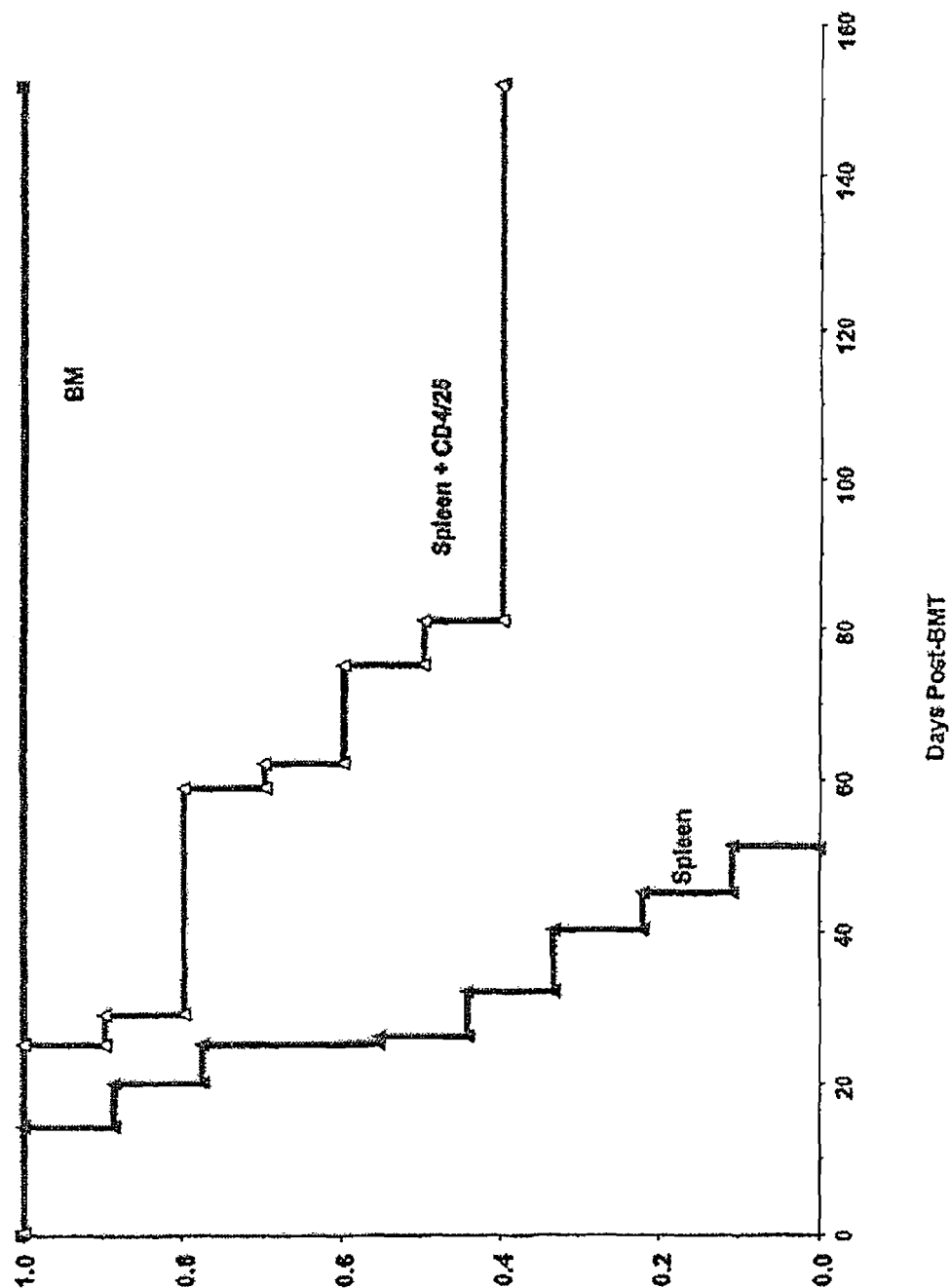
FIG. 14 graphically shows that after the onset of GVHD, a single infusion of activated and expanded CD4$^+$CD25$^+$ cells rescued 40% of the lethally irradiated recepients from GVHD mortality long term (for a period at least 3-fold longer than the control group).

Multiple cell infusions for GVHD prevention: In addition to the anti-GVHD effect shown by infusing activated and expanded CD4$^+$CD25$^+$ cells infused into non-irradiated SCID recipients of allogeneic donor T cells, a potent anti-GVHD lethality effect was observed in lethally irradiated B10.BR recipients of full major histocyte compatibility-disparate (MHC-disparate) C57BL/6 splenocytes (15×10$^6$) along with C57BL/6 T cell depleted bone marrow (BM). Activated and cultured (anti-CD3/IL-2/TGF-β) CD4$^+$CD25$^+$ cells were infused into a cohort of mice, as indicated, on day 0 and day 4 (10$^7$/day) post-BMT in this model system (spleen+CD4/25 cells). Controls consisted of BM alone or BM and supplemental splenocytes without CD4/CD25 cell infusions. Eight mice per group were transplanted. Whereas uniform GVHD lethality was seen in the control animals, recipients of two infusions of CD4$^+$CD25$^+$ cells had low mortality with 88% surviving long-term (See FIG. 14). Accordingly, these data indicate that multiple cellular infusions are non-toxic, do not cause GVHD, and in fact are highly effective in preventing GVHD mortality in lethally irradiated recipients of full MHC-disparate donor grafts.

Consequently, because the CD4$^+$CD25$^+$ cells can be expanded and administered as multiple infusions, these data provide proof-of-principle for acute and chronic GVHD therapy trials in which multiple cell infusions can be given to patients from a single donor CD4$^+$CD25$^+$ cell isolation procedure to the marked expansion observed with ex vivo activated and culture of this cell population which is present in relatively low frequencies in humans.

Engraftment effects: To test the engraftment facilitating capacity of expanded C57BL/6 CD4$^+$CD25$^+$ cells, anti-CD3/IL-2/TGFβ was used either alone or with survival factors (IL-4; IL-7). BALB/c recipients were given 4.25 Gy TBI and C57BL/6 T cell depleted BM (10$^7$ cells per recipient) along with either no CD4$^+$CD25$^+$ cells or with activated, expanded CD4$^+$CD25$^+$ cells (5×10$^6$). Mean donor cells were: control (41%) as compared with CD4$^+$CD25$^+$ cells: 89% (P=0.0003) or 83% (P=0.009), respectively, for the two types of expansion cultures. Engraftment was multi-lineage and stable over time (repeat testing was done on days 82 and days 139 with similar results). Recipients had no evidence of side-effects (including GVHD), and survival was comparable (~75% long-term) in all groups. Therefore, the expanded cultures can facilitate engraftment.

Use of activated and expanded CD4$^+$CD25$^+$ cells enriched for L-selectin: Thorton et al., 2000 teach that L-selectin high cells are not more potent than L-selectin low cells, and more recently, Fu et al. report in *Amer. J. Transplant* 4:65-78, 2004 that there is no in vivo difference in the biological efficacy of freshly isolated CD4/25 L-selectin high versus low cells in preventing autoimmune gastritis upon adoptive transfer in vivo.

Nevertheless, to determine whether homing receptor expression influenced the anti-GVHD effects of activated and expanded CD4$^+$CD25$^+$ cells, C57BL/6 CD4$^+$CD25$^+$ cells were cultured using anti-CD3 anti-CD28 mAb coated beads (2 days)+IL-2 (100 U/ml). After 7 days, activated and expanded cells were enriched for L-selectin (CD62L) high (hi) or low (lo) levels of expression by column purification. Lethally irradiated bm12 mice (C.H2bm12 (B10.BR(H2$^k$)) were given MHC class II disparate C57BL/6 T cell depleted BM alone (BM) or with supplemental C57BL/6 CD4$^+$CD25$^-$ T cells (10$^6$ cells per recipient). Some cohorts of recipients receiving donor T cells were given ex vivo activated and expanded CD4$^+$CD25$^+$CD62L-hi or CD4$^+$CD25$^+$CD62L-lo cells (3×10$^6$ cells per recipient). Controls consisted of BM alone (BM), or BM with C57BL/6 CD4$^+$CD25$^-$ cells alone (BM+CD4$^+$CD25$^-$ cells). Eight mice per group were transplanted. As of day 35 post-BMT, controls receiving donor CD4$^+$CD25$^-$ T cells without CD4$^+$CD25$^+$ cells had only a 25% survival rate. Recipients that received CD4$^+$CD25$^+$CD62L-lo cells had a 38% survival rate, which was not significantly different (P=0.35) from those not receiving this supplemental cell population.

In marked contrast, recipients receiving CD4$^+$CD25$^+$CD62L-hi cells isolated after ex vivo activation and culture had a significantly higher survival rate (100%) as compared to those receiving no supplemental CD4$^+$CD25$^+$ cells (P=0.0016) or those receiving CD4$^+$CD25$^+$CD62L-lo cells (P=0.005). Thus, there is a major benefit to the in vivo infusion of CD4/25 L-selectin high versus low cells that have been expanded with CD3/28 beads+IL-2 in suppressing GVHD lethality. These data further confirm that ex vivo activated and cultured cells can be subdivided into cell subsets that contain the potent anti-GVHD effects in rodents, and that this procedure, performed after ex vivo activation and expansion, can further improve upon the biological properties of this cell population in BMT models. CD62L expression levels provide one such approach to accomplish this goal, but others are known or will be defined in the art.

The present data prove that ex vivo activated and expanded CD4$^+$CD25$^+$ cells provide both potent GVHD suppression and/or inhibition and engraftment promoting effects when infused into allogeneic recipients using a variety of models. Studies in human cells have demonstrate an in vitro phenomenon that CD4$^+$CD25$^+$ cells can be activated and expanded, while at the same time retaining suppressive capacity to alloantigens.

Example 8

Methods for Ex Vivo Culture-Expanding, Stringently Isolated Treg Cells, and Cells Provided Thereby for Use in Immunosuppressive Therapies in Humans Based upon the foregoing mouse studies and previous studies, as reported by Taylor et al., 2002, supra, ex vivo polyclonally expanded Treg cells, with anti-CD3 plus IL-2 (for 10 days), are shown herein to be effective in preventing GVHD Studies by others have shown that ex vivo expansion of Treg cells with irradiated allogeneic APCs plus exogenous IL-2 can suppress GVHD (Cohen et al., 2002, supra; Trenado et al., 2002, supra), while subsequent studies have shown that Treg cells can prevent GVHD, but that in animal models they still allow for anti-tumor or graft versus leukemia (GVL) effects (Trenado et al., 2002; Jones et al., 2003; Edinger et al., 2003, supra). Nevertheless, clearly the potential role of human Treg cells in clinical immunosuppressive therapy in human transplantation, was limited unless, and until, methods could be developed whereby human Treg cells could be isolated and culture-expanded over a long enough time to provide sufficient numbers of cells for in vivo infusion.

To meet this need, taking advantage of natural physiological mechanisms for down-regulating immune responses the inventors have developed unique purification methods and ex vivo culture-expansion techniques that provide activated human $CD25^+$ suppressor T cells for immunosuppressive therapies, particularly for the prevention of transplantation related immune reactions. Human suppressor cell lines were generated in the experiments that follow, which maintained function for at least 3-6 weeks. In some cases, cell lines in culture remained functional for up to 3 months, and were still potently suppressive. However, to better characterize $CD4^+$ $CD25^+$ Treg cell function, an improved modified MACS purification method was developed to isolate and culture-expand these important cells. The following components and methods were used in the experiments described below, resulting in the potent culture-expanded Treg cells capable of providing marked suppressive effects for therapeutic purposes.

MACS purification of $CD4^+$ T cell subsets. T cells were isolated from buffy coat preparations derived from the whole blood of normal healthy volunteer donors (Memorial Blood Centers, Minneapolis, Minn.) (leukophoresis products were also used in some early experiments). Leukocyte rich buffy coat cells were centrifuged over ficoll-hypaque layers to collect PBMC. $CD25^+$ bright cells were isolated by positive selection from PBMC with directly conjugated anti-CD25 magnetic microbeads (2 μl per $10^7$ cells) (Miltenyi Biotec, Auburn, Calif.), and purified over an $LS^+$ column ($LS^+$ separation columns and MidiMACS Separation unit instrumentation are available from Miltenyi Biotec). Cells were then applied to a second magnetic column, washed, and re-eluted. After the double column procedure, cells were routinely >93% pure (for CD25) by FACS analysis (a few B cells (4-8%) and CD8+ T cells (~1%) constituted the remainder).

Alternatively, cells were indirectly stained with anti-CD25-FITC, clone 2A3 (Becton Dickinson Immunocytometry Systems, San Jose, Calif.), washed and bound to anti-FITC multi-sort microbeads (3 microliters per $10^7$ cells, Miltenyi Biotec) and positively selected. As with the direct microbead system, cells were reapplied to a second column. After column purification, multisort beads were detached, and the $CD25^+$ cells were depleted of CD8, CD14, CD19, CD20, and CD56 expressing cells with a cocktail of mAb-coated microbeads for lineage depletion.

The non-CD25 fraction of PBMC was further depleted of $CD25^+$ cells with more anti-CD25 microbeads (10 microliters per $10^7$ cells). $CD4^+$ T-cells were then isolated from the CD25– fraction by positive selection with anti-CD4 mAb-coated magnetic microbeads (10 microliters per $10^7$ cells) (Miltenyi Biotec). Cells were routinely 96-98% pure $CD4^+$ $CD25^+$ by FACS analysis.

Culture of T cells. Isolated CD4+CD25+ cells or control CD4+CD25– cells were cultured with anti-CD3/CD28 mAb-coated Dynabeads (U. Pennsylvania) (Levine et al., *J. Immunol.* 159(12):5921-5930 (1997), Laport et al., *Blood* 102(6): 2004-2013 (2003)) at a (2:1) bead/total cell ratio. $CD4^+$ $CD25^-$-feeder cells were irradiated at 30 Gy and added at a 1:1 ratio to $CD4^+CD25^+$ cells. Cells were cultured at 1 million (non-irradiated) cells/ml in 24 well plates. IL-2 was added on day 3 at 50 IU/ml (Chiron, Emeryville, Calif.). Cells were split as needed, approximately 1:3 every 3 days during fast growth phase. Culture media was RPMI-1640 (Gibco) supplemented with 10% FCS (Gibco), L-glutamine, penicillin, and streptomycin.

Stimulator cells for MLR cultures. Immature human dendritic cells (DC) were generated from CD14+ monocytes (Sallusto et al., *J. Exp. Med.* 179(4):1109-1118 (1994), Banchereau et al., *Annu. Rev. Immunol.* 18:767-811 (2000)), isolated from PBMC, by magnetic bead based purification (Miltenyi-Biotec), and were cultured in X-Vivo-15 (Bio-Whittaker, Walkersville, Md.) media at $10^6$ cells per ml supplemented with GMCSF (50 ng/ml final) and IL4 (20 ng/ml final) cytokines from (R&D Systems, Minneapolis, Minn.). Cells were cultured for 5-10 days before use as stimulators in MLR.

For some experiments, DC were matured with TNF-alpha (20 ng/ml final) and Poly I:C, a Toll-like receptor (TLR)-3 agents agonist ligand (20 μg/ml final) (Sigma, St. Louis, Mo.) for two days (Cella et al., *J. Exp. Med.* 189(5):821-829 (1999), Spisek et al., *Cancer Immunol. Immunother.* 50(8): 417-427 (2001), Godfrey et al., *Blood* 103:1158-1165 (2004)). In other experiments, the TNF and PolyIC (at the same concentrations), or LPS (Sigma-Aldrich) (10-100-1000 ng/ml) were added directly to MLR. DC stimulators were irradiated at 30 Gy.

MLR Assay Culture. $5 \times 10^4$ responding $CD4^+CD25^-$ T-cells and $5 \times 10^3$ DC stimulator APC were cultured per well in 96 well U-bottom plates. Test cultured suppressor or conventional T-cell lines were added at $2.5 \times 10^4$ per well for standard assays, or in graded numbers for titration experiments. For antibody blocking experiments, $1 \times 10^4$ suppressor cells were used. Culture media was RPMI-1640 (Gibco-Life Technologies, Grand Island, N.Y.) supplemented with 10% FCS (Gibco), L-glutamine, penicillin, and streptomycin. Wells were pulsed on days 3, 5, 6, and 7 with $^3$H-thymidine for the last 16 hours of culture. All timepoints had 6 replicates. Results were expressed in counts per minute. However, data were collected with direct beta counter, hence the reported cpm were lower than typically reported with liquid scintillation amplification. Thus, although the absolute magnitude of counts is lower, the comparative differences between experimental samples remained the same.

Cytokine Analysis. Culture supernatants were spun free of cells and aliquots were frozen at –80° C. Supernatants were evaluated by the Luminex assay system with a latex bead-based multi-analyte system (R&D Systems, Minneapolis, Minn.).

Cytotoxicity. Cultured suppressor cell lines were tested for cytotoxicity against allogeneic DC or the NK sensitive cell line K562 in 4-hour $^{51}$Cr release assays. Effector to target ratios ranged from 20:1 to 0.6:1. Target cells were labeled with 200 μCi Sodium Chromate-$^{51}$Cr (DuPont, Wilmington, Del.) for 60 minutes. All determinations were performed in triplicate, and the percentage of lysis was determined. Positive control lytic NK92 cells were obtained from the ATCC (American Type Culture Collection, Rockville, Md.) and maintained in the presence of 500 U/ml recombinant human IL-2 (Chiron).

Monoclonal antibodies (Mabs). To follow purification, cells were stained with an anti-CD25-PE, which is not blocked by anti-CD25-microbeads, clone M-A251 (BD Pharmingen). Other antibodies for flow cytometry included anti-CD4-PerCP (clone SK3), anti-CD8-PerCP (SK1), anti-CD19-APC (4G7) from (Becton Dickinson Immunocytometry Systems); anti-CD27-FITC (MT271), anti-CD62L-PE (Dreg 56), anti-CD69-FITC (FN50), anti-CD152-PE (BNI3), anti-CD122-PE (Mik-b2), anti-CD132-PE (AG184), and anti-CD134 (ACT35) from (BD Pharmingen); and anti- CCR7-PE (#150503), and anti-GITR-PE (#110416), from (R&D Systems). In functional experiments aimed at blocking suppression, neutralizing antibodies were used at titered amounts up to 20 μg/ml. Antibodies included anti-IL-10 (23738), anti-IL-10-Receptor-alpha (37607), and anti-TGFβ-1,2,3 (1D11), from (R&D Systems).

Flow Cytometry. For immunofluorescence staining, cells were stained for 30 min at 4° C., with titered amount of each antibody. Cells were washed again and analyzed on a FACS Calibur cytometer (BD Immunocytometry Systems). Cell lines subsets were sorted on a FACS Vantage. Data was analyzed by FloJo software version 4.4 (Treestar, Ashland, Oreg.). Intracellular staining was done using paraformaldehyde fixed cells, 2% at room temperature for 30 minutes, followed by permeabilization and staining for 1 hour, and washing in 0.1% saponin containing buffer, PBS plus 5% FCS-5% human AB serum.

Statistics. All error bars on FIGS. 15-21 represent one standard deviation above and below the mean. A paired, two tailed Students t-test was used to determine the statistical significance of differences between proliferative responses. Values of p<0.05 were considered significant.

Figure 15A:
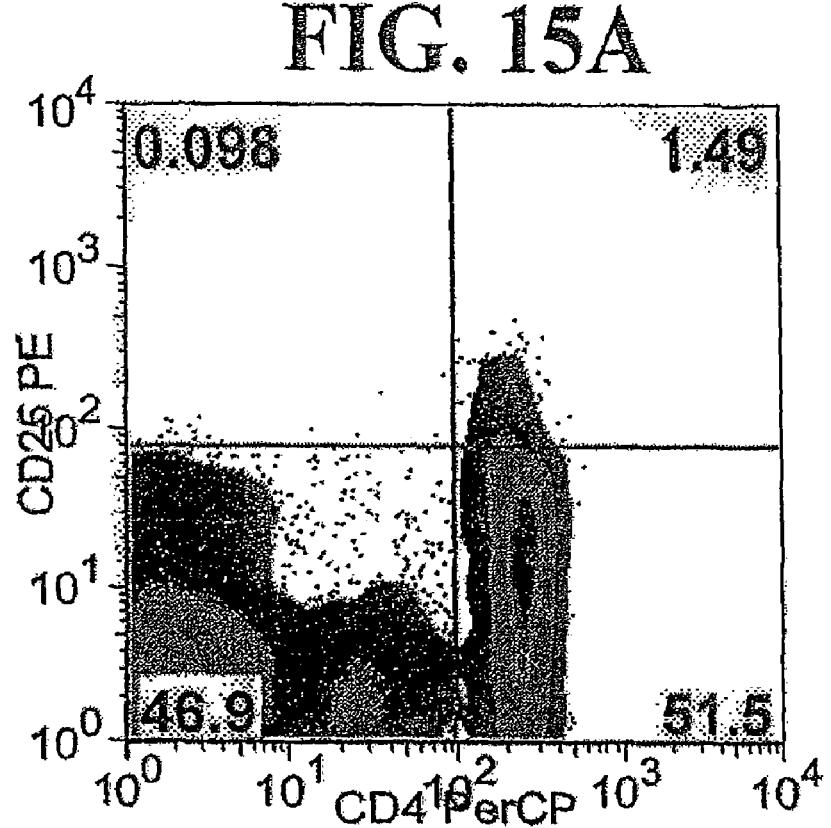
Figure 15B:
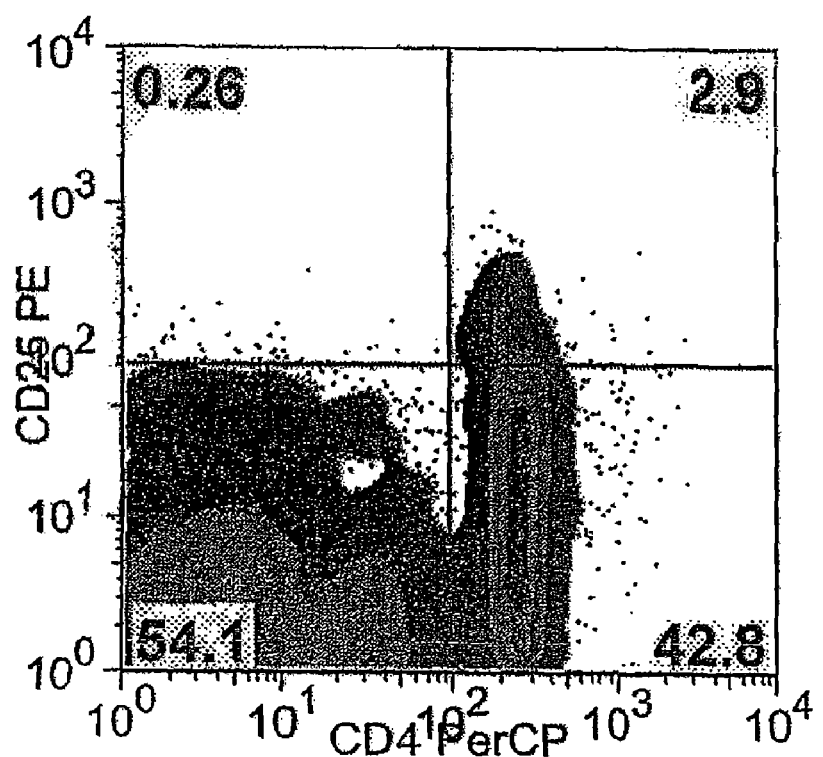

Experimental Results. Using a lower titer of anti-CD25 mAb-coated microbeads in the present modified MACS purification led to isolation of cells with higher mean channel fluorescent intensity of CD25 expression. In addition, reapplication of the magnetically isolated cells, to a second column for additional purification further increased the enrichment of $CD25^+$ cells. The use of cleavable microbeads allowed for removal of beads after CD25 purification, which then permitted subsequent lineage depletion (of CD8, CD14, CD19, and CD56 cells). This strategy led to the generation of a highly purified $CD4^+CD25^+$ cell populations (FIG. 15C). The CD25 negative fraction of the cells was further depleted of $CD25^+$ cells, and used as the source for purification of the $CD4^+CD25^-$ cells, for isolation of conventional T cell controls (FIG. 15D).

Anti-CD3/CD28 beads and IL-2 facilitate Treg cell expansion. Human $CD4^+CD25^+$ Treg cells are hyporesponsive to stimulation with anti-CD3 mAb or DCs. However, they can proliferate when given these stimuli plus IL-2 or IL-15, albeit to a much lower extent than $CD4^+CD25^-$ T-cells (Jonuleit et al., 2001, supra, Dieckmann et al., 2001, supra)). Accordingly, in the initial experiments, purified $CD4^+CD25^+$ cells were expanded with immobilized anti-CD3 plus IL-2, which allowed for a 5-10-fold expansion over two weeks.

Figure 16A:
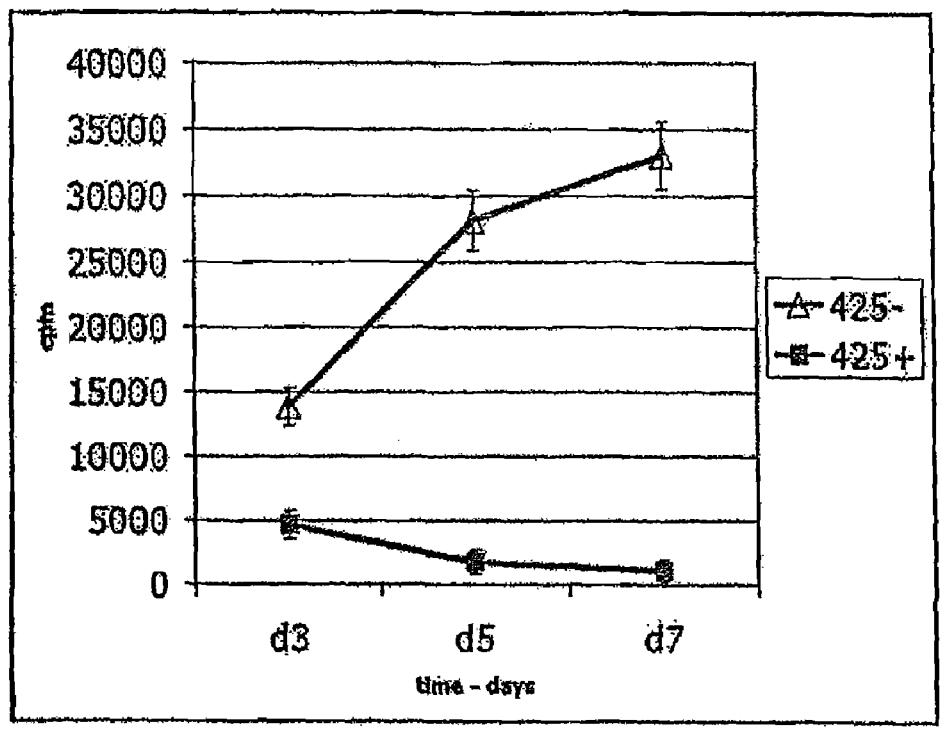
FIGS. 16A-16C graphically depict the expansion of CD4$^+$CD25$^+$ suppressor cell lines in terms of proliferation of CD4$^+$CD25$^+$ cells in short term assays, and accumulation in long term cultures.
Figure 16B:
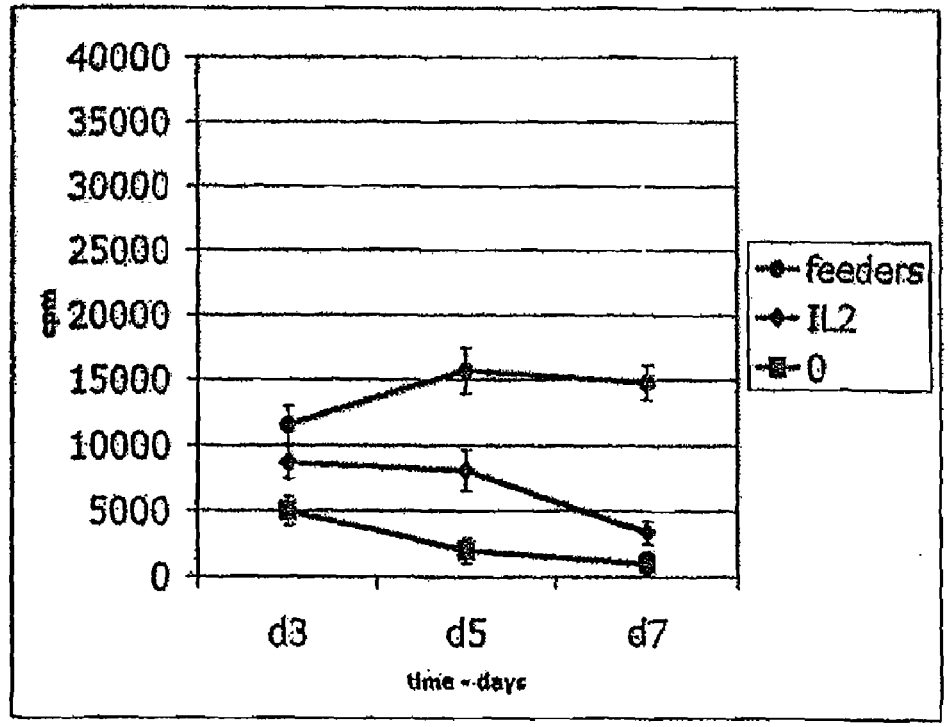

To further augment expansion potential, a costimulatory molecule based stimulation was investigated. To do this, cell-sized Dynabeads were used with anti-CD3 and anti-CD28 mAbs covalently attached (3/28 beads). This reagent has been used successfully for clinical scale expansion of conventional T cells for immunotherapy trials (Levine et al., 1997, Laport et al., 2003), and has enabled greater than 1 million fold expansion of T cells. Quite dramatically however, it was discovered that the stringently purified $CD25^+$ Treg cells proliferated poorly with stimulation with the 3/28 beads alone. This contrasts with the vigorous response generated by the $CD4^+CD25^-$ cells (FIG. 16A). The weak response of $CD4^+CD25^+$ cells, however, was significantly augmented by IL-2 supplementation, and this combination was sufficient for modest Treg expansion from most donors (FIG. 16B). Nevertheless, the more stringently the $CD4^+CD25^+$ cells were purified, the less well they grew in culture, even with stimulation with 3/28 beads and IL-2.

Because $CD4^+CD25^+$ T cells appear to have cytokine production defects, it was concluded that conventional T cells could complement this deficiency, and provide for augmented expansion. As a result, irradiated $CD4^+CD25^-$-feeder cells were added to 3/28 bead-stimulated Treg cultures at initiation (1:1 ratio), and were found to provide for a sustained increase in proliferative response (FIG. 16B). This augmentation was significantly greater than that with IL-2 alone at 100 IU/ml. Interestingly, supplementation of Treg cultures with conditioned media (20% v/v) (derived from activated conventional $CD4^+CD25^-$ T cells on day 5 after 3/28 bead stimulation), could largely (but not completely) reproduce the effects of feeder cells. This suggested that the activated conventional T cells produce soluble growth factors for $CD4^+CD25^+$ cell expansion (primarily IL-2, but possibly other factors). Importantly, these feeder-cell supplemented cell lines maintained potent suppressor function. Therefore, with the use of 3/28 beads, IL-2, and $CD4^+CD25^-$-feeders, the $CD4^+CD25^+$ derived cell lines exhibited significant growth, and over 100-fold expansion was readily obtainable.

Figure 16C:
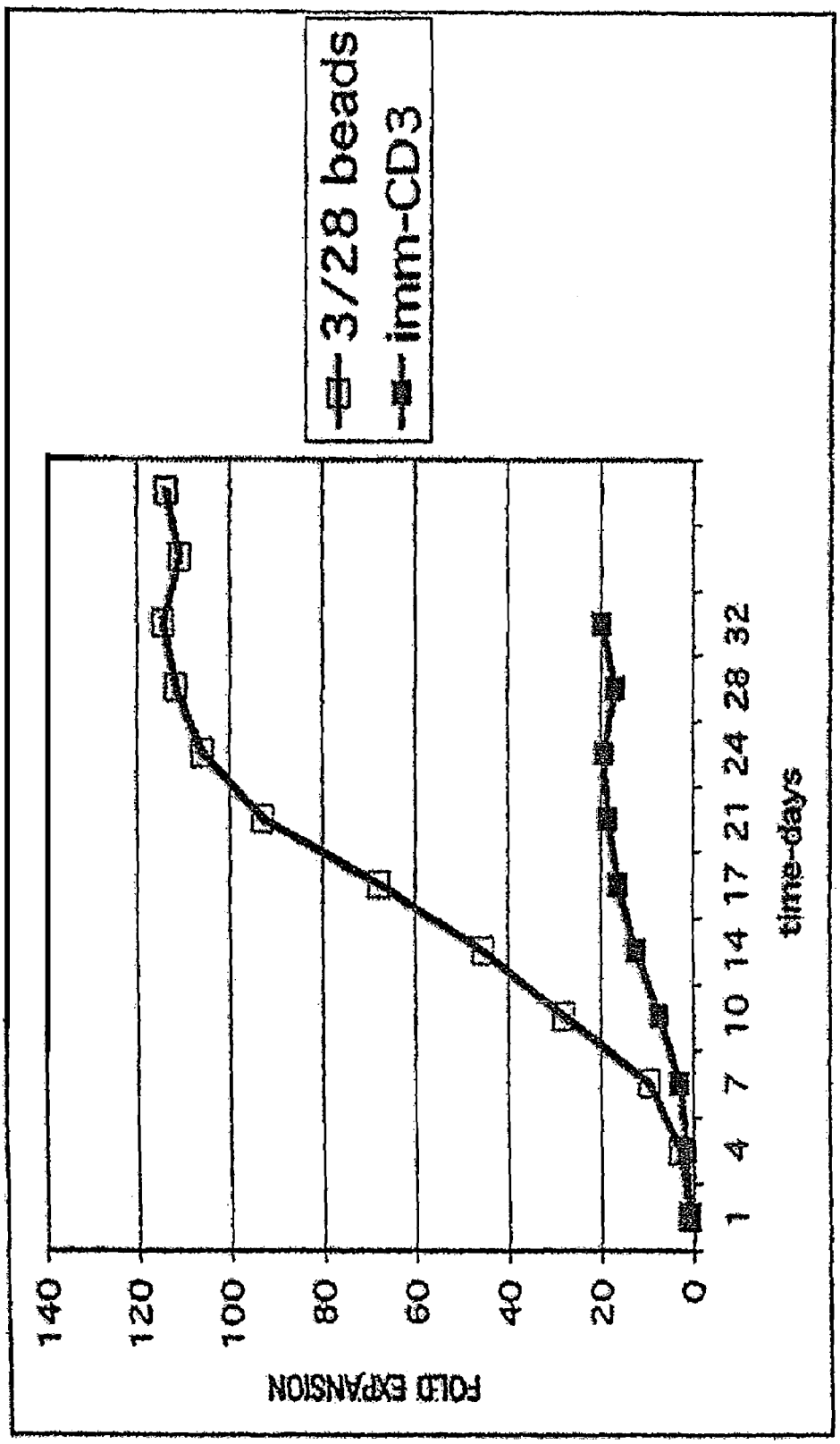

The expansion occurred as a classical sigmoid growth curve, beginning slowly, rapidly expanding over 1-2 weeks, and then reaching a plateau phase (FIG. 16C). After reaching a growth plateau phase, cell lines were maintained in IL-2, and suppressor function was sustained for 3-6 weeks. In some cases cell lines in culture for up to 3 months had potent suppressive activity, however, typically suppressor function diminished over time (not shown).

Functional Assessment of $CD4^+CD25^+$ Suppressor cell lines in MLR Assays. All cell lines were initially screened for suppressor activity in MLR after 2-3 weeks of culture, and then further analyzed over the next 3-4 weeks. To evaluate suppressor function, an HLA-mismatched allo-MLR assay was used as a functional readout. Purified freshly isolated $CD4^+CD25^-$ responding T-cells were reacted with irradiated immature DC from unrelated donors. Test cells (cultured $CD4^+CD25^+$ and $CD4^+CD25^-$ derived cell lines) were added to the MLR at day 0 with a regulator/responder ratio of (1:2). Suppression was reflected by decreased proliferation, and was most evident on day 6-7, peak of control MLR. These assays are very robust and consistent among donors, and therefore served as the present standard measure of suppression.

Figure 17A:
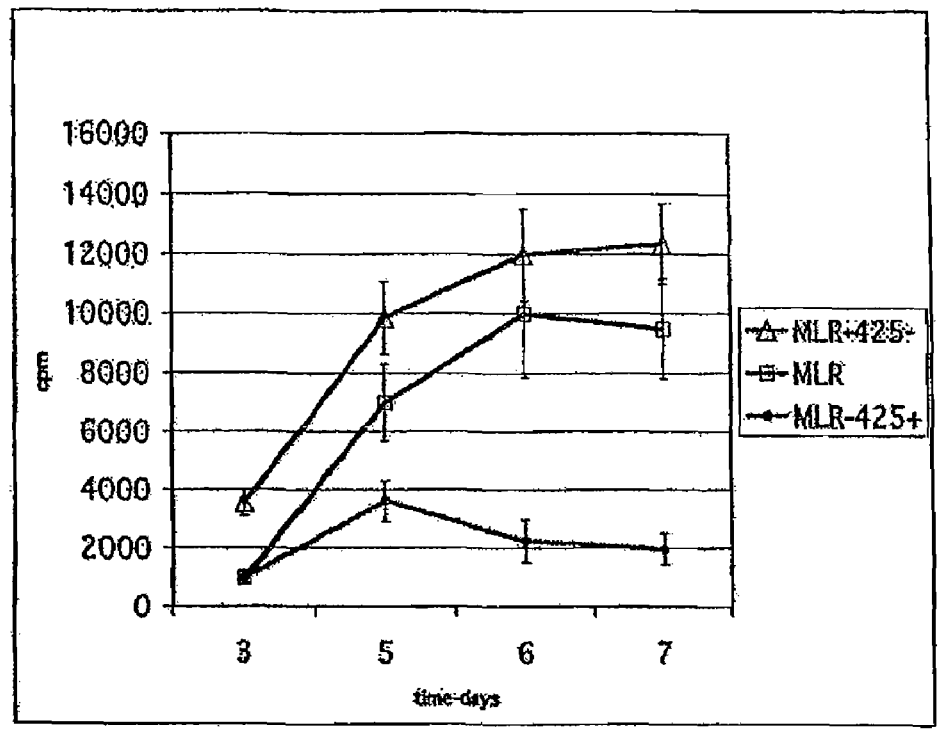
FIGS. 17A-17C depict purified cultured CD4$^+$CD25$^+$ cells that markedly suppress MLR. The MLR cultures contain various test cell populations at a (1:2) suppressor/responder cell ratio. Shown are kinetic curves of proliferation over a one week MLR. Cultures were pulsed daily with (3H)-Thymidine for last 16 hours of culture.
Figure 17B:
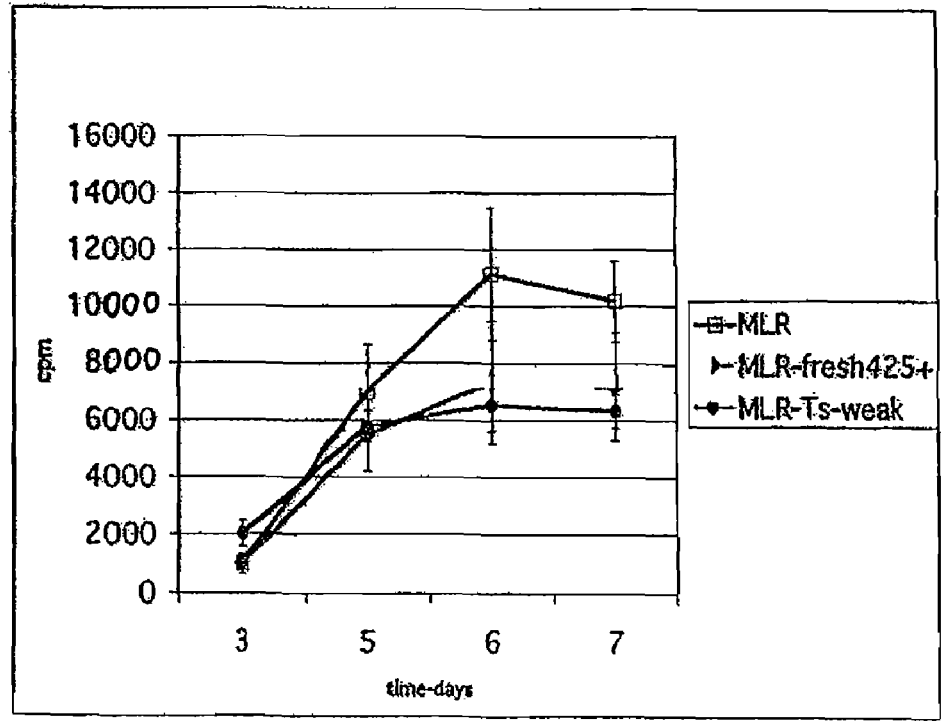
Figure 17C:
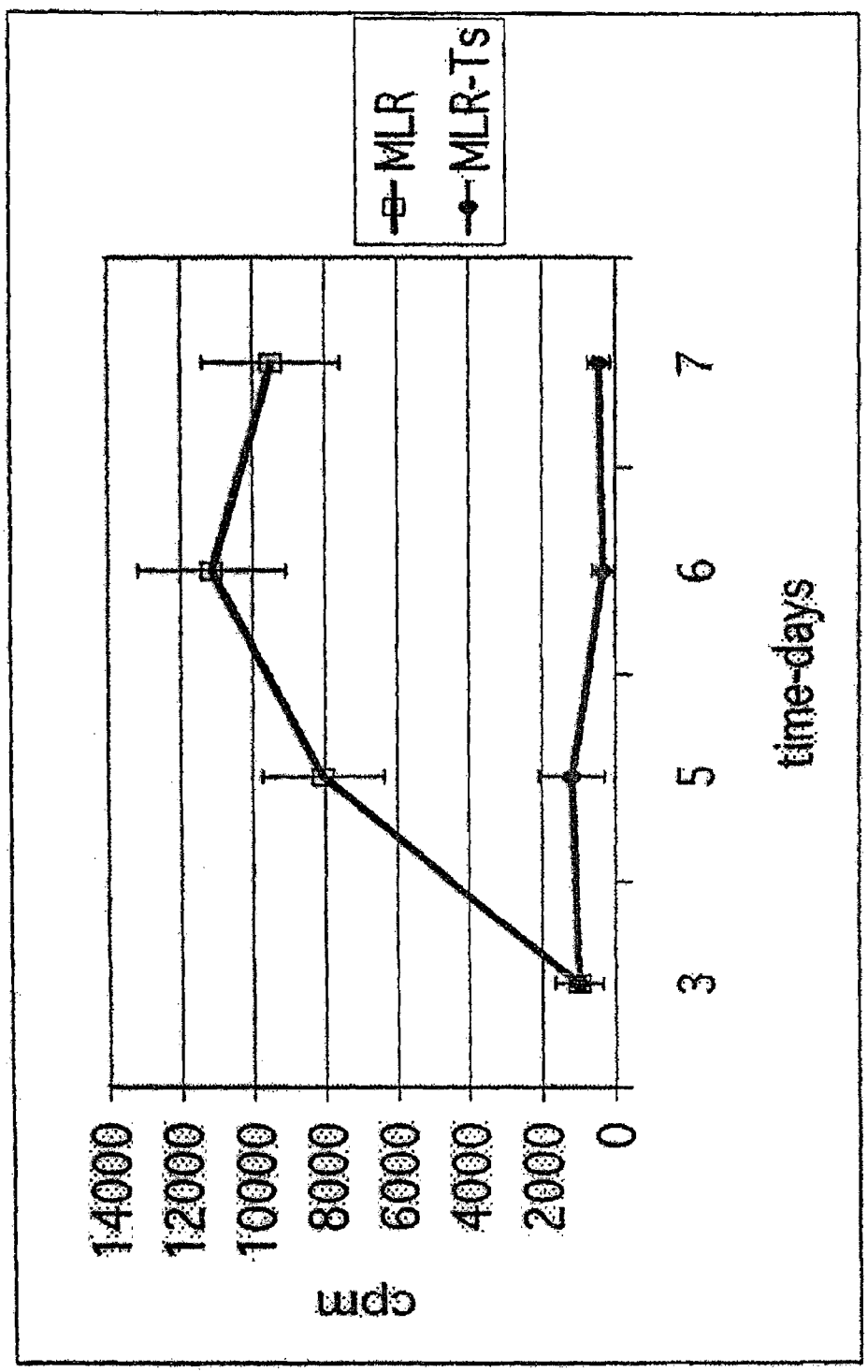

The majority of cell lines derived from $CD4^+CD25^+$ cells (19 of 25, 76%) had clear suppressive function (>65% inhibition of proliferation) at a suppressor/responder ratio of 1:2 (FIG. 17A). In contrast, cell lines derived from $CD4^+CD25^-$ cells were found invariantly to augment the MLR (FIG. 17A). The remaining $CD4^+CD25^+$ derived cell lines (6 of 25, 24%), had weak suppressive function (20-65% inhibition of proliferation). However, none augmented the MLR (FIG. 17B). Consistent with prior observations (Jonuleit et al., 2001, supra), freshly isolated MACS purified $CD4^+CD25^+$ cells have only modest suppressive activity in these MLR assays, equivalent to the weak suppressor cell lines (20-65% inhibition of proliferation) (FIG. 17B). Importantly, (9 of 19, 47%) of the suppressive cell lines had potent suppressor activity, and these cell lines almost completely inhibit MLR cultures (>90% inhibition of proliferation) (FIG. 3C). The level of suppressive activity was an intrinsic characteristic of each line, in that weak or potent suppressive cell lines had consistently similar activity when tested in multiple independent MLR experiments over several weeks of analysis (see below).

Characterization of $CD4^+CD25^+$ and $CD4^+CD25^-$ cell lines. Potent suppressor cell lines were cultured in parallel with $CD4^+CD25^-$ derived cell lines from the same individual, which served as conventional T-cell controls. The weakly suppressive cell lines were also characterized and compared to determine the distinguishing characteristics versus the potently suppressive cell lines. Interestingly, it was often possible to predict suppressor function based simply on growth characteristics in culture, where the most rapidly growing CD4+CD25+ lines generally had the least suppressive function (not shown).

Figure 18C:
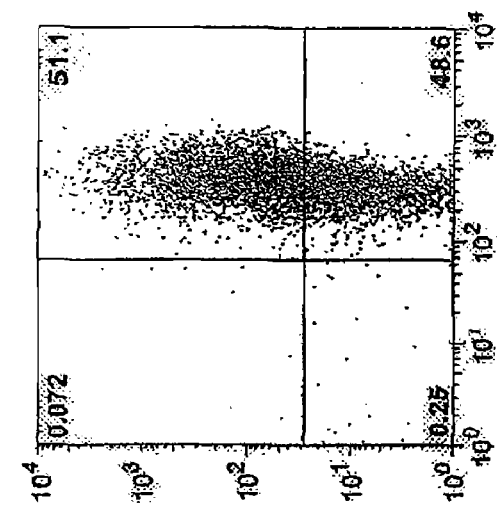
Figure 18B:
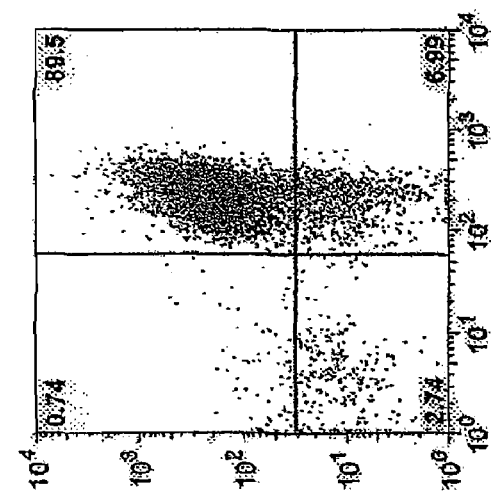
Figure 18A:
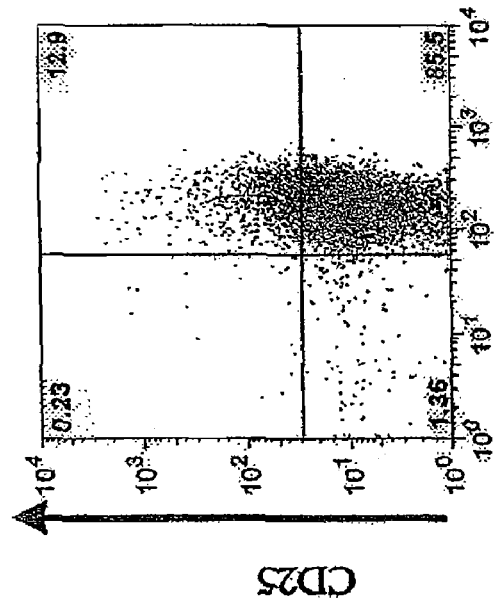

All cell lines initially expressed a somewhat typical activated T-cell phenotype after stimulation with the 3/28 beads. The cell lines transiently expressed relatively equivalent amounts of activation antigens, which quickly diminished over the 2-3 weeks after activation. These include CD122, CD132, GITR (glucocorticoid-induced TNF receptor), OX40 (CD134), and cell surface CTLA4 (CD152). However, after several weeks of culture, when the cells became relatively quiescent (maintained in IL-2), the phenotypes become clearly divergent. Compared with T-cell lines derived from CD25− cells, the strongly suppressive Treg cell lines expressed higher levels of CD25, and the elevated expression was sustained. The levels after 3 weeks of culture (MFI 22 vs. 210) are shown (FIGS. 18A, 18B). MFI refers to mean fluorescent intensity. In addition, intracellular staining for CTLA4 demonstrated enhanced expression in the suppressor cell lines (MFI 8 vs. 64) (FIGS. 18D, 18E). The differences in CD25 and intracellular CTLA4 expression were the most distinct phenotypic characteristics identified in our studies that distinguish conventional versus CD25+ derived cell lines. The weakly suppressive cell lines expressed intermediate amounts of these two key descriptive antigens (FIGS. 18C, 18F).

To determine further differences between the weakly and potently suppressive cell lines, additional cell surface antigen analysis was undertaken. A correlation was recorded of 3 antigens (CD62L, CCR7, and CD27) that were expressed on a higher percentage of cells in the potent suppressor cell lines compared with weak lines (FIGS. 18G, 18H, 18I). To further evaluate for functional relevance, magnetic beads were used to isolate CD62L+ or CD27+ cells (the brightest two antigens), and found enrichment for suppressor activity in both of the positive subsets (not shown). To more definitively determine function of these cell line subsets, cell lines were sorted for CD62L+/CD27+, CD62L+/CD27−, and CD62L−/CD27+ cells (FIG. 18J) and each population was tested for suppressor activity in MLR.

Figures 18J, 18K:
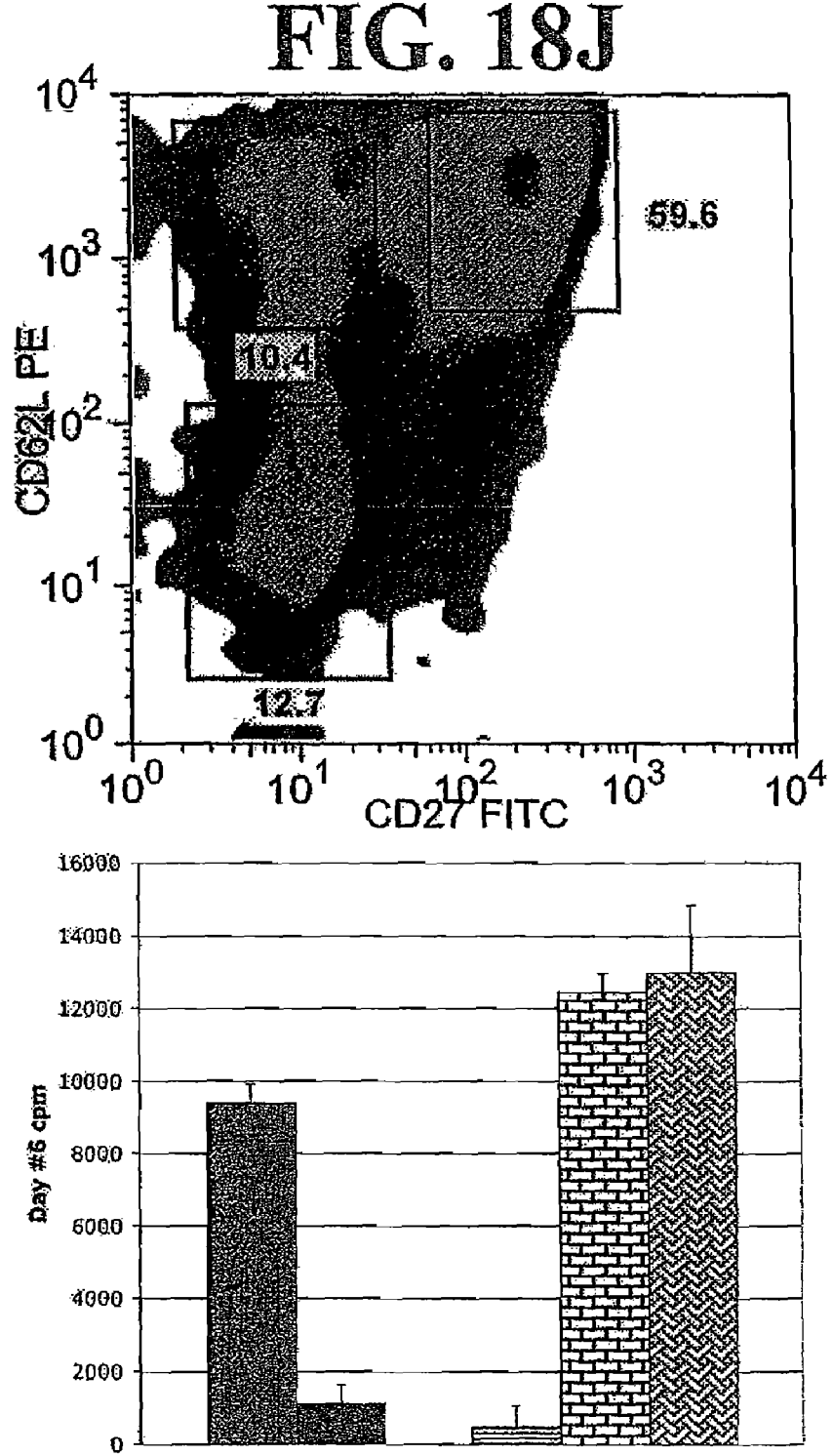

Suppressor function was solely within the CD62L+/CD27+ subset. In contrast, the other subsets were found to augment the MLR (FIG. 18K). Thus CD4+CD25+ cell lines can contain mixtures of suppressive and non-suppressive cells, and the suppressive effects can be dominant over the augmenting effects of the non-suppressors. CD62L and CD27 co-expression can be used to distinguish these subsets, and facilitate selection of cell lines (or cell line subsets) with potent suppressive potential.

Figure 19A:
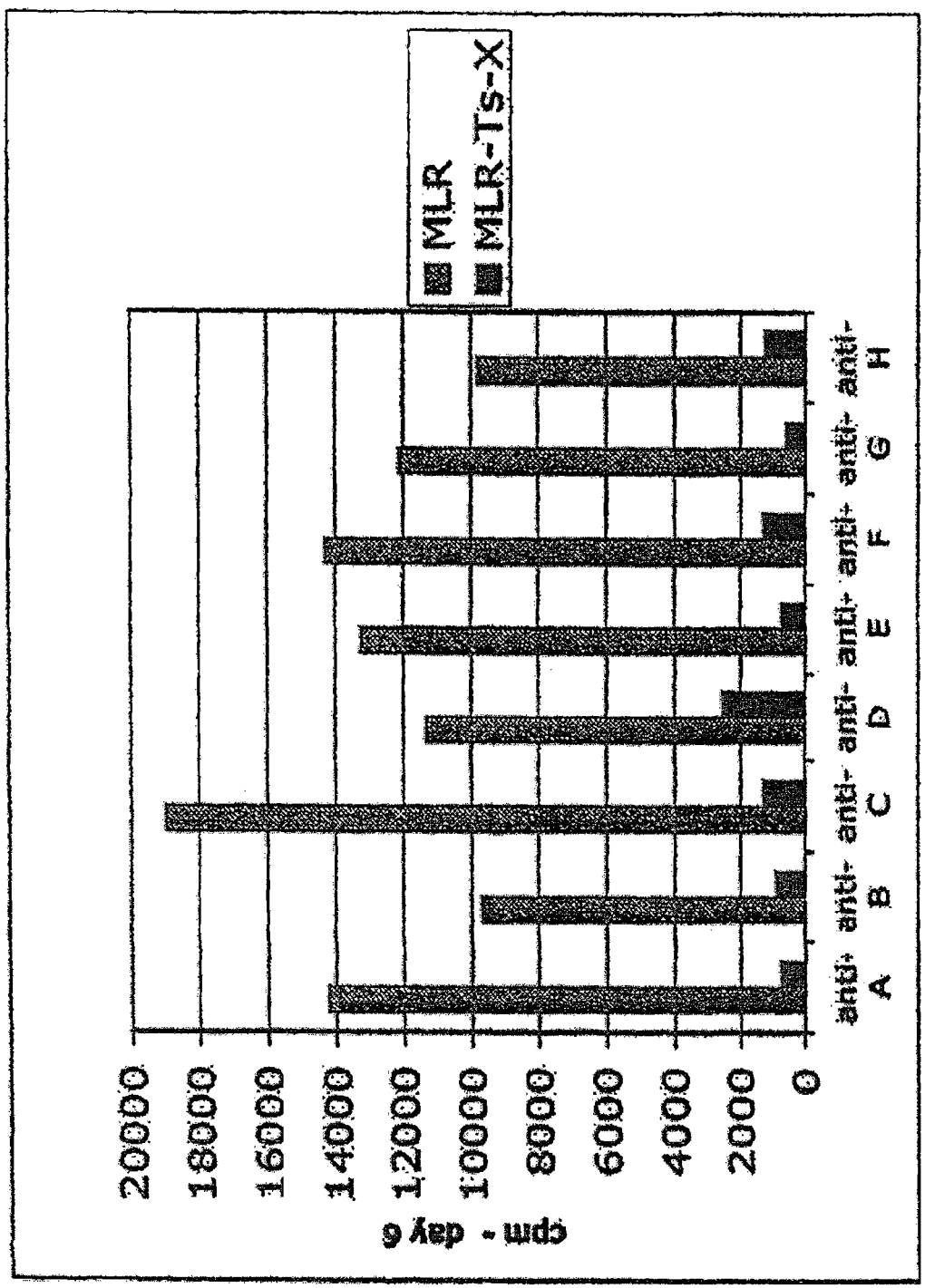
Figure 19B:
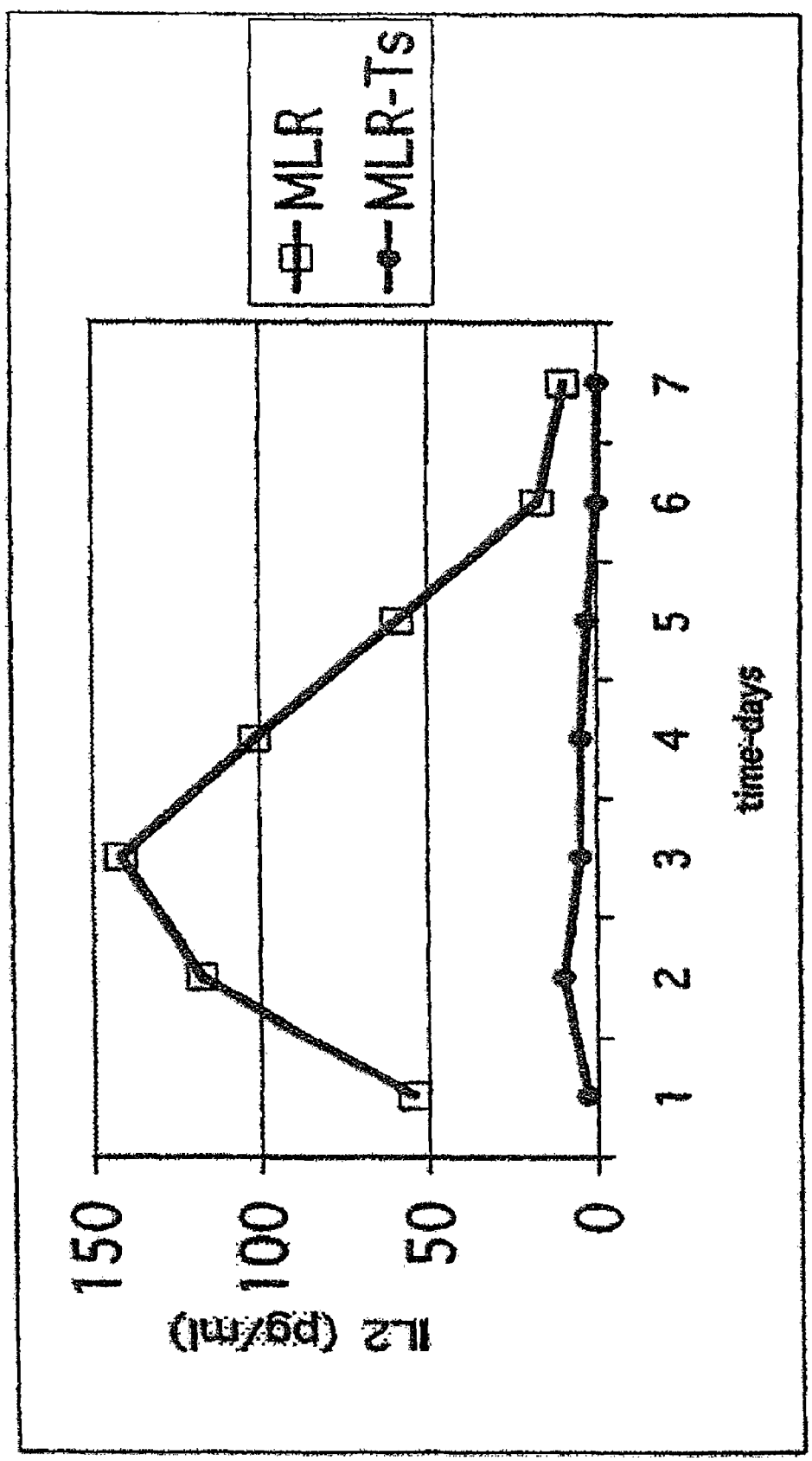

Characterization of Suppressor Cell Function in MLR Assays. To determine the cellular mechanism of suppression in the MLR assays, potent cell lines (>90% day 6 MLR suppression) were selected for further analysis. They were first shown to be consistently suppressive, and then titered to determine minimum number required for potent suppression. To determine how broadly reactive the cultured Treg cells are, several independent lines were tested for suppression in 8 separate HLA mismatched MLR cultures. In all cases, the cultured Treg cells markedly suppressed all MLR cultures analyzed (FIG. 19A). Although there was some variation in the magnitude of suppression (mean 92%, range 81-98%, n=16), potent Treg cell lines were effective in inhibiting almost all MLR cultures.

Figure 19C:
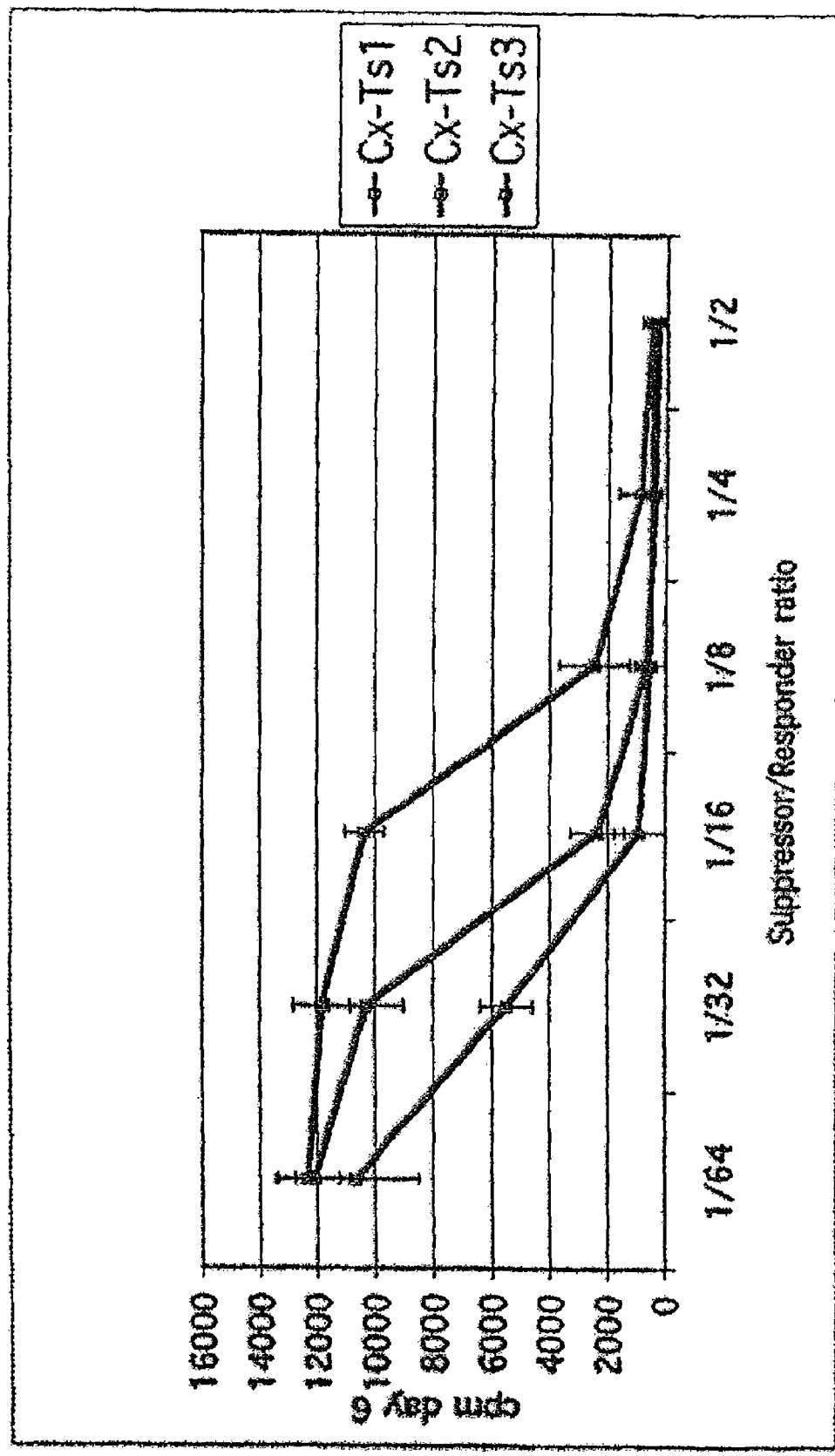

To quantify the minimum number of suppressor cells required for potent inhibition, titrated numbers of suppressor cells were added to indicator MLR cultures. The titration curves (FIG. 19B), revealed an approximate break point at a suppressor-to-responder ratio of less than 1:10 (5,000 suppressors to 50,000 responders). The titration curves were found to be non-linear, possibly indicating cooperative effects in the overriding of suppression with low Treg cell dose. Proliferation was nearly completely impaired in suppressed MLR at all time points, indicating that the suppressor effects occur within the first three days, i.e., prior to the proliferative burst in MLR. To evaluate for earlier effects and search for potential regulatory cell deviation of the quality of immune response, MLR supernatants were evaluated for cytokine content. There was a profound suppression of cytokine accumulation. Suppressed MLR make a minimally detectable small early wave of IL-2 (at the threshold of sensitivity of assay), with no late production detectable (FIG. 19C). As the control MLR manifested IL-2 accumulation in the supernatant, even one day after initiation of culture, the suppressor effect was detectable and already profound as early as the first day of the suppressed MLR. In addition, accumulation of late cytokines (peaks typically day 5-7), such as TNF-α, IFN-γ, GM-CSF, and IL-6 was nearly completely prevented throughout the culture (FIG. 19D). When cytokine supernatants were analyzed on the Luminex device, where small volumes (50-100 µl) suffice to test multiple cytokines at the same time, there was no induction of IL-4 or IL-10 to indicate deviation to a TH2 or T-regulatory type 1 (Tr1:IL-10 producing) differentiation. In fact, IL-10 accumulation was prevented as well.

Figure 20A:
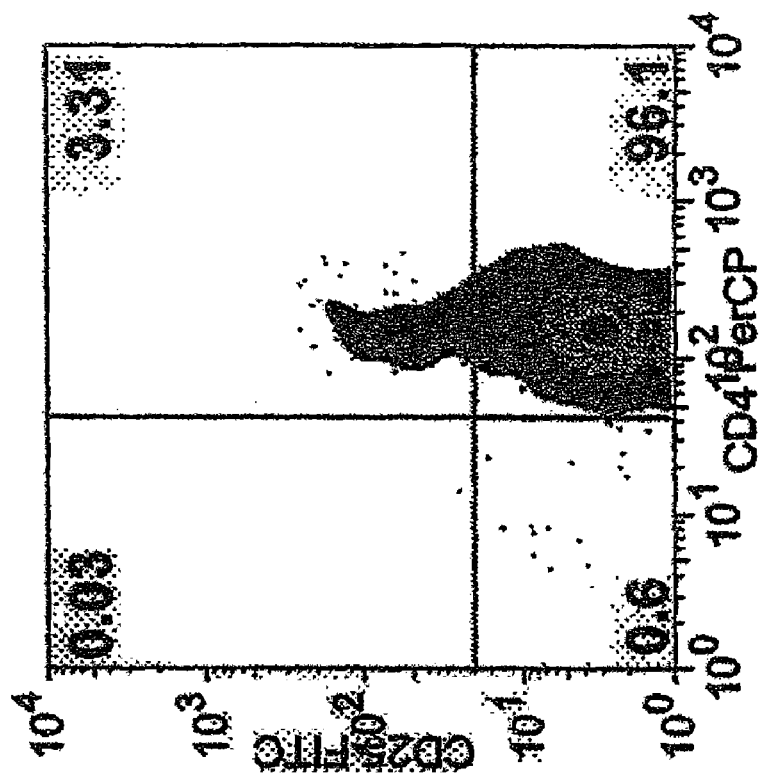
Figure 20B:
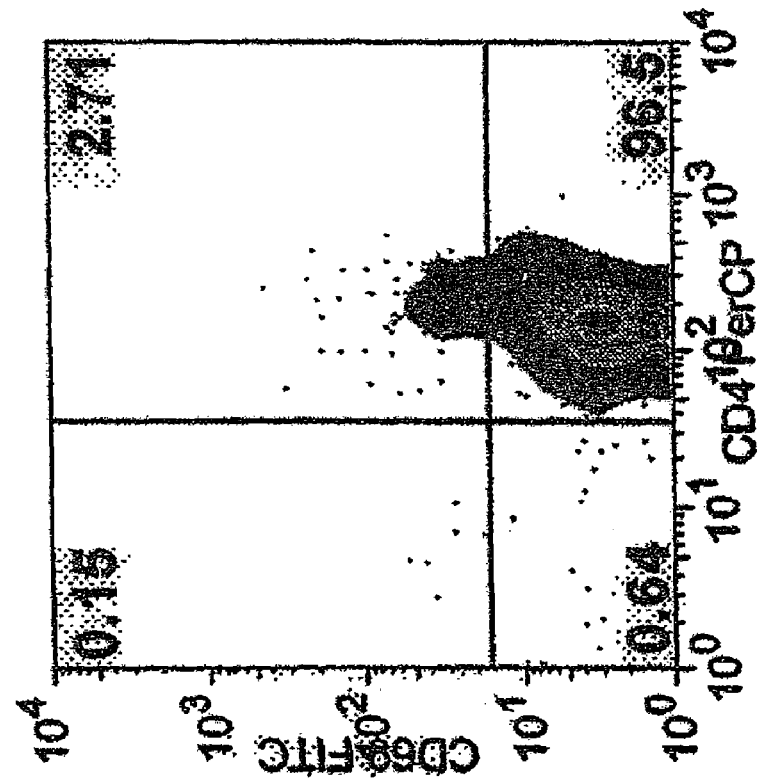

To examine responder T-cell reactivity early in the MLR, cells were assayed by flow cytometry for activation marker expression. Using responder cells derived from an HLAA2 positive donor, and suppressor cells derived from an HLA-A2 negative donor, the responding cells could be distinguished during co-culture. Control and suppressed MLR cells were evaluated 24 or 48 hours after initiation of culture for induction of CD69, CD25, and OX40 (CD134). In the control MLR, the 2-4% of responder T-cells showed expression of these activation antigens (FIGS. 20A-C), consistent with the expected alloreactive T-cell frequency for HLA-mismatched MLR. Notably, in the suppressed MLR very few responder T-cells showed expression of these activation antigens (FIGS. 20D-F). These data further demonstrate a very early block in T-cell activation as a mechanism of Treg cell action.

The potency of suppression was remarkably retained if the DC stimulating the MLR were activated or matured. Maturation/activation of DC with lipopolysaccharide (LPS), a TLR4 ligand, or the combination of tumor necrosis factor/polyIC, a double stranded RNA analog-TLR 3 ligand) (Spisek et al., 2001, supra; Godfrey et al., 2004, supra), did not lead to bypass of suppression (FIG. 20G). Inclusion of LPS or TNF/Poly IC in the MLR culture also did not bypass suppression. Thus, the cultured human Treg cells were very potent, and activated DC, which express abundant costimulatory molecules and cytokines, were not able to bypass their suppressive effect.

The potent and early inhibition of MLR suggests APC inactivation or elimination as a possible mechanism of suppression. However, by microscopic evaluation, the DC appear to persist for the duration of culture. In addition, the suppressor cell lines did not have cytotoxicity for allogeneic DC (FIG. 21A) or NK/LAK sensitive targets (K562) (FIG. 21B) in chromium release assays.

Figure 21A:
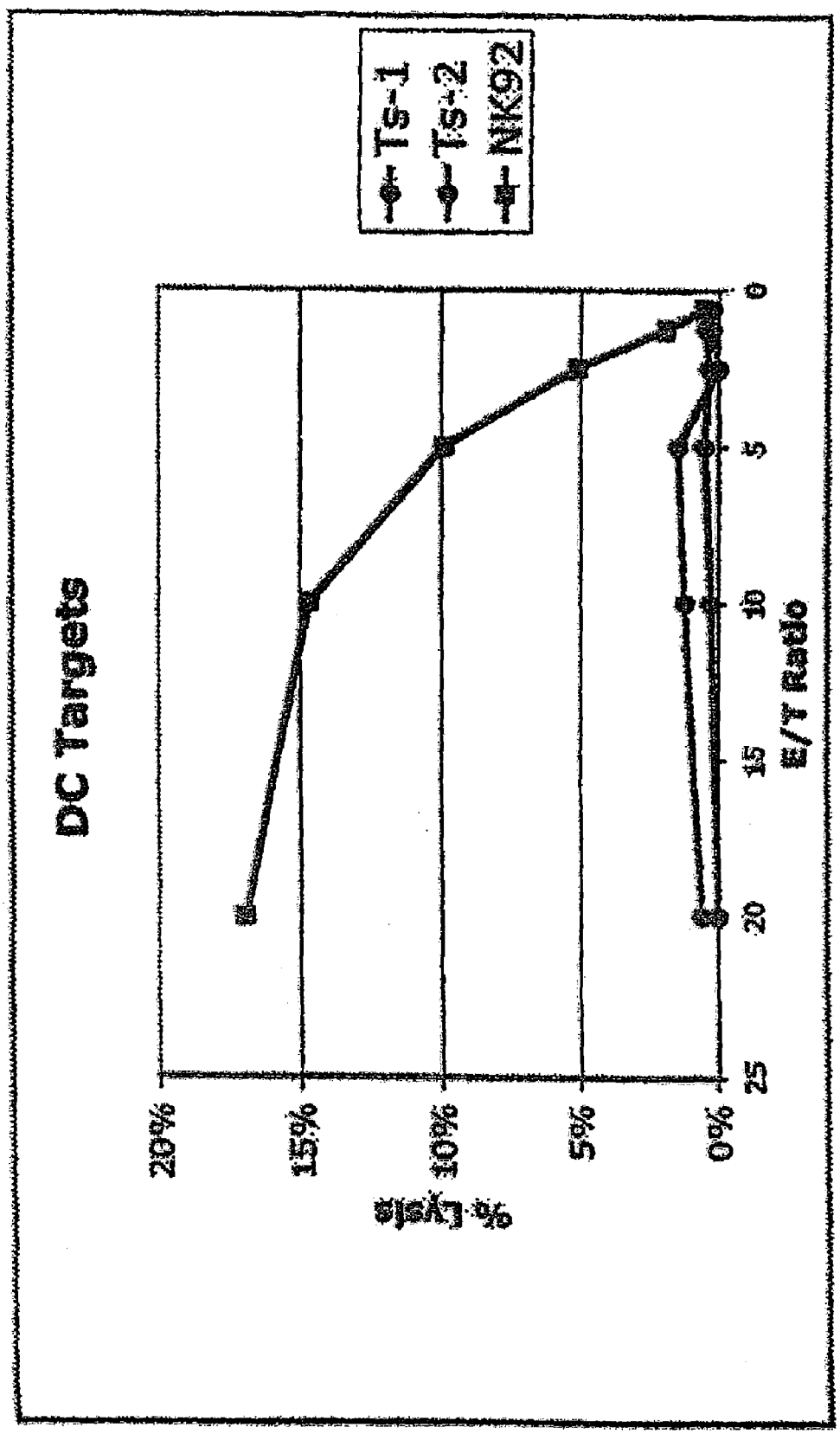
Figure 21C:
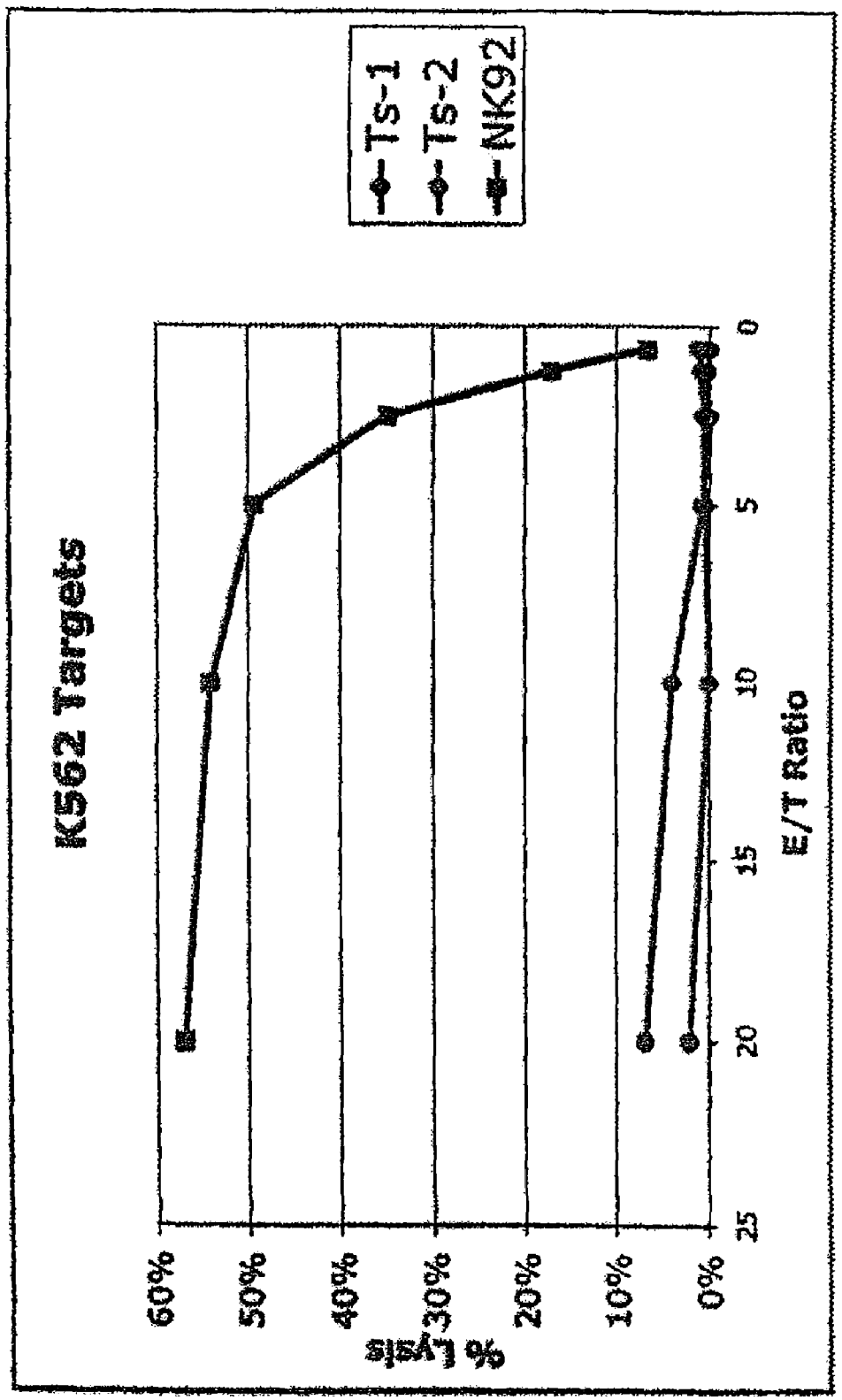

To determine if known immunosuppressive factors were mediating the action of the cultured Treg cells, antibodies capable of neutralizing IL-10 or TGF-β were added to control and suppressed MLR cultures. Because of the potency of the suppressive effect, lower numbers of suppressors were added to make the assay more sensitive to reversal of suppression. Despite this reduction, antibodies reactive with IL-10, IL-10R-alpha, or TGF-$\beta_{123}$, failed to reverse suppression and the inclusion of all three antibodies together had a very modest effect (FIG. 21C). Doses of 1, 10, or 20 micrograms per ml were tested with the effects only noted at the highest dose levels.

In addition, trans-well studies were undertaken to determine if soluble factors released by Treg cells could convey suppression. Indicator MLR cells were cultured above resting or activated Treg cells or suppressed MLR cultures, separated by membranes with 0.4 micron pores. No suppressive effect was found to pass through the membrane (not shown).

Figure 21D:
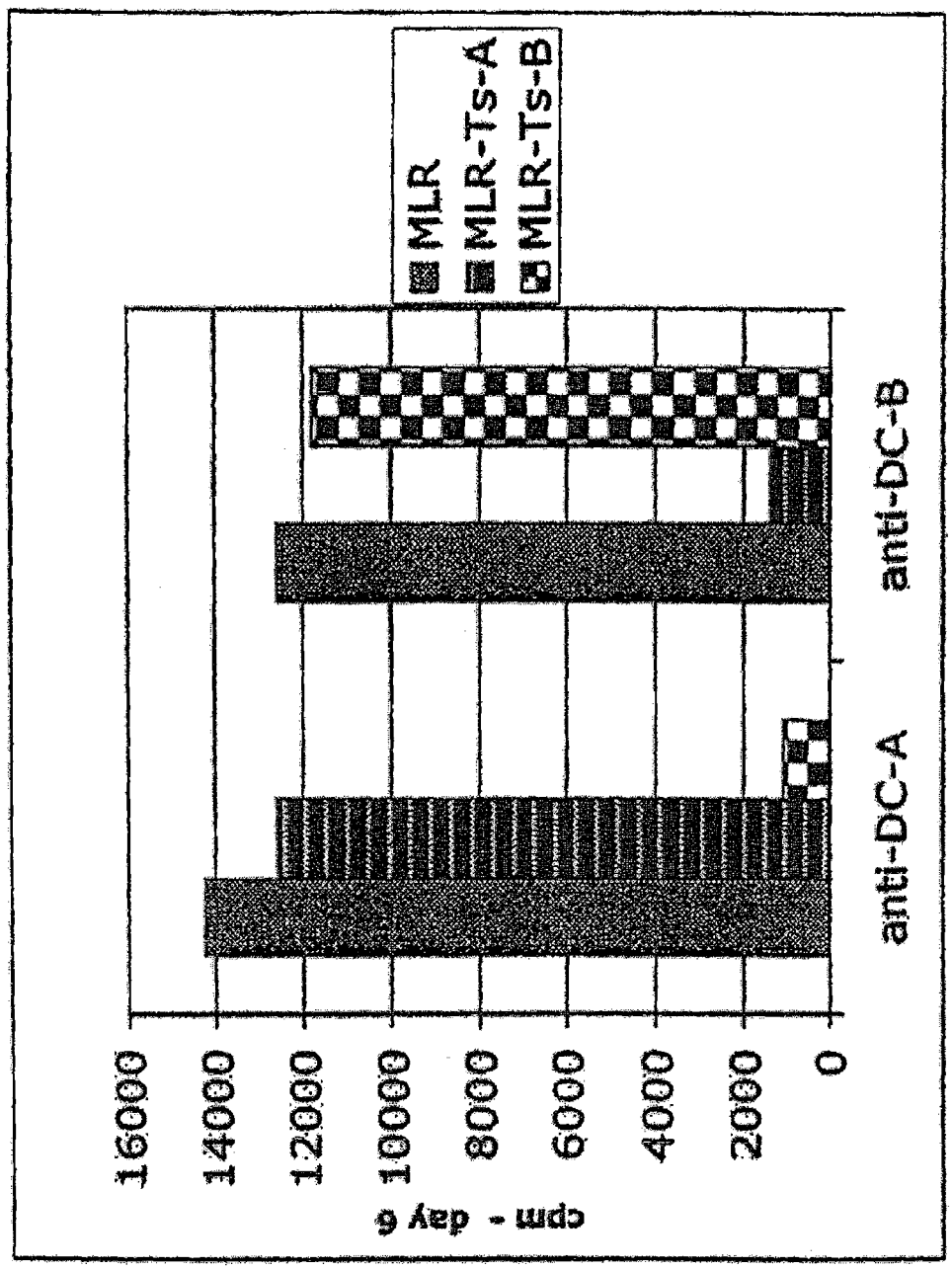

Importantly, when cultured Treg cells were added to allo-MLR driven by APC that were derived from the same donor as the suppressors, but still allogeneic to responder T cells, minimal suppression was noted (FIG. 21D). Thus, when cultured Treg derived from Donor A are added to an allo-MLR driven by DC's from the same Donor A, there is minimal suppression. However, these same Treg cells, when added to an MLR driven by DC from Donor B, result in suppression. These results indicate that the cultured Treg cells are not constitutively suppressive of all MLR. The cultured Treg need some form of specific additional stimulation that can be provided by allo-DC (and not by autologous DC).

In sum, this example demonstrates that suppressor cells can be isolated and culture expanded from human blood. Importantly, these cultured Treg cells can be expanded over 100-fold, and when pure express enhanced and potent suppressive activity. In fact, the suppressive function of these cells in MLR assays was shown to almost completely block HLA mismatched MLR. Moreover, these culture-expanded suppressor cells have many of the hallmark features of the freshly isolated CD4$^+$CD25$^+$ Treg cells. They highly express CD25 and cytoplasmic CTLA4, their activity is cell-cell contact dependent, and suppression does not seem to be dependent cytolytic activity or on the immunosuppressive cytokines IL-10 or TGF$\beta$.

In addition, these data are the first to demonstrate feasibility of anti-CD3/28 mAb coated bead-based approach for Treg cell activation and expansion. The suppressor cell lines do not respond proliferatively in direct co-cultures with DCs. When anti-CD28 is combined with anti-CD3 mAb a more efficient expansion strategy results. Despite anti-CD3/CD28 mAb-coated bead-based and IL-2 supplemented activation, stringently purified CD4$^+$CD25$^+$ cells (or FACS sorted CD4$^+$CD25$^+$ bright cells) did not grow well. Growth was better with the addition of CD4$^+$CD25$^-$ feeders, which provide IL-2 and other growth factors. CD4$^+$CD25$^+$ cell line growth and suppressor function was variable and inversely correlated, possibly because cell lines with poor suppressor function resulted from inclusion of small numbers of conventional T cells in the CD4$^+$CD25$^+$ cultures. Cell lines derived from more stringently purified cells did not grow as well but were more potent suppressors. In addition, the immunophenotype of the weakly suppressive cell lines (CD25 moderate, and split CD62L or CD27) was consistent with a mixed population of conventional and suppressive cells. However, it is interest to note that after culture, the functionally active suppressor cells were exclusively within the CD62L and CD27 expressing population, and the potent suppressor cell lines nearly uniformly expressed these antigens.

Importantly, the suppressor effector function of CD4+CD25+ cells is not MHC-restricted, and the suppressor cells will impair responses from virtually any donor combination. This lack of HLA restriction also opens the possibility of using third party (allogeneic) donors for generation of the suppressor cells. By applying the presently disclosed concepts and mechanisms to human disease pathogenesis, then isolating Treg cells for ex vivo treatment and long-term, culture-extending the Treg cells in accordance with the present invention, followed by infusing the resulting cultured Treg cells to patients offers a method for treating auto-immune responses or improving the outcomes in bone marrow or other transplantations. The availability of large numbers of cultured Treg cells will enable more detailed immunological, biochemical, and molecular characterization of these important cells. However, perhaps more importantly, because the present methods are adaptable for GMP conditions, clinical testing may soon be feasible, and cultured Treg cells may be permitted as a novel form of immunosuppressive therapy.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims. cultured suppressor cell lines

We claim:

1. A population of activated and ex vivo culture-enhanced suppressor Treg cells, wherein said culture expanded Treg cells have been cultured with anti-CD3 antibody and anti-CD28 antibody in the presence of a CD4$^+$ feeder cell or CD4$^+$ feeder cell conditioned medium, thereby producing therapeutic Treg cells with enhanced suppressor activity, wherein said culture expanded Treg cells are CD62L$^+$/CD27$^+$ and are capable of inhibiting proliferation of CD4$^+$CD25$^-$ responding T cells in a Mixed Lymphocyte Reaction (MLR) assay by at least 90%.

2. A population of activated and ex vivo culture-enhanced suppressor Treg cells produced by a method comprising:
   selecting a sample of human CD4$^+$ T cells;
   contacting said sample with an anti-CD25 antibody;
   isolating cells that bind to said anti-CD25 antibody from said sample using a double column magnetic antibody cell sorting (MACS) purification procedure, to produce an isolated population of human CD4$^+$CD25$^+$ Treg cells;
   culture-expanded said population of human CD4$^+$CD25$^+$ Treg cells comprising contacting said isolated population of human CD4$^+$CD25$^+$ Treg cells with immobilized anti-CD3 antibody and immobilized anti-CD28 antibody, further culture-expanding said isolated population of human CD4$^+$CD25$^+$ Treg cells in the presence of a CD4$^+$ feeder cell or CD4$^+$ feeder cell conditioned medium, thereby producing therapeutic human Treg cells with enhanced suppressor activity, wherein said culture expanded Treg cells are CD62L$^+$/CD27$^+$ and are capable of inhibiting proliferation of CD4$^+$CD25$^-$ responding T cells in a Mixed Lymphocyte Reaction (MLR) assay by at least 90%.

* * * * *